(12) United States Patent
DeCarlo

(10) Patent No.: US 10,112,076 B2
(45) Date of Patent: Oct. 30, 2018

(54) ROBOTIC ATHLETIC TRAINING OR SPORTING METHOD, APPARATUS, SYSTEM, AND COMPUTER PROGRAM PRODUCT

(71) Applicant: Christopher DeCarlo, Fairfax, VA (US)

(72) Inventor: Christopher DeCarlo, Fairfax, VA (US)

(73) Assignee: Christopher DeCarlo, Fairfax, VA (US)

( * ) Notice: Subject to any disclaimer, the term of this patent is extended or adjusted under 35 U.S.C. 154(b) by 0 days.

(21) Appl. No.: 15/729,663

(22) Filed: Oct. 10, 2017

(65) Prior Publication Data

US 2018/0093133 A1     Apr. 5, 2018

Related U.S. Application Data

(63) Continuation-in-part of application No. 15/437,432, filed on Feb. 20, 2017, now Pat. No. 9,782,648, which
(Continued)

(51) Int. Cl.
*A63B 63/00* (2006.01)
*A63B 24/00* (2006.01)
(Continued)

(52) U.S. Cl.
CPC ........ *A63B 24/0075* (2013.01); *A61B 5/0022* (2013.01); *A61B 5/6895* (2013.01); *A63B 63/00* (2013.01); *A63B 63/004* (2013.01);

*A63B 63/083* (2013.01); *A63B 69/00* (2013.01); *A63B 69/002* (2013.01); *A63B 69/0024* (2013.01);
(Continued)

(58) Field of Classification Search
None
See application file for complete search history.

(56) References Cited

U.S. PATENT DOCUMENTS 3,888,023 A * 6/1975 Genin ................... A63B 69/00
                                                                    40/411
5,647,747 A * 7/1997 Macri ................ A63B 24/0003
                                                                   434/247
(Continued)

*Primary Examiner* — Jason Yen
(74) *Attorney, Agent, or Firm* — ATFirm PLLC; Ralph P. Albrecht

(57) ABSTRACT

A sporting robotic device apparatus, system, method and/or computer program product may provide an electronically programmably controlled sporting device. Certain embodiments include a plurality of sporting devices coupled to a robot or a plurality of the at least one robots, where the plurality of robots each include a sporting device coupled to the plurality of robots, and where each robot includes a plurality of joint axes, motors, and structural members. The sporting robotic device can further include an electronic user interface coupled to the robots and an electronic computer processor, memory, input and output devices, and can include further features as claimed including at least one of the user interface with devices coupled thereto, the computer processor configured to save or retrieve a sporting routine from memory, to randomize a challenge, or configured to combine sporting routines, or shuffle sporting routines, previously saved.

20 Claims, 28 Drawing Sheets

Related U.S. Application Data is a continuation-in-part of application No. 15/237,631, filed on Aug. 16, 2016, now Pat. No. 9,573,035, which is a continuation-in-part of application No. 14/261,435, filed on Apr. 25, 2014, now Pat. No. 9,415,263.

(51) Int. Cl.

| | | |
|---|---|---|
| *A63B 69/00* | (2006.01) | |
| *G06N 3/08* | (2006.01) | |
| *A63B 69/38* | (2006.01) | |
| *A63B 71/06* | (2006.01) | |
| *A63B 69/36* | (2006.01) | |
| *A61B 5/00* | (2006.01) | |
| *A63B 63/08* | (2006.01) | |
| *F41J 1/00* | (2006.01) | |
| *F41J 1/01* | (2006.01) | |
| *F41J 1/10* | (2006.01) | |
| *F41J 3/00* | (2006.01) | |
| *F41J 5/02* | (2006.01) | |
| *F41J 5/052* | (2006.01) | |
| *G06F 19/00* | (2018.01) | |
| *G06N 5/02* | (2006.01) | |
| *G09B 19/00* | (2006.01) | |
| *A63B 102/14* | (2015.01) | |
| *A63B 69/10* | (2006.01) | |
| *A61B 5/11* | (2006.01) | |

(52) U.S. Cl.
CPC ...... *A63B 69/0026* (2013.01); *A63B 69/0071* (2013.01); *A63B 69/36* (2013.01); *A63B 69/38* (2013.01); *A63B 71/0619* (2013.01); *A63B 71/0622* (2013.01); *F41J 1/00* (2013.01); *F41J 1/01* (2013.01); *F41J 1/10* (2013.01); *F41J 3/00* (2013.01); *F41J 5/02* (2013.01); *F41J 5/052* (2013.01); *G06F 19/3481* (2013.01); *G06N 3/08* (2013.01); *G06N 5/022* (2013.01); *G09B 19/0038* (2013.01); *A61B 5/1113* (2013.01); *A61B 5/1124* (2013.01); *A61B 5/681* (2013.01); *A61B 5/744* (2013.01); *A61B 5/745* (2013.01); *A61B 2503/10* (2013.01); *A61B 2562/0204* (2013.01); *A61B 2562/0219* (2013.01); *A63B 24/0087* (2013.01); *A63B 63/008* (2013.01); *A63B 69/10* (2013.01); *A63B 2024/0025* (2013.01); *A63B 2024/0037* (2013.01); *A63B 2024/0068* (2013.01); *A63B 2069/0006* (2013.01); *A63B 2071/065* (2013.01); *A63B 2071/0625* (2013.01); *A63B 2071/0675* (2013.01); *A63B 2102/14* (2015.10); *A63B 2207/02* (2013.01); *A63B 2210/50* (2013.01); *A63B 2220/13* (2013.01); *A63B 2220/24* (2013.01); *A63B 2220/30* (2013.01); *A63B 2220/34* (2013.01); *A63B 2220/44* (2013.01); *A63B 2220/56* (2013.01); *A63B 2220/62* (2013.01); *A63B 2220/801* (2013.01); *A63B 2220/802* (2013.01); *A63B 2220/805* (2013.01); *A63B 2220/833* (2013.01); *A63B 2225/09* (2013.01); *A63B 2225/20* (2013.01); *A63B 2225/50* (2013.01); *A63B 2243/007* (2013.01)

(56) References Cited

U.S. PATENT DOCUMENTS

| | | | |
|---|---|---|---|
| 7,860,614 B1* | 12/2010 | Reger | B25J 9/1671 700/10 |
| 2012/0142458 A1* | 6/2012 | He | A63B 63/083 473/480 |
| 2013/0346348 A1* | 12/2013 | Buehler | B25J 9/0087 706/12 |
| 2014/0378281 A1* | 12/2014 | Mazi | A63B 69/34 482/83 |

* cited by examiner

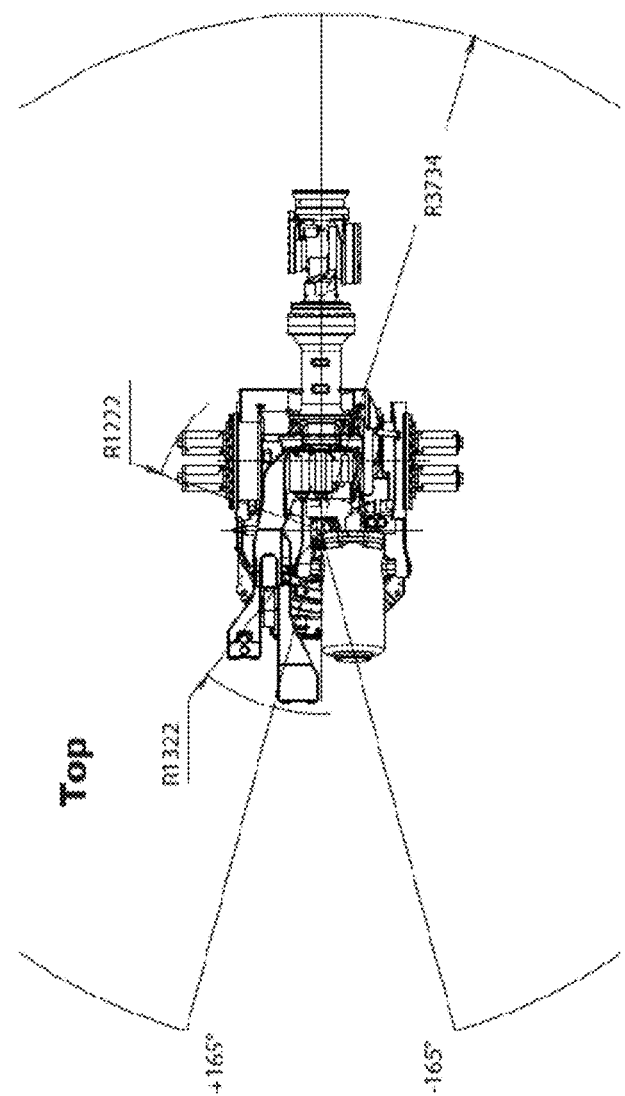

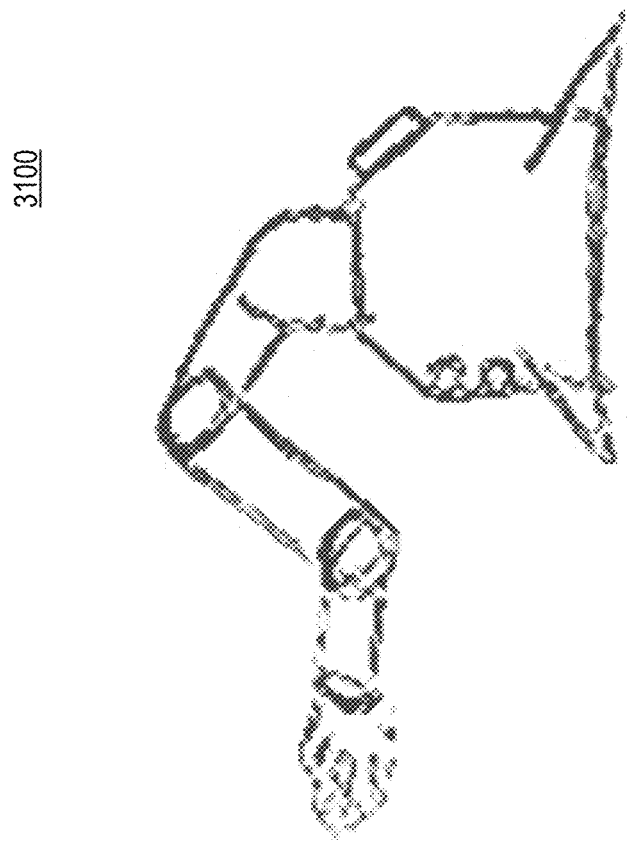
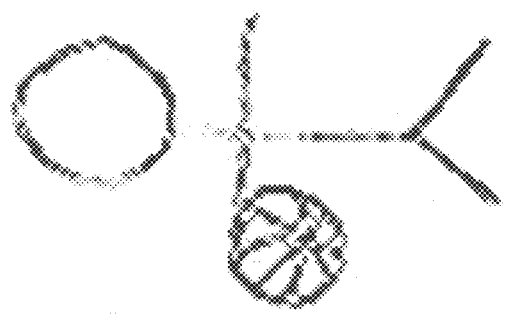
FIG. 31

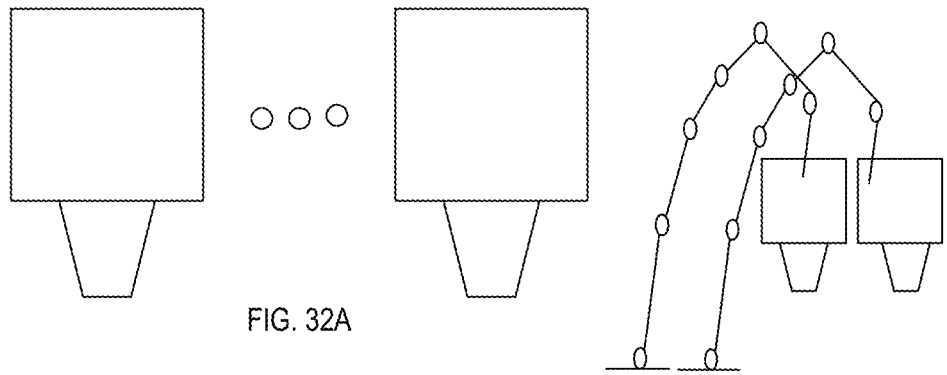
FIG. 32A
FIG. 32E
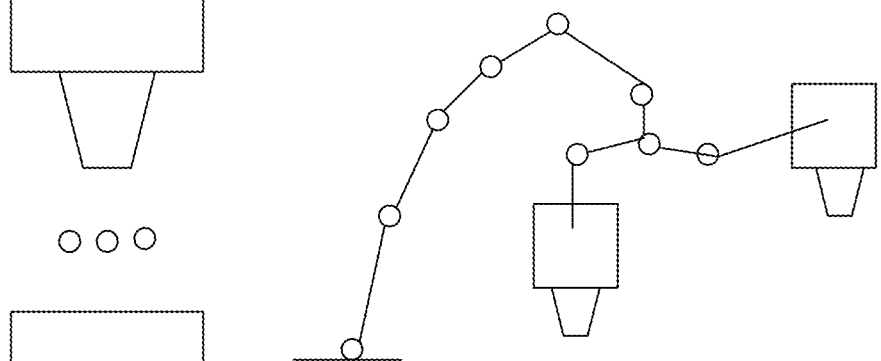
FIG. 32B
FIG. 32F
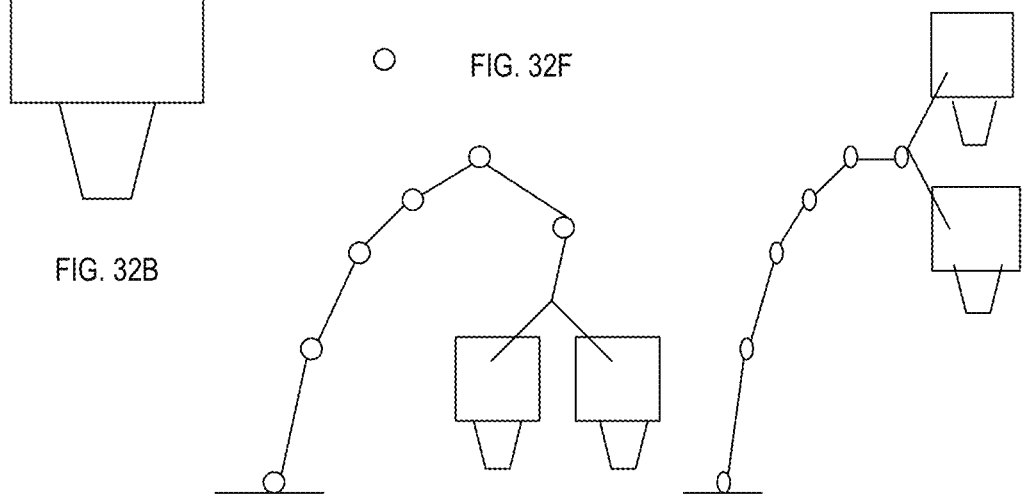
FIG. 32C
FIG. 32D

10,112,076 B2

ROBOTIC ATHLETIC TRAINING OR SPORTING METHOD, APPARATUS, SYSTEM, AND COMPUTER PROGRAM PRODUCT

CROSS-REFERENCE TO RELATED APPLICATION

This application is a continuation-in-part filed Oct. 10, 2017 of, and claims priority to U.S. patent application Ser. No. 15/437,432, filed Feb. 20, 2017, allowed and issuing as U.S. Pat. No. 9,782,648 on Oct. 10, 2017, which is a continuation-in-part of, and claims priority to U.S. patent application Ser. No. 15/237,631, filed Aug. 16, 2016, allowed and issuing as U.S. Pat. No. 9,573,035 on Feb. 21, 2017, which is a continuation-in-part of and claims priority to U.S. patent application Ser. No. 14/261,435, filed Apr. 25, 2014, allowed and issuing as U.S. Pat. No. 9,415,263 on Aug. 16, 2016, the contents of all of which are incorporated herein by reference in their entireties.

BACKGROUND OF THE DISCLOSURE

Field of the Disclosure

The present invention relates generally to training devices, and more particularly to athletic training devices, and even more particularly to electronic athletic training devices.

Discussion of the Related Art

Conventionally, various athletic training devices have existed but have various shortcomings.

Early athletic ball games include Lacrosse played by native Americans, Jai-Alai a sport originating in northern Spain, as well as association football (soccer) formalized in the United Kingdom, involving kicking a ball into a goal, tracing its ancestry to Episkyros of Ancient Greece, and Harpastum of early Rome. Other ball-based sports may include fieldhockey, tennis, squash, handball, etc. Other sports may use a slightly different shaped ball including, e.g., but not limited to, a puck for ice hockey, and an oblong spheroid for American football, etc. Various other sports involve throwing or hitting a ball or other projectile, such as baseball, softball, shotput, javelin, etc. Sports generally have a given set of rules, and often require an athlete to develop eye-hand and/or eye-foot coordination to be successful.

One illustrative example of a ball-based athletic sport, basketball, is an athletic or sports competition to determine which of two teams of one or players can place or throw a ball vertically down through a target hoop the most times with the opposing player or team trying to keep the ball from going through the hoop by blocking the player or interfering with the ball on its way to the hoop. Basketball was invented by Dr. James Naismith in 1891. The hoops in a basketball game are attached to a backboard and are generally located 10 feet above the floor in a horizontal position. Originally the hoop was a basket, hence the name, but today, the hoop is conventionally a resilient metal ring with a replaceable (often nylon or cotton) woven net.

The primary object of basketball is to score by throwing the ball into the goal, officially called the "basket." A basket is scored when the ball passes completely through the basket ring from above; however, the number of points scored with each basket can vary by distance from which the ball is thrown, and a team need not necessarily score the most baskets to win a game. A basket scored during normal play is called a field goal and is worth two points if shot from within or on the three-point line, and three points if shot from beyond the three-point line. The three point line's distance from the goal may vary by level of play (e.g., high school, college, professional, etc.). Points are automatically awarded to the shooting team if, while the ball is in its flight towards or is over the basket, the defending team illegally touches the ball or basket, known as goaltending or basket interference. An alternate method of scoring in basketball is the free throw, which scores one point. A free throw scores the same way as a field goal, except that it is taken unopposed from a free-throw line after a foul. Basketball scores are expressed in total points.

The basket in basketball generally includes a metal hoop or ring 18 inches (46 cm) in internal diameter, suspended horizontally 10 feet (3.0 m) above the floor such that the center of the ring is equidistant from each sideline and 5 feet 3 inches (1.60 m) from the end line. The basket ring may have a net attached below to briefly check the ball's downward progress and indicate a score. The ring may be fastened to a generally rectangular backboard 6 feet (1.8 m) wide by 3.5 feet (1.1 m) tall, though in lower levels of play or recreational use the backboard may be smaller and/or fan-shaped. Conventionally, the entire structure may be supported from behind and anchored to the floor beyond the end line at higher levels of play; the structure may be anchored to a wall or ceiling at lower levels of play. The ring, net, and the front, top, bottom, and sides of the backboard may all be considered inbounds, while the back of the backboard and the support structure—even those parts suspended over inbounds areas of the court—may be considered out of bounds.

Players have a better chance of placing the ball in the basketball hoop if they have physical attributes such as height and developmental attributes such as dexterity, and so-called good coordination. For example, good eye-hand coordination is helpful for a player as the player uses the player's eyes to judge distance and the player's arms and body to propel the ball with proper force and direction to go through the hoop.

To improve eye hand coordination, a player may conventionally practice shooting the ball from a static position with feet stationary, or from a dynamic position where the player's feet and body are moving. Players are taught to use their bodies as well as hands and arms to help propel and direct the ball towards the hoop and in a game the players move their bodies to avoid and to get around the opposing players, which are trying to block the players and the ball.

In practicing for a game, players spend a lot of time shooting the ball at the hoop, which is conventionally fixed and stationary. The hoop is conventionally fixedly mounted to a backboard and the backboard is generally fixed to a floor, wall or ceiling, or placed on a fixed platform.

The players are always moving during a game as the players try to have a clear path of travel for the ball from the players' hands to the hoop and generally in practice players simulate the movements they can use in a game by putting their bodies in motion to improve their dynamic eye-hand coordination. The same kind of body movements players use in a game can be simulated by moving one's body in a dynamic way and shooting, but this may quickly become fatiguing.

Various so-called "goal-only" sports exist, where the only method of scoring is the goal. Examples of goal-only sports include Association football (soccer), ice hockey, field hockey, handball, lacrosse, water polo, polo, etc. Various other sports (in addition to basketball) permit scoring other than by single points for a goal including Australian rules football (6 point goals), and Gaelic football and hurling. Sports with goals as secondary scoring include American and Canadian football, Arena football, and Rugby.

Various conventional athletic training systems are known, but all fail to provide an optimal training experience simulating real world, in game variable movement, in a compressed training area.

Conventional athletic training and systems have various shortcomings. What is needed is an improved system and method of providing athletic training that overcomes various shortcomings of conventional solutions.

SUMMARY OF VARIOUS EXEMPLARY EMBODIMENTS

Various exemplary embodiments of an apparatus, system, method and computer program product for providing an improved athletic training apparatus, system, method and/or computer program product as is set forth in detail herein.

According to one exemplary embodiment, a computer implemented athletic training apparatus, system, method and/or computer program product may include providing a robotically controlled moveable athletic training device, which may include a plurality of sensors to sense a ball or projectile proximate to the athletic training device.

According to one exemplary embodiment, a goal, a moving hoop or target may allow the player to develop and practice dynamic shooting or other athletic interaction without the fatigue associated with accelerating and decelerating the player's body with each dynamic practice shot.

According to one exemplary embodiment, an athletic training apparatus, system, method and/or computer program product may include: a robot; and an athletic training device, such as a goal, coupled to said robot. The athletic training apparatus may further include a plurality of sensors, which may be adapted to sense a ball, and/or projectile, etc., and its proximity to the athletic training device.

According to one exemplary embodiment, the athletic training apparatus may further include: a user interface for interacting with the user to, e.g., but not limited to, receive selections of training routines, and/or to provide output to the user of suggestions, analysis, and/or results of training efforts.

According to one exemplary embodiment, the athletic training apparatus may further include: at least one processor; and at least one memory coupled to said processor, wherein said at least one processor is adapted to save and/or retrieve said training routines from said at least one memory.

According to one exemplary embodiment, the athletic training apparatus may include: wherein said robot is adapted to move said goal with respect a fixed position of a user.

According to one exemplary embodiment, the athletic training apparatus may include: wherein said goal comprises at least one of: a basketball goal; a soccer goal; a hockey goal; a field hockey goal; a field goal; a lacrosse goal; an intermediary goal; or a target.

According to one exemplary embodiment, the athletic training apparatus may include: wherein said user interface comprises at least one of: a mobile device coupled to said robot; a wireless device coupled to said robot; a computing device coupled to said robot; a communications device coupled to said robot; a tablet device coupled to said robot; a telephone device coupled to said robot; a personal digital assistant-based device coupled to said robot; a mobile phone-based device coupled to said robot; a smartphone-based device coupled to said robot; a tablet-based device coupled to said robot; or a touchscreen-based device coupled to said robot.

According to one exemplary embodiment, the athletic training apparatus may include: wherein said user interface comprises at least one of: a web browser-based application program; an app; an applet; a cloud-based application; a social-media enabled application; or an application program.

According to one exemplary embodiment the athletic training apparatus may be adapted for medical or other training use, wherein said athletic training apparatus may be used to establish a baseline for a patient's hand-eye coordination skills and may also be used to improve them.

According to an exemplary embodiment, a system may capture a baseline, and detect and track cognitive development, tracking the eye-hand coordination development of the athlete, and tracking and aiding in developing muscle memory as compared to the baseline measurements, may analyze the user's skills development, tracking development of the athlete over time, e.g., at 6 years, 12 years, etc., tracking what affects development, positively and negatively, capturing e.g., diseases and effects of injury on development, analyzing to identify raw ability vs. trained ability, evaluating traits and evaluating for performance out of a normal assessment area. The system may include an expert system, which may iteratively improve by analyzing training that yields improved results, and tailoring training for other users based on the observed successes.

According to another exemplary embodiment, robotic sports interactions may be provided, where a human may compete against a robotic machine, or on a robotically controlled platform, etc.

A personified sporting goal apparatus can include: at least one sporting goal device, wherein said at least one sporting goal device comprises: at least one processor; at least one memory coupled to said at least one processor; at least one of at least one input or at least one output device coupled to said at least one processor; at least one sporting goal; at least one personified feature, attribute, or movement; and at least one user interface coupled to said sporting goal device, wherein said user interface comprises at least one of: a display device, at least one input device, at least one output device, a keyboard, or a touchscreen, and wherein said at least one sporting goal device is configured to at least one of: enable at least one user to interact with said at least one sporting goal device; receive a selection of at least one sporting goal routine; or receive instructions to control said at least one sporting goal device. The device can include a robot and/or one or more displays and/or optional speech bubbles.

Further features and advantages of the invention, as well as the structure and operation of various exemplary embodiments of the invention, are described in detail below with reference to the accompanying drawings.

BRIEF DESCRIPTION OF THE DRAWINGS

The foregoing and other features and advantages of the invention will be apparent from the following, more particular description of an embodiment of the invention, as illustrated in the accompanying drawings wherein like reference numbers generally indicate identical, functionally similar, and/or structurally similar elements. The left most digits in the corresponding reference number indicate the drawing in which an element first appears.

FIG. 5 depicts an alternative exemplary top view diagram, illustrating an exemplary robot as may be coupled to goal of FIG. 1, and illustrating an exemplary rotational extent, +/−165 degrees, as well exemplary, but nonlimiting dimensions, as may be used in an exemplary embodiment of the claimed invention;

FIG. 31 depicts an exemplary embodiment of a basketball dribbling practice robot according to an exemplary embodiment;

FIGS. 32A and 32B depict exemplary embodiments of multiple basket goals according to an exemplary embodiment;

FIG. 32C depicts an exemplary embodiment of multiple basket goals in an exemplary horizontal orientation, with an example single robot to control the continuously movable goal, according to an exemplary embodiment;

FIG. 32D depicts an exemplary embodiment of multiple basket goals in an exemplary vertical orientation, with an example single robot to control the continuously movable goal, according to an exemplary embodiment;

FIG. 32E depicts an exemplary embodiment of multiple basket goals in an exemplary horizontal orientation, with an example plurality of robots to control the continuously movable goals, according to an exemplary embodiment;

FIG. 32F depicts an exemplary embodiment of multiple basket goals in an exemplary horizontal or vertical orientation, with an example single robot with a plurality of end effectors to control the continuously movable goals, according to an exemplary embodiment.

DETAILED DESCRIPTION OF EXEMPLARY EMBODIMENTS OF THE DISCLOSURE

Figure 1:
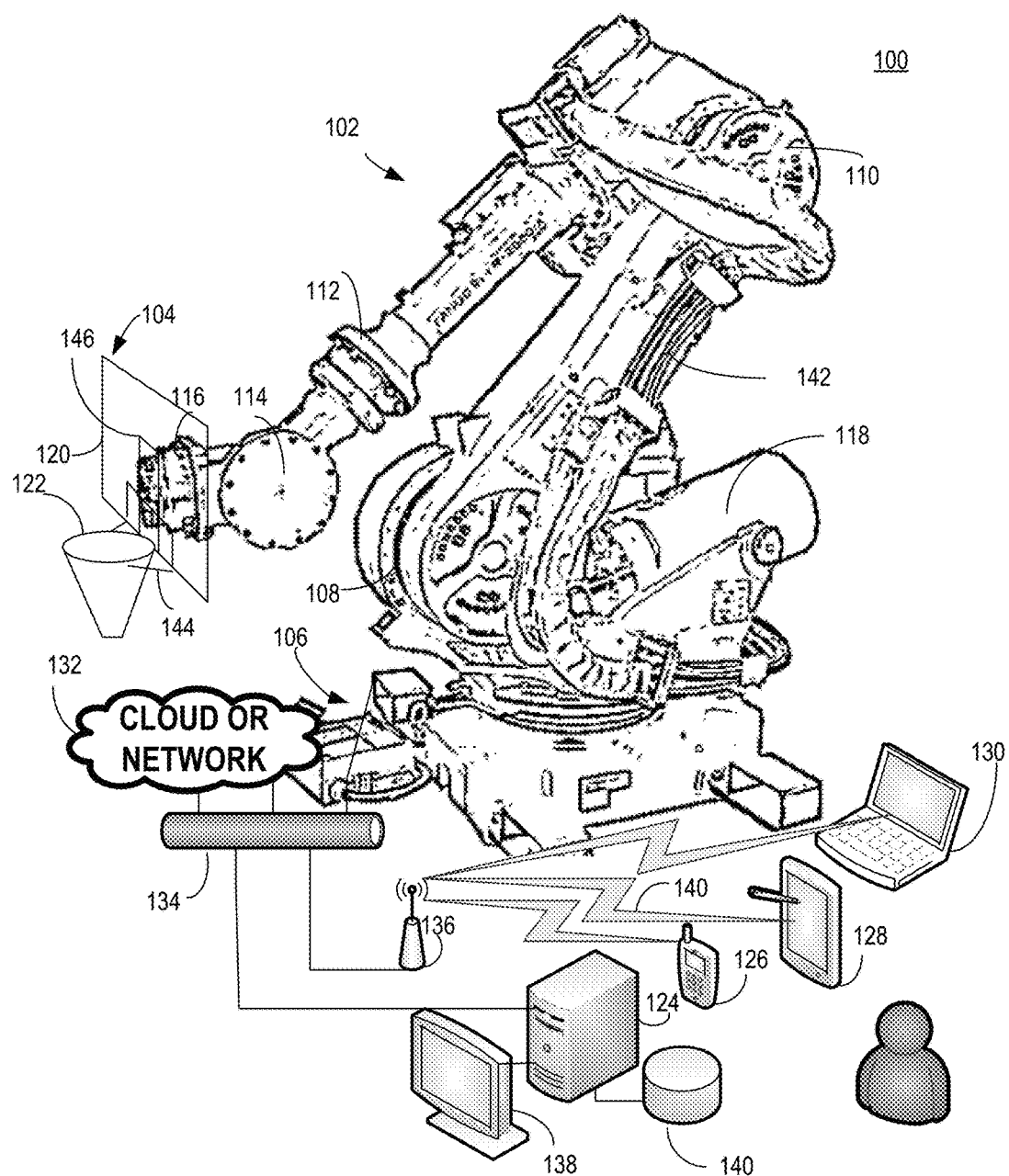
FIG. 1 depicts an exemplary diagram illustrating an exemplary robot coupled to an exemplary goal and/or an interface and/or control system, according to an exemplary embodiment of the claimed invention.

Various exemplary embodiments of the invention are discussed in detail below. While specific exemplary embodiments are discussed, it should be understood that this is done for illustration purposes only. Exemplary means example for purposes of this application, and various embodiments need not include all features as described herein. A person skilled in the relevant art will recognize that other components and configurations can be used without parting from the spirit and scope of the invention.

Introduction to Athletic Training Systems and Sporting Goals and Related Systems Example conventional training systems include, U.S. Pat. No. 5,330,175, U.S. Pat. No. D321,370, U.S. Pat. No. 3,888,023, U.S. Pat. No. 5,800,291, U.S. Pat. No. 5,890,985, U.S. Pat. No. 8,152,660, U.S. Pat. No. D539,373, U.S. Pat. No. D 510,112, U.S. Pat. No. 4,989,862, U.S. Pat. No. 6,579,197, U.S. Pat. No. 5,485,993, and US Patent Publication 2012/0142458, the contents of all of which are incorporated herein by reference in their entireties. Such systems seek to provide a simulated environment for an athlete, however none of these exemplary conventional systems achieves the goal of providing a real in game experience for an athlete training for a sport in a limited area, according to various exemplary embodiments of the present invention.

Overview of Various Exemplary Embodiments

According to one exemplary embodiment, a computer implemented apparatus, system, method and/or computer program product to provide a robotically controlled moveable backboard and hoop for athletic training. According to other exemplary embodiments, other goals than a basketball hoop and backboard may be used, coupled to an exemplary robot including goals, such as, e.g., but not limited to, ice hockey, soccer, field hockey, football, lacrosse, etc.

According to one exemplary embodiment, a moving hoop or target may allow the player to develop and practice dynamic shooting without the fatigue associated with accelerating and decelerating the player's body with each dynamic practice shot.

An exemplary embodiment of the invention may allow a player to stay in one position and practice the same dynamic eye hand coordination as if they were moving, without a lot of fatigue because the hoop is moving instead of the player. It is appreciated, according to an exemplary embodiment, that whether the player is moving or the hoop is moving it is the relationship between the two that is critical in developing dynamic eye-hand coordination.

An exemplary embodiment of the invention may allow the hoop to move in any of an exemplary 5-axis directions in relation to a stationary player just as a player can move in any 5-axis directions in relation to a stationary hoop or goal. The velocity and acceleration/deceleration of the hoop can also be modified and/or adjusted just as a player can accelerate and decelerate while shooting, according to an exemplary embodiment. Various pre-programmed and/or customized training sessions may be provided, accessed, and/or stored and/or retrieved from memory, randomized, and/or shuffled, etc., for an almost endless variety of training possibilities, according to various exemplary embodiments.

According to an exemplary embodiment, a robot capable of movement in multiple positions in a multidimensional space such as, e.g., but not limited to, at least a two dimensional, and/or a 3 dimensional (or greater) coordinate space. According to an exemplary embodiment, the robot may be coupled to the goal at an extremity of the robot. According to an exemplary embodiment, the robot may move in multiple areas and in multiple degrees of freedom by any of various well known methods including, e.g., but not limited to, rotationally, by motors, gears, armatures, and/or chains, and/or pneumatics and/or hydraulics, etc., as is well known in the art.

The system, according to an exemplary embodiment, may come with an exemplary user friendly simple pc or other computer based user interface, such as, e.g., but not limited to, a graphical user interface (GUI), where the player can direct the hoop to move in each of the exemplary 5-axes within the reach limits of the robot, according to one exemplary embodiment. The robot, according to an exemplary embodiment, can make all these movements while maintaining a constant axis of travel such as in the horizontal height of 10 feet, according to an exemplary embodiment. The speed of the hoop can be adjusted as appropriate and the movements may be repeated endlessly, according to an exemplary embodiment. Once the hoop is in motion, the player can observe the movements of the hoop and practice shooting the ball as it moves, according to an exemplary embodiment.

According to one exemplary embodiment, a FANUC 2000 IA robot, available from Intelligent Robot Solutions, FANUC Robotics America, Inc., 3900 W. Hamlin Road, Rochester Hills, Mich. 48309-3253 USA, or the like, may be used as an exemplary component of an exemplary embodiment. Further, any conventional athletic goal may be coupled to the exemplary robot by a coupler. Any of various wellknown couplers available may be used including, e.g., but not limited to, removable couplers, fixed couplers, welded direct and/or indirect connections and/or couplings, interfaces, attachment mechanisms such as, e.g., but not limited to, screws, bolts, nuts, washers, snap removable, multifunctional couplers, etc. Indeed, a given robot may be outfitted with a functional coupler capable of being coupled to any of various different types and/or styles of athletic goals, according to an exemplary embodiment. According to an exemplary embodiment, a basketball goal may be removed from a robot's removable coupler and an American football field goal post may be then coupled to the coupler to be used with the robot.

The exemplary robot mechanism, according to an exemplary embodiment, can be fixed to a floor, wall or ceiling or it can be portable such as, e.g., but not limited to, when mounted on a platform with exemplary wheels, and/or drive mechanisms, and/or support legs, and/or outriggers for stability, etc.

According to an exemplary embodiment, the robot may be capable of very precise, repeatable movements allowing for ease of repetition of training exercises.

According to an exemplary embodiment, the robot athletic training device may be capable of being programmed using any of various well know programming techniques. The robot, according to an exemplary embodiment may be coupled to any of various well-known input and/or output and/or control systems. Exemplary, but not limiting, input systems may include, e.g., but not limited to, sensors, movement sensors, location sensors, rotational sensors, etc. Exemplary, but not limiting, output systems may include, e.g., but not limited to, motors, gears, hydraulics, arms, legs, joints, pneumatics, air and/or fluid and/or gas moment systems, etc. Exemplary, but not limiting, robotic control systems may include, e.g., but not limited to, computer processor(s), computer memory(ies), computing hardware, computing software, operating systems, programming languages and/or environments, communications and networking capability, database(s), wireless and/or wired communications networking, access to internally stored exercise routines, access by network and/or Internet, and/or cloud-based exercise routines and/or programmable routines, and/or graphical user interface(s), and/or mobile and/or touch based system environments, and/or worldwide web and/or other application program environment applications, apps, or programs, etc. According to an exemplary embodiment, an exemplary device may include a robot coupled to a sporting goal device. According to an exemplary sporting device, the sporting goal device may include, e.g., but not limited to, a backboard and hoop for basketball, a goal for soccer, a goal for ice hockey, field hockey, a goal for lacrosse, etc.

According to an exemplary embodiment, a robot may include any of various well known robots available from any of various well known robotic manufacturers, such as, e.g., but not limited to, Intelligent Robot Solutions, FANUC Robotics America, Inc., 3900 W. Hamlin Road, Rochester Hills, Mich. 48309-3253 USA, etc.

According to an exemplary embodiment the athletic training system may also be used for medical purposes, that involve training patients' hand-eye coordination skills.

FIG. 1 depicts an exemplary diagram 100 illustrating an exemplary robot 102 coupled to an exemplary goal 104 and/or an interface and/or control system, according to an exemplary embodiment of the claimed invention. According to an exemplary embodiment, the robot 102 may be coupled to an sports goal 104, and/or an interface system 124-130.

According to an exemplary embodiment of the claimed invention, exemplary robot 102 may include, e.g., but not be limited to, a exemplary FANUC 2000 IA robot, according to an exemplary embodiment, coupled to an exemplary sporting goal 104. According to an exemplary embodiment, robot 102 may include one or more sub components, as shown, such as, e.g., but not limited to, a base, any of various hydraulics 118, and/or pneumatic and/or control cables 142, and/or any of various joints and/or gears 108, 110, 112, 114, and/or 116. According to an exemplary embodiment, the robot may rotate and/or move in multiple degrees of freedom, programmatically via any of various well-known programming routines and/or programs as may be loaded, stored and/or retrieved from and to a control system 106 for the robot 102. According to an exemplary, but not limiting embodiment, control system 106 of robot 102 may include an interface to any of various exemplary user accessible devices 124, 126, 128, 130, such as, e.g., but not limited to, a computing device 124 and/or storage and/or database 140, and/or output device 138 and/or input device (not shown) such as, e.g., not limited to, a touchscreen on display 138, a keyboard (not shown), tablet, and/or pen-based and/or stylus-based, and/or mouse (not shown), and/or any of various other well-known such input and/or output (110) devices, smart phone and/or other telephony and/or portable device 126, tablet 128, and/or pointing device such as, e.g., pen and/or stylus (shown but not labeled), and/or notebook and/or laptop 130, according to various exemplary embodiments, etc. A user, (shown but not labeled) may interact with any of the various exemplary interface devices to program, and/or access training routines, which may be made accessible via user interfaces on any of the devices, which as shown in an exemplary embodiment, may be coupled in exemplary wired fashion over coupling devices 134 such as, e.g., but not limited to, wire(s), cable(s), networking hub(s), router(s), gateway(s), bridge(s), and/or wirelessly via access point(s) 136 and/or other well-known communications networks and/or topologies via communications links 140 in the case of wireless communication and/or other means via wired communication, locally at 106, and/or remotely via a network 132, which may include any of various physical devices corresponding to a logical network which may include reference generally in aggregate as a cloud, and/or network, and/or intra, extra, or internet, such as, e.g., the global Internet.

A goal 104, according to an exemplary embodiment, may include a basketball backboard 120 and hoop 122, according to one exemplary embodiment. In an exemplary embodiment, the hoop 122 may be coupled to the exemplary backboard 120 by one or more couplers 144, which may directly, and/or indirectly, couple and/or connect, the hoop 122 to the backboard 120. As shown, the backboard 120 may be further coupled to the robot 102 by a coupler 146 as may couple, according to an exemplary embodiment the backboard 120 and/or hoop 122 to an end piece 116 of robot 102.

Figure 2:
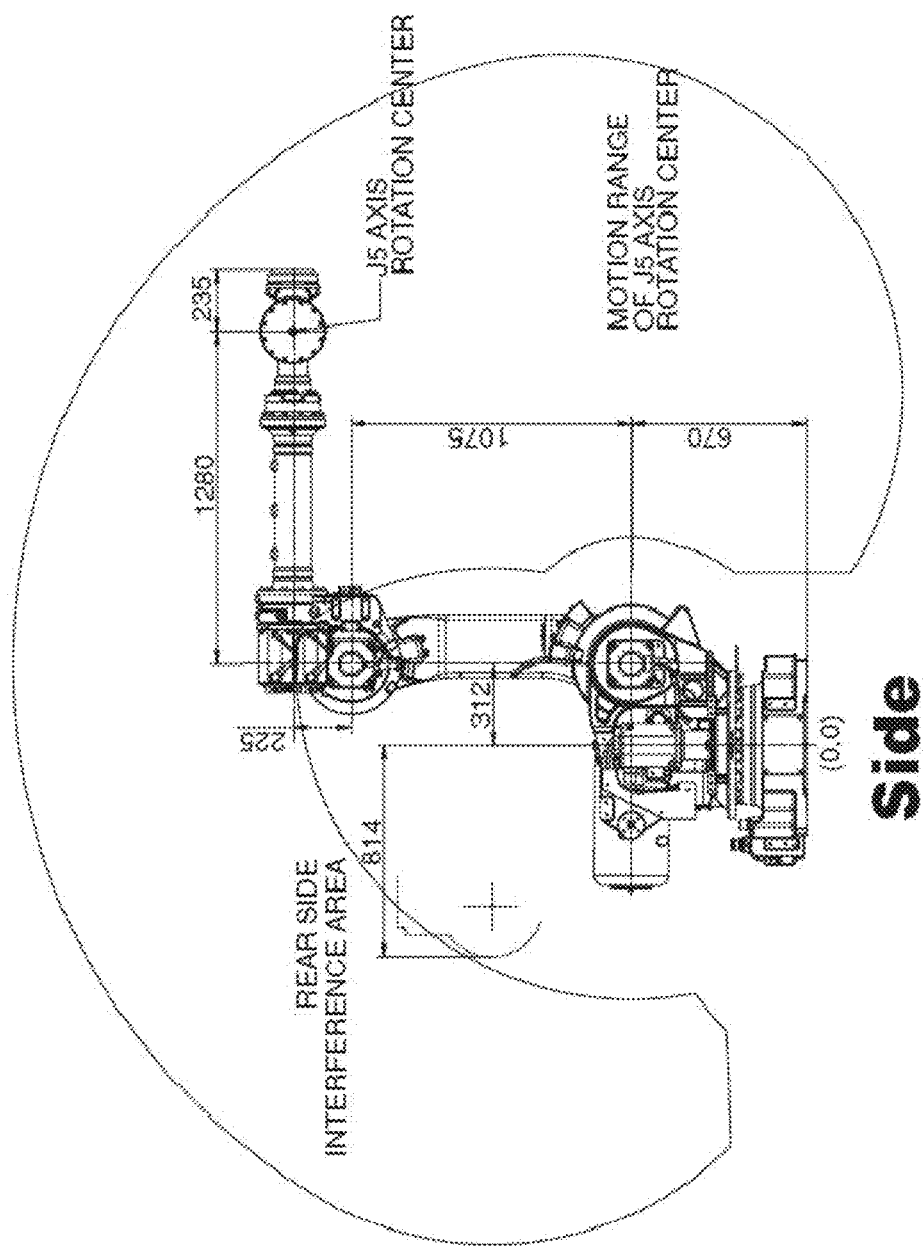
FIG. 2 depicts exemplary side view diagram, illustrating an exemplary robot of FIG. 1, and illustrating an exemplary rear side interference area, J5 axis rotation center, and motion range of J5 Axis rotation center, along with exemplary, but nonlimiting dimensions, as may be used in an exemplary embodiment of the claimed invention.

FIG. 2 depicts exemplary side view diagram 200, illustrating an exemplary robot 102 as may be coupled to goal 104 of FIG. 1, and illustrating an exemplary rear side interference area, J5 axis rotation center, and motion range of J5 Axis rotation center, along with exemplary, but nonlimiting dimensions, as may be used in an exemplary embodiment of the claimed invention.

Figure 3:
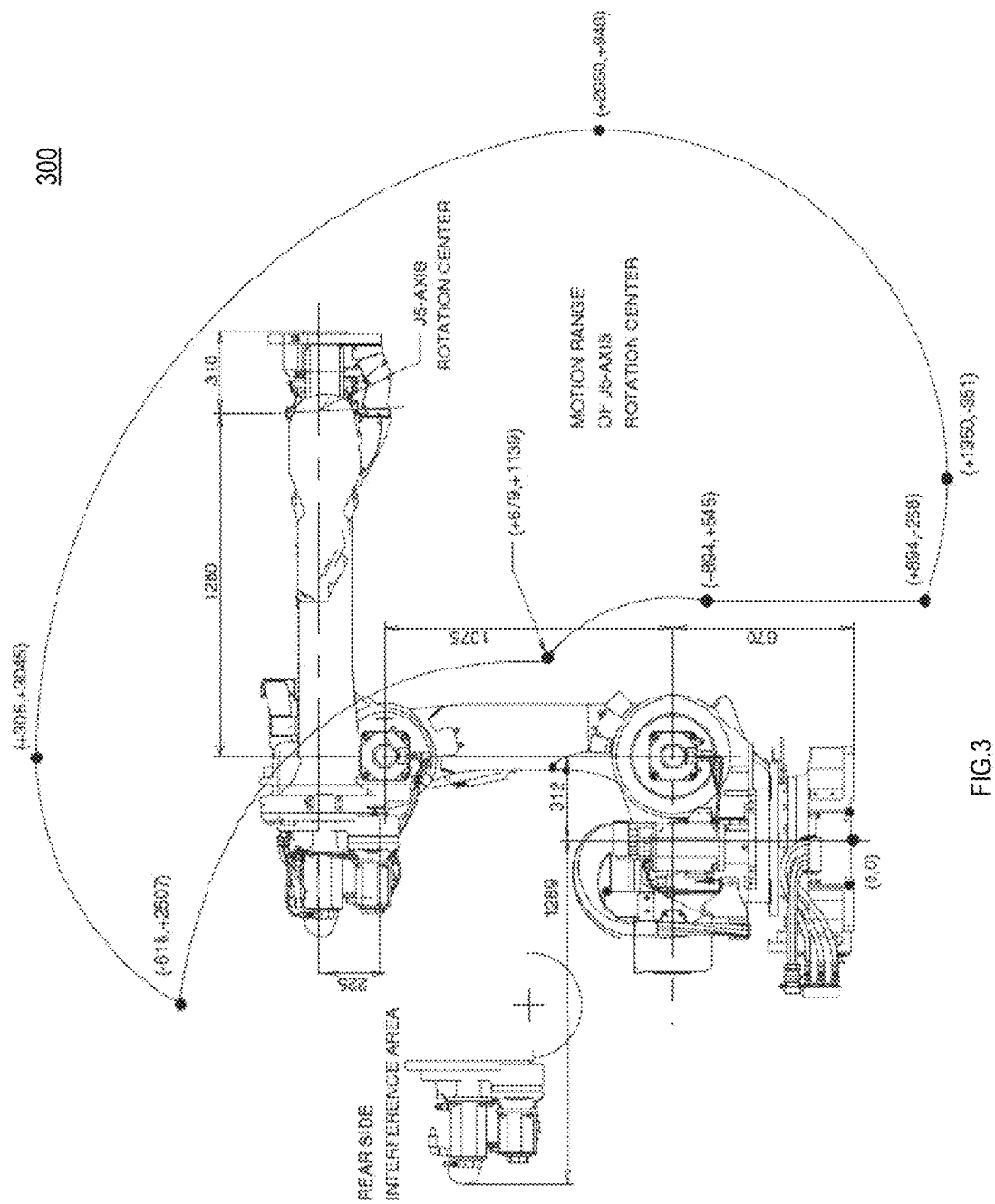
FIG. 3 depicts another alternative exemplary side view diagram, illustrating an exemplary robot as may be coupled to goal of FIG. 1, and illustrating an exemplary rear side interference area, J5 axis rotation center, and motion range of J5 Axis rotation center, along with exemplary, but nonlimiting dimensions, as may be used in an exemplary embodiment of the claimed invention.

FIG. 3 depicts another alternative exemplary side view diagram 300, illustrating an exemplary robot 102 as may be coupled to goal 104 of FIG. 1, and illustrating an exemplary rear side interference area, J5 axis rotation center, and motion range of J5 Axis rotation center, along with exemplary, but nonlimiting dimensions, as may be used in an exemplary embodiment of the claimed invention.

Figure 4:
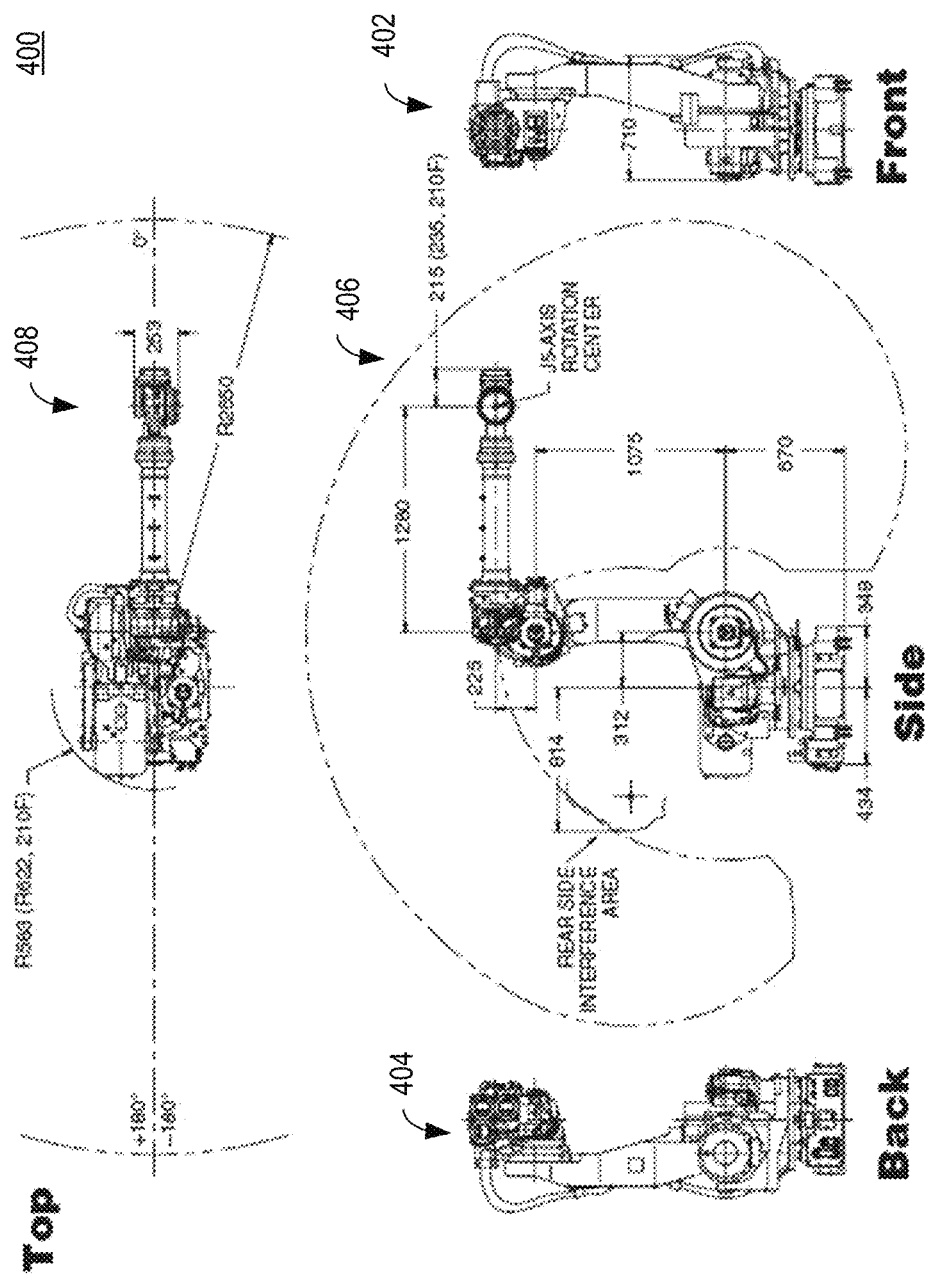
FIG. 4 depicts diagram including an alternative exemplary side view diagram, exemplary front view, exemplary back view, and exemplary top view, illustrating an exemplary robot as may be coupled to goal of FIG. 1, and illustrating an exemplary rear side interference area, J5 axis rotation center, and motion range of J5 Axis rotation center, along with exemplary, but nonlimiting dimensions, as may be used in an exemplary embodiment of the claimed invention.

FIG. 4 depicts diagram 400 including an alternative exemplary side view diagram 406, exemplary front view 402, exemplary back view 404, and exemplary top view 408, illustrating an exemplary robot 102 as may be coupled to goal 104 of FIG. 1, and illustrating an exemplary rear side interference area, J5 axis rotation center, and motion range of J5 Axis rotation center, along with exemplary, but nonlimiting dimensions, as may be used in an exemplary embodiment of the claimed invention.

FIG. 5 depicts an alternative exemplary top view diagram 500, illustrating an exemplary robot 102 as may be coupled to goal 104 of FIG. 1, and illustrating an exemplary rotational extent, +/−165 degrees, as well exemplary, but nonlimiting dimensions, as may be used in an exemplary embodiment of the claimed invention.

Figure 6B:
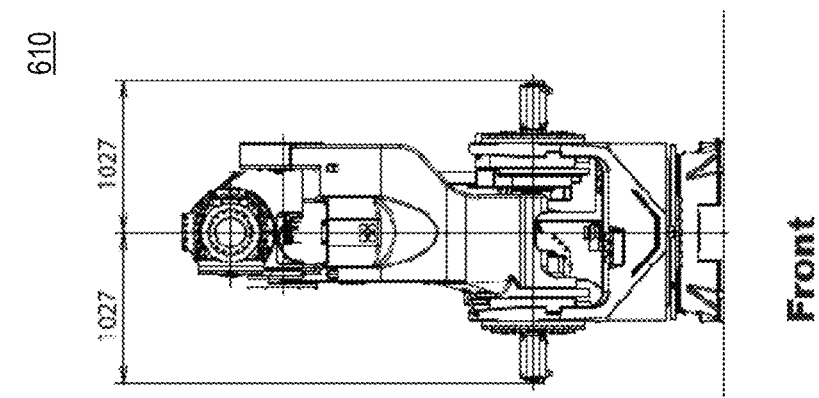
FIG. 6B depicts an alternative exemplary front view diagram, illustrating an exemplary robot as may be coupled to goal of FIG. 1, and illustrating exemplary, but nonlimiting dimensions, as may be used in an exemplary embodiment of the claimed invention.
Figure 6A:
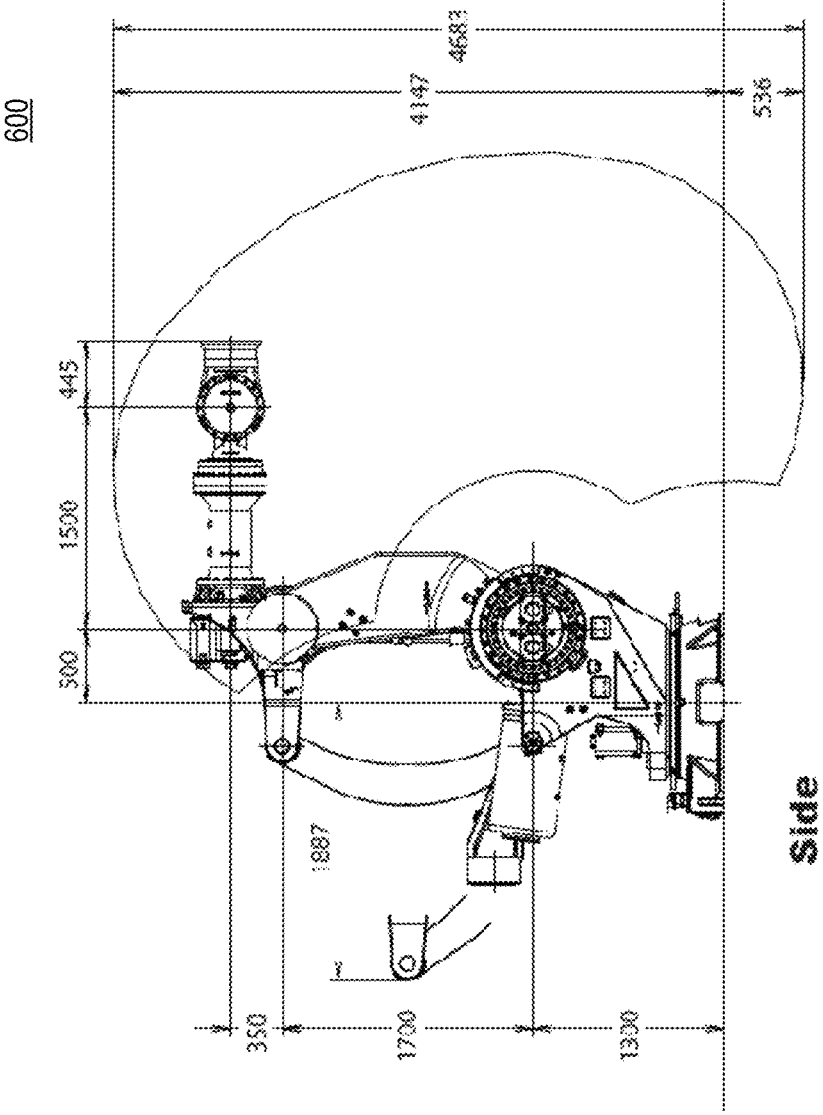
FIG. 6A depicts an alternative exemplary side view diagram, illustrating an exemplary robot as may be coupled to goal of FIG. 1, and illustrating an exemplary rotational range, as well exemplary, but nonlimiting dimensions, as may be used in an exemplary embodiment of the claimed invention.

FIG. 6A depicts an alternative exemplary side view diagram 600, illustrating an exemplary robot 102 as may be coupled to goal 104 of FIG. 1, and illustrating an exemplary rotational range, as well exemplary, but nonlimiting dimensions, as may be used in an exemplary embodiment of the claimed invention.

FIG. 6B depicts an alternative exemplary front view diagram 610, illustrating an exemplary robot 102 as may be coupled to goal 104 of FIG. 1, and illustrating exemplary, but nonlimiting dimensions, as may be used in an exemplary embodiment of the claimed invention.

Figure 7:
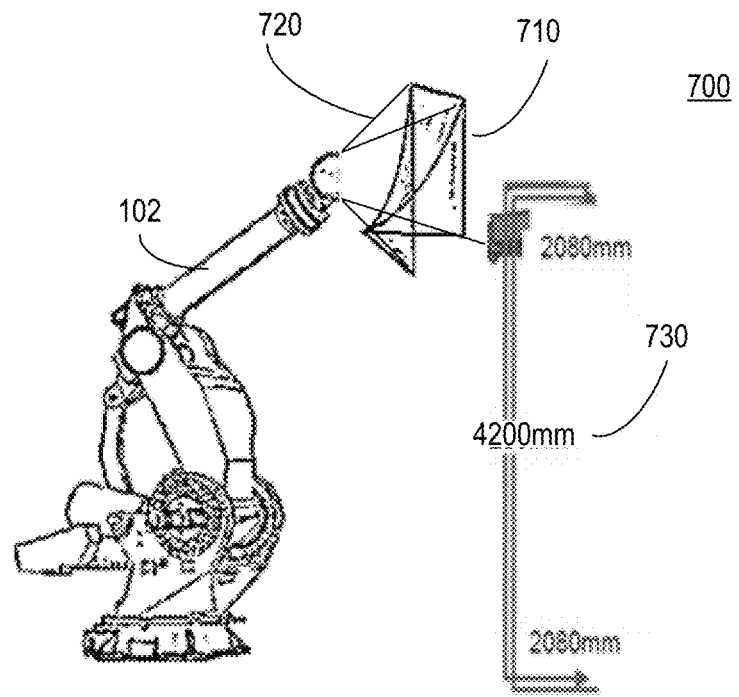
FIG. 7 depicts an alternative exemplary diagram, illustrating an exemplary robot as may be coupled to goal of FIG. 1, in this case, an exemplary lacrosse goal, which may be coupled to robot by one or more exemplary couplers, such as, e.g., but not limited to, removably couplable, or permanently coupled, members, such as, e.g., but not limited to, resilient and/or metal members, etc., and illustrating an exemplary precise vertical range of exemplary, but nonlimiting dimensions, in an exemplary embodiment, as may be used in an exemplary embodiment of the claimed invention.

FIG. 7 depicts an alternative exemplary diagram 600, illustrating an exemplary robot 102 as may be coupled to goal 104 of FIG. 1, in this case, an exemplary lacrosse goal 710, which may be coupled to robot 102 by one or more exemplary couplers 720, such as, e.g., but not limited to, removably couplable, or permanently coupled, members, such as, e.g., but not limited to, resilient and/or metal members 720 etc., and illustrating an exemplary precise vertical range of exemplary, but nonlimiting dimensions, of approximately, about 4200 mm 730, in an exemplary embodiment, as may be used in an exemplary embodiment of the claimed invention.

Figure 8:
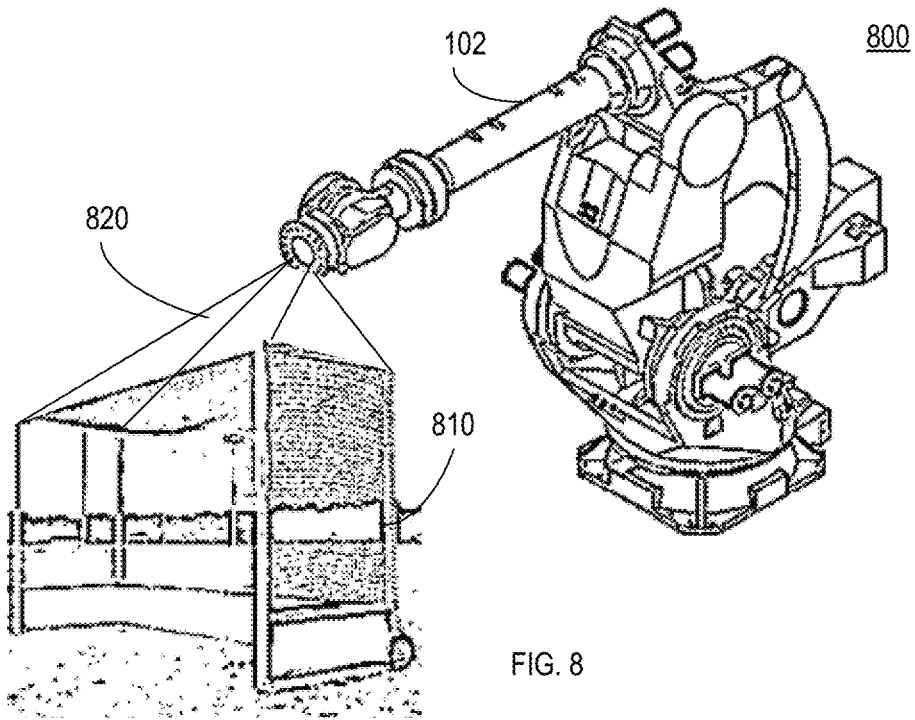
FIG. 8 depicts an alternative exemplary diagram, illustrating an exemplary robot as may be coupled to goal of FIG. 1, in this case, an exemplary field hockey goal, which may be coupled to robot by one or more exemplary couplers, such as, e.g., but not limited to, removably couplable, or permanently coupled, members, such as, e.g., but not limited to, resilient and/or metal members, etc., and illustrating an exemplary, but nonlimiting orientation and dimensions, as may be used in an exemplary embodiment of the claimed invention.

FIG. 8 depicts an alternative exemplary diagram 800, illustrating an exemplary robot 102 as may be coupled to goal 104 of FIG. 1, in this case, an exemplary field hockey goal 810, which may be coupled to robot 102 by one or more exemplary couplers 820, such as, e.g., but not limited to, removably couplable, or permanently coupled, members, such as, e.g., but not limited to, resilient and/or metal members 820 etc., and illustrating an exemplary, but nonlimiting orientation and dimensions, as may be used in an exemplary embodiment of the claimed invention.

FIG. 7 depicts an alternative exemplary diagram 600, illustrating an exemplary robot 102 as may be coupled to goal 104 of FIG. 1, in this case, an exemplary lacrosse goal 710, which may be coupled to robot 102 by one or more exemplary couplers 720, such as, e.g., but not limited to, removably couplable, or permanently coupled, members, such as, e.g., but not limited to, resilient and/or metal members 720 etc., and illustrating an exemplary precise vertical range of exemplary, but nonlimiting dimensions, of approximately, about 4200 mm 730, in an exemplary embodiment, as may be used in an exemplary embodiment of the claimed invention.

Figure 9:
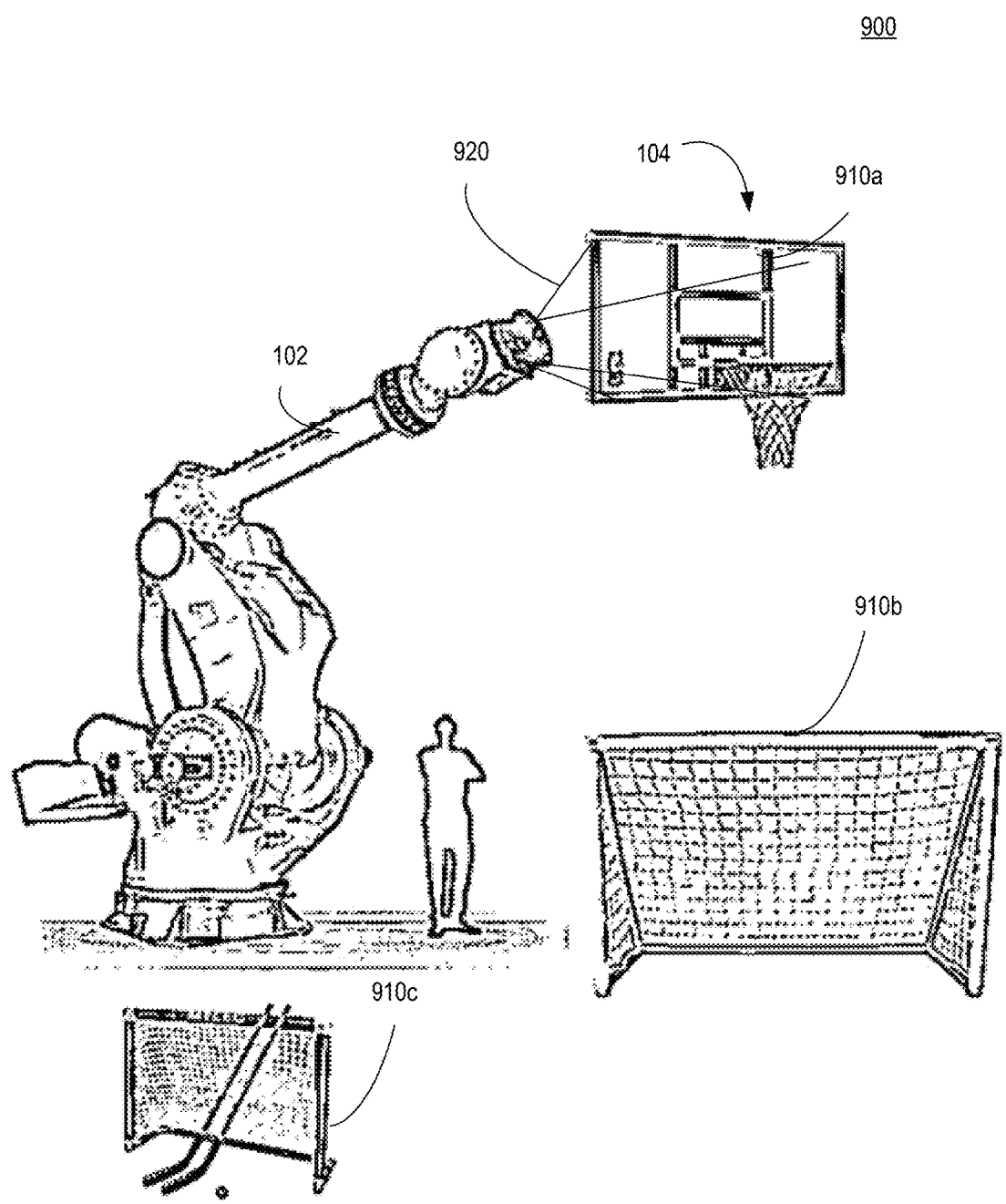
FIG. 9 depicts an alternative exemplary diagram, illustrating an exemplary robot as may be coupled to one of various multifunction goals of FIG. 1, in this case, one of various multifunction goals, such as, basketball backboard and hoop, or the exemplary field hockey goal of FIG. 8, or the lacrosse goal of FIG. 7, or exemplary soccer goal, and/or ice hockey goal, and/or other goal (not shown), any of such exemplary goals, which may be coupled to robot by one or more exemplary couplers, in an exemplary embodiment including indirectly, and/or directly, couplers and/or connectors, such as, e.g., but not limited to, removably couplable, or permanently coupled, members, such as, e.g., but not limited to, resilient and/or metal members, etc., and illustrating an exemplary, but nonlimiting orientation and dimensions, as may be used in an exemplary embodiment of the claimed invention.

FIG. 9 depicts an alternative exemplary diagram 900, illustrating an exemplary robot 102 as may be coupled to one of various multifunction goals 104 of FIG. 1, in this case, one of various multifunction goals 104, such as, basketball backboard and hoop 910a, or the exemplary field hockey goal 810 of FIG. 8, or the lacrosse goal 710 of FIG. 7, or exemplary soccer goal 910b, and/or ice hockey goal 910c, and/or other goal (not shown), any of such exemplary goals, which may be coupled to robot 102 by one or more exemplary couplers 920, in an exemplary embodiment including indirectly, and/or directly, couplers and/or connectors, such as, e.g., but not limited to, removably couplable, or permanently coupled, members, such as, e.g., but not limited to, resilient and/or metal members 920 etc., and illustrating an exemplary, but nonlimiting orientation and dimensions, as may be used in an exemplary embodiment of the claimed invention.

Figure 10:
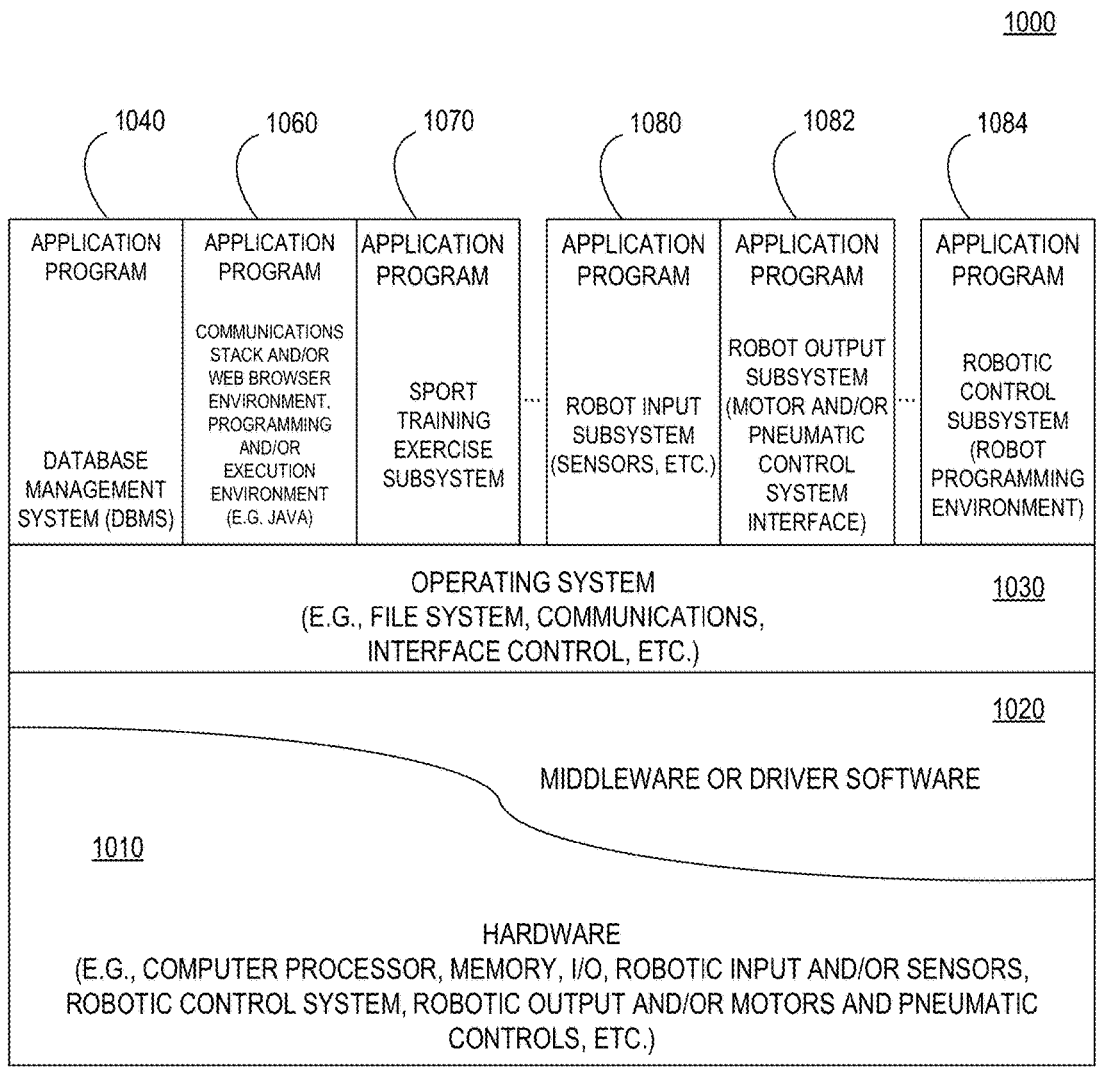
FIG. 10 depicts a diagram illustrating an exemplary system architecture diagram illustrating an exemplary hardware platform, exemplary middleware and/or driver software, exemplary operating system, and various exemplary applications, according to an exemplary embodiment.

Referring back to FIG. 1, which depicts an exemplary embodiment of diagram 100 of an exemplary system illustrating an exemplary network environment including computing devices 124-130 coupled to athletic training robot 102 and goal 104, according to an exemplary embodiment of the present invention. The high-level system block diagram 100 may include, in an exemplary embodiment, users interacting with browsers (not shown) on client user interface devices 124-130 (collectively 102), respectively. A system hardware and software architecture is described further with reference to FIG. 10. FIG. 10 references various exemplary applications as may be included in certain exemplary embodiments.

FIG. 10 depicts diagram 1000 illustrating an exemplary system architecture diagram illustrating an exemplary hardware platform 1010, exemplary middleware and/or driver software 1020, exemplary operating system 1030, and various exemplary applications 1040-1084, according to an exemplary embodiment.

In an exemplary embodiment application program 1040 may include an exemplary database management system (DBMS) as may include any of various well known database platforms, in an exemplary embodiment.

In an exemplary embodiment application program 1060 may include an exemplary communications stack and/or web browser environment and/or programming and/or execution environments, such as, e.g., but not limited to JAVA, etc., as may include any of various well known application program platforms, in an exemplary embodiment.

In an exemplary embodiment application program 1070 may include an exemplary sport or athletic training exercise subsystem program, such as, e.g., but not limited to applications and/or applets and/or web-based applications, etc., as may include a graphic user interface (GUI) for user interaction with the robot controlled goal, according to an exemplary embodiment.

In an exemplary embodiment application program 1080 may include an exemplary sport robot, exemplary input subsystem program, such as, e.g., but not limited to applications and/or applets and/or web-based applications, etc., as may include, e.g., but not limited to, subsystems for handling any of various robotic sensor and/or other inputs for controlling input interaction from the robot controlled goal, according to an exemplary embodiment.

In an exemplary embodiment application program 1082 may include an exemplary sport robot, exemplary output subsystem program, such as, e.g., but not limited to applications and/or applets and/or web-based applications, etc., as may include, e.g., but not limited to, subsystems for handling any of various robotic motor and/or other outputs such as, e.g., pneumatic, air and/or fluid pressure systems and/or control system interface, for controlling output interactions to the robot controlled goal, according to an exemplary embodiment.

In an exemplary embodiment application program 1084 may include an exemplary sport robot, exemplary robot control subsystem program, such as, e.g., but not limited to applications and/or applets and/or web-based applications, etc., as may include, e.g., but not limited to, subsystems for handling any of various robotic control and/or programming and/or robotic running an maintenance environments such as, e.g., but not limited to, various well known robot control software application system environments such as, e.g., but not limited to, industrial robot programming languages, any exemplary FANUC robot control and programming languages, Labview, Robot C, Lego NXT/G, EV3 Labview Programming Environment, etc., and other graphical robot programming environments, etc., according to various exemplary embodiments. According to an exemplary embodiment, a user may program for an x, y, and z direction, a velocity and/or distance of movement of the robot over an exemplary five (5) degrees of freedom of movement. Various pre-programmed scenarios may be stored, and/or accessible, in an exemplary embodiment. Where an exemplary plurality of training programs have been stored, the user may select from one of the stored scenarios, may be assigned a scenario, may be randomly assigned, and/or may be shuffled, etc., according to an exemplary embodiment.

Figure 11:
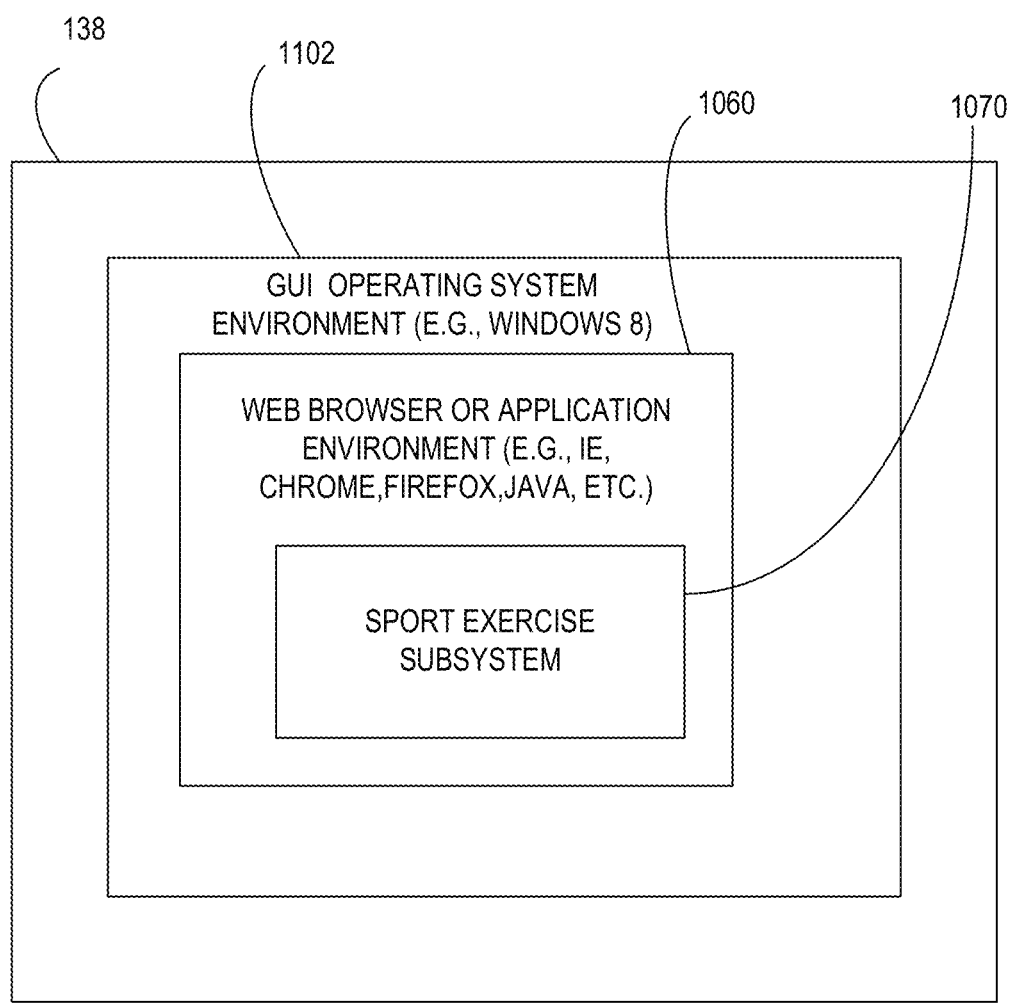
FIG. 11 depicts a diagram illustrating an exemplary display depicting an exemplary graphical user interface operating system environment (such as, e.g., but not limited to, Windows 8, etc.), a web browser and/or application environment (such as, e.g., but not limited to, MSFT Internet Explorer, Google Chrome, Mozilla FireFox, JAVA, FLASH, etc., and/or an application and/or applet, and/or program sport exercise interface subsystem application, according to an exemplary embodiment.

FIG. 11 depicts diagram 1100 illustrating an exemplary display 138 depicting an exemplary graphical user interface operating system environment 1102 (such as, e.g., but not limited to, Windows 8, etc.), a web browser and/or application environment (such as, e.g., but not limited to, Microsoft Internet Explorer, Google Chrome, Mozilla, FireFox, JAVA, FLASH, etc., and/or an application and/or applet, and/or program sport exercise interface subsystem application 1070, according to an exemplary embodiment.

Figure 12:
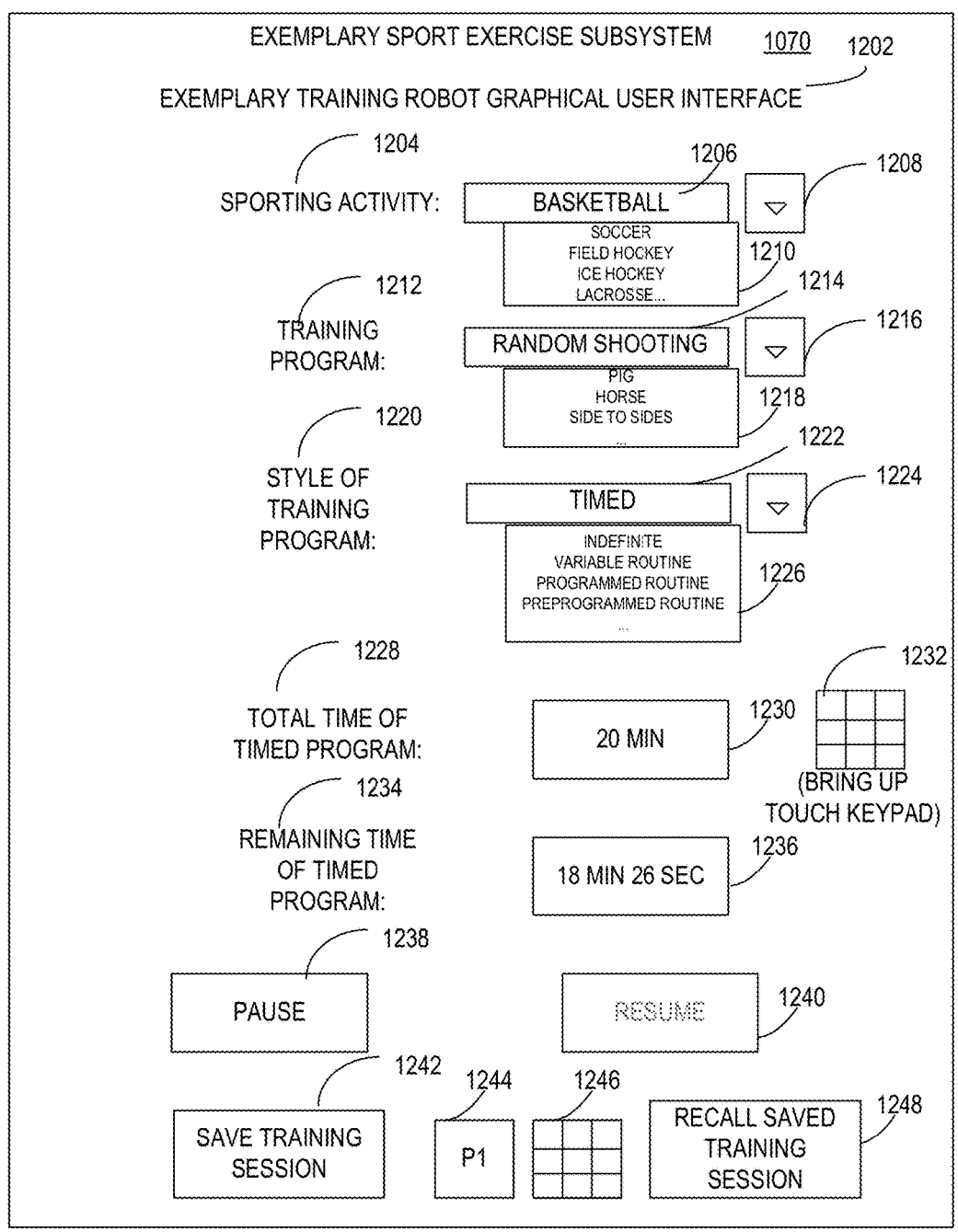
FIG. 12 depicts a diagram of an exemplary screenshot of an exemplary sport exercise subsystem application, including an exemplary training robot graphical user interface (GUI) interface to robot and goal system of FIG. 1, illustrating exemplary prompts, and exemplary input fields, as well as, exemplary pull down buttons, and keypad selectors, as well as, exemplary pause resume buttons, as well as exemplary save training session, and/or recall saved training session exemplary buttons as may be provided in an exemplary user interface display of one exemplary embodiment.

FIG. 12 depicts diagram 1200 of an exemplary screenshot 1200 of an exemplary sport exercise subsystem 1070 application, including an exemplary training robot graphical user interface (GUI) 1202 interface to robot 102 and goal 104 system 100 of FIG. 1, illustrating exemplary prompts 1204, 1212, 1220, 1228, 1234 and exemplary input fields 1206, 1214, 1222, 1230, 1236, and 1244 as well as, exemplary pull down buttons 1208, 1216, 1224, and keypad selectors 1232, 1246, as well as, exemplary pause resume buttons, as well as exemplary save training session and/or recall saved training session exemplary buttons as may be provided in an exemplary display of one exemplary embodiment.

In one embodiment an application program may include a browser. A browser can be, e.g., but not limited to, one or more application software programs executing on computer workstations or other computer processor based devices 124-130 (including mobile devices such as, e.g., but not limited to, communication devices, phones, smartphones, tablets, and/or computer tablets), which may be coupled via a network 132 (in wireline and/or wireless fashion) to other devices, as shown, in an exemplary embodiment. Workstations 124-130 can be coupled via a network 132 such as, e.g., but not limited to, an internet, and intranet, or another type of network. In an exemplary embodiment network 132 may include the global Internet. Network 132 may provide access for client devices 124-130 to gain access to, e.g., but not limited to, one or more application servers 111a, 111b (collectively 111, not shown), such as, e.g., but not limited to, a database management system (DBMS) as may be represented by exemplary database 140. Although a client server topology is discussed any of various other well-known types of communications topologies may also be used such as, e.g., but not limited to, point-to-point, peer-to-peer, cloud-based, software as a service (SAAS), browser-based, hierarchical, distributed, and/or centralized, etc. The application server 111 can manage one or more databases (collectively 140). In an exemplary embodiment, the application server 111 can access an exemplary database(s) 140 having a plurality of data records, where in an exemplary embodiment, each data record may have one or more fields, etc. It will be apparent to those skilled in the art, that each database 140 can be part of a larger database, or could be broken into a plurality of separate subdatabases. In an exemplary embodiment of the present invention, search results can include a plurality of records obtained from the database 140 that meet search criteria included in a search query. Network 132 may be coupled to any of various well-known components such as, e.g., but not limited to, one or more load balancing devices or firewall devices 107 (not shown), web server(s) 109 (not shown), application server(s) 111 (not shown), routers, gateways, physical layer devices, data link layer devices, and/or network layer devices, etc. (not shown).

As illustrated, web servers 109 and application servers 111 may be coupled to one another via one or more network(s) 132. Although network 132, in an exemplary embodiment, may be downstream of load balancing devices 105 (not shown), it is also possible to have a network upstream of load balancing devices 105, coupling, e.g., but not limited to, application server(s) 111, web server(s) 109, and/or database(s) 140, as well as other client or other server devices (not shown), local and/or remote from the depicted exemplary devices, etc. Exemplary client devices 124-130 may be thought of as downstream over an exemplary network(s) 132 from the server devices, but could easily be elsewhere in the network topology, e.g., inside, or outside a firewall. It is also important to note that network 132 is represented in cloud metaphor schematic, but various well-known network devices including various well-known star-based, star wired ring, bus-based 134, or other well-known network topologies may also be represented by exemplary network(s) 132.

A user interacting with a browser on workstation 124-130 can access the database 140, in an exemplary embodiment by traversing several intervening networks using well known communications protocols such as, e.g., but not limited to, transmission control protocol/internet protocol (TCP/IP). Specifically, in an exemplary embodiment, the workstation 124-130 can be coupled via exemplary network(s) 132 including, e.g., but not limited to, a public and/or private network, and/or the global Internet to any of various exemplary website system(s), in this exemplary case, web server(s) 109, which may include any of various hosting systems such as, e.g., but not limited to, a domain system, a domain name server (DNS), a domain controller system, etc. Website or webserver system 109 in an exemplary embodiment. The website system 109 can include, in an exemplary embodiment, an exemplary firewall coupled to, or in addition to, or integrated with, a load balancer 105 (which could alternatively run on a general-purpose computer such as, e.g., web server 109, etc. Load balancer 105 can be coupled to an exemplary web server 109. Web servers 109 can be mesh coupled to one or more application servers 111, via hardware and/or software system solutions, according to an exemplary embodiment, or via another network 132 (not shown). Each server 138, 109, 111 may include, e.g., but not limited to, or be coupled to, one or more database(s) 140. Web server(s) 109 in an exemplary embodiment, can perform load balancing functions by transferring user application requests/queries to one or more of the application servers 111. Results of the exemplary requests and/or queries from database 140 can be transferred from application servers 111 through web servers 109 through the network 132 to workstation 126-130.

An athletic training application program, and/or web-based and/or JAVA-based applet, and/or portal application program and/or links to the portal, may be integrated and/or embedded into other well-known collaborative, and/or social networking environments or applications such as, e.g., but not limited to, web-template based, hypertext markup language (HTML), and/or mobile OS application formats (e.g., iOS, and/or Android, and/or Windows 8), etc., and/or Facebook, LinkedIn, LotusLive, Microsoft Exchange/Sharepoint, GoogleTalk, GoogleVoice, Skype, Facetime, Google+, and/or video teleconferencing, Voxeo, SalesForce.com, CRM systems, etc., and/or other network environments, social media environments, communications environments, and/or collaborative environments, etc.

Any illustration of exemplary fixed images, and/or exemplary arrangements of the exemplary portal is merely exemplary, but nonlimiting, as video means, audio means, and/or a combination of audio/video streams and/or other content may also be used to enable efficient user interaction, according to various exemplary embodiments.

Figure 13:
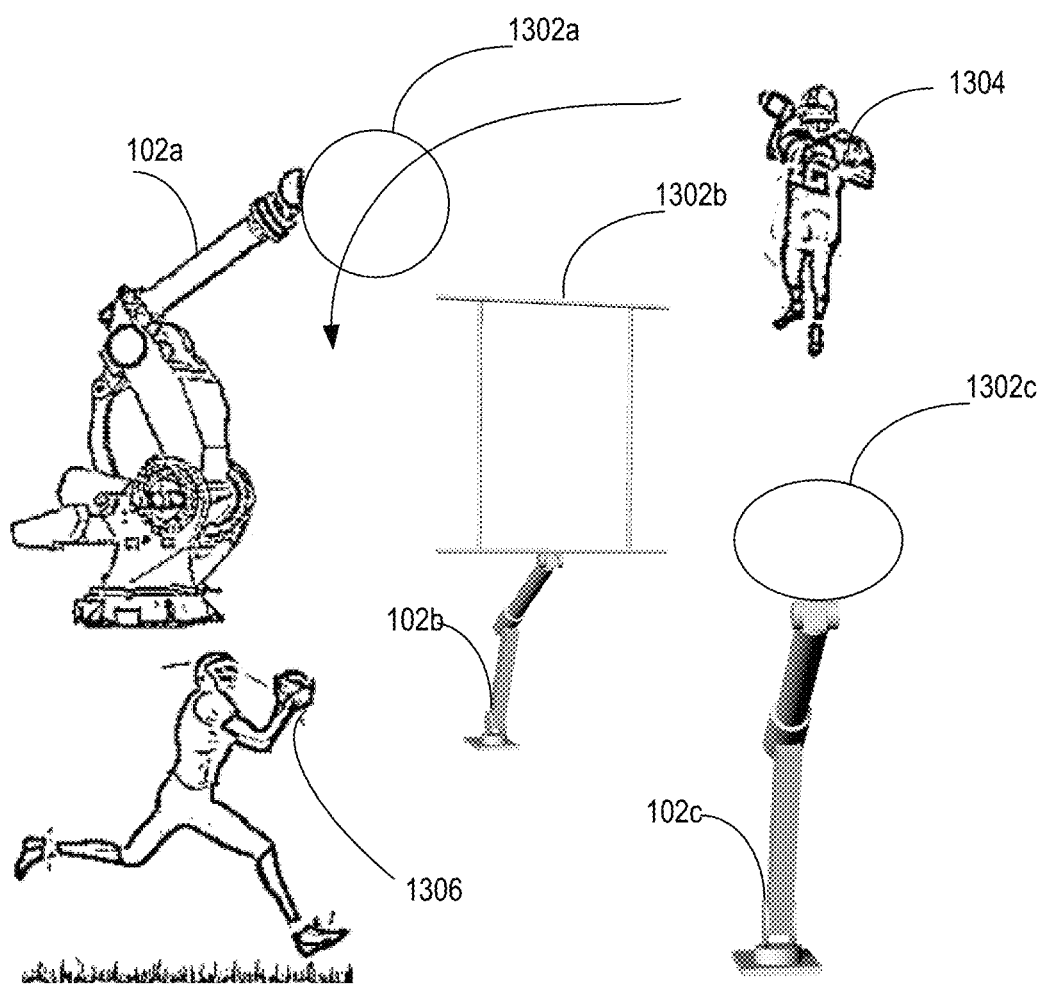
FIG. 13 depicts a diagram illustrating an exemplary embodiment of an intermediary goal coupled to the exemplary athletic training system depicted in FIG. 1, wherein the user throws, for example, a football and/or a baseball through the goal on route to the balls final destination, according to an exemplary embodiment.

FIG. 13 depicts an exemplary diagram 1300 illustrating an exemplary embodiment of an intermediary goal 1302, which may be coupled to an exemplary robot 102. According to an exemplary, but nonlimiting embodiment, the illustration shows a user 1304 throwing a football through the intermediary goal 1302 (collectively referring to any of various exemplary illustrated intermediate goals including, e.g., but not limited to, a substantially circular intermediate target 1302a, a polygon, such as, e.g., but not limited to, a triangle, an isosceles, equilateral, right and/or scalar, and/or substantially rectangular, quadrilateral and/or parallelogram, and/or square, or rhombus, or the like shaped, intermediate goal 1302b, and/or an oval and/or other shaped such as, e.g., but not limited to, other polygon shaped intermediate target 1302c, according to exemplary, nonlimiting example embodiments) to a final target in this case person 1306. The use of an intermediate target 1302a, 1302b, 1302c (collectively "1302") (coupled to an exemplary robot 102a, 102b, 102c, respectively) may serve to assist the thrower in developing muscle memory, and from learning through the repeatability of the activity. According to one exemplary embodiment, the intermediate target 1302 may be coupled to the robot 102 and may be controllable by a coach's instructions, or preprogrammed routine to direct the thrower, not only to reach a final goal 1306, but to make the ball follow a desired path through the intermediate goal 1302. Exemplary intermediate goals can be used, e.g., but not limited to, for football, basketball, golf, baseball, soccer, hockey, etc., FRISBEE flying disc golf and/or ultimate, etc.

Figure 14:
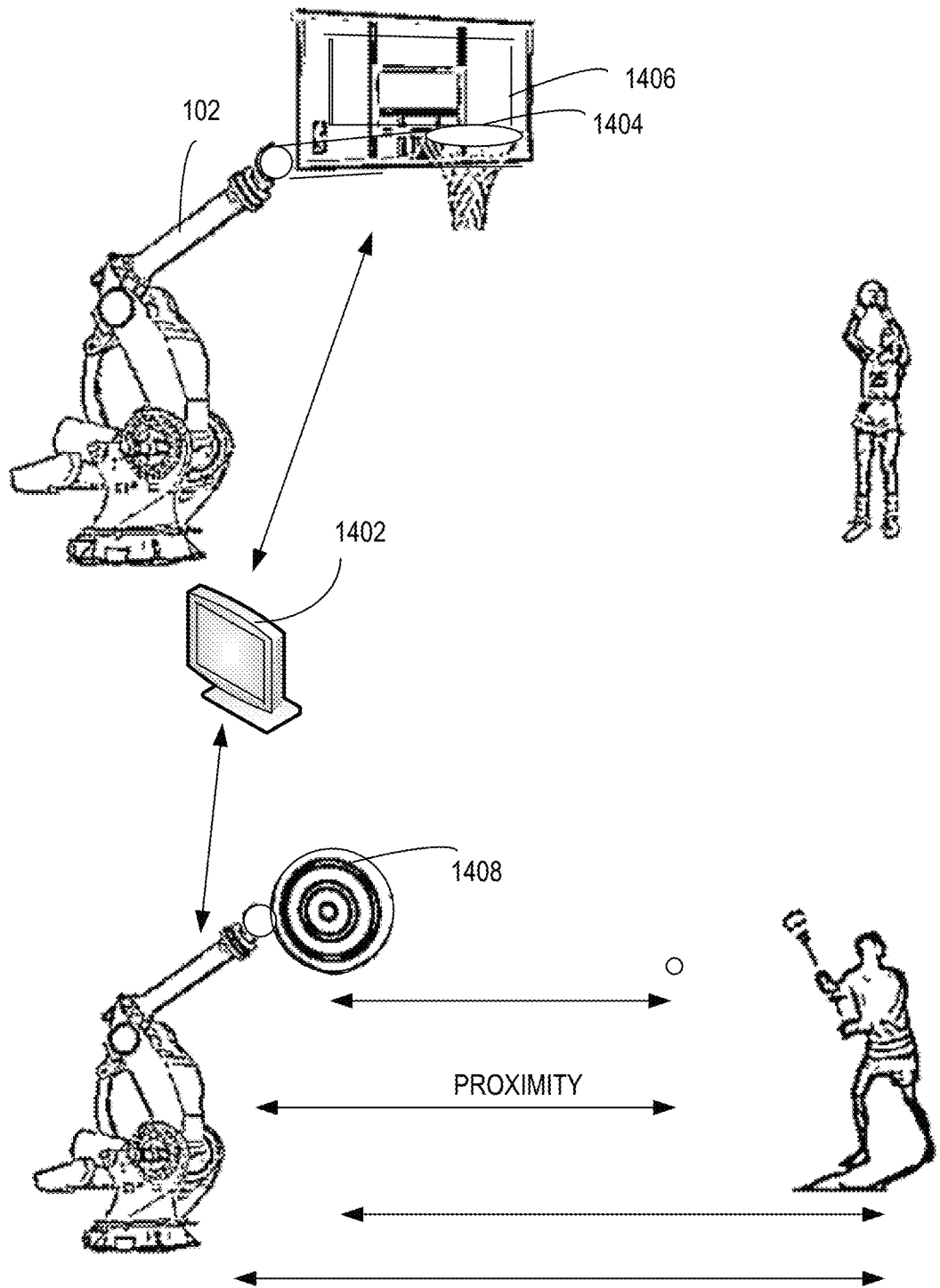
FIG. 14 depicts an exemplary diagram illustrating an exemplary embodiment of a made or miss sensor within an exemplary basketball application, and the use of an exemplary proximity sensor coupled to the exemplary athletic training device, as well as an exemplary possible configuration of the exemplary user interface with the exemplary sensor data displayed, according to an exemplary embodiment.

FIG. 14 depicts diagram 1400 illustrating another exemplary embodiment of an exemplary use of exemplary sensor devices (1404, 1406, 1408), which according to an exemplary embodiment, may be coupled to an exemplary embodiment of the athletic training device 102, and/or a user interface (UI) 1402, which may be coupled by wires or wirelessly (not shown), and the UI 1402 may display sensor data obtained from the sensing devices 1404, 1406, and/or 1408, such as, for example, any made and/or missed data, and, and/or proximity of the user to the target, which may be displayed, e.g., but not limited to, in a unit of measure such as, e.g., but not limited to, meters, centimeters, inches, and/or feet. Exemplary sensor devices 1404-1408 and exemplary sensors are discussed below with reference to FIGS. 15-18. The UI 1402 device as depicted may include an output device such as, e.g., but not limited to, a display monitor, and/or touch screen, etc. The UI device 1402, may not only include an output device, as shown, or otherwise, such as motors, lights, display screens, etc., but may rather further include one or more input devices, such as, e.g., but not limited to, a sensor, a keyboard, touchscreen, etc., as well as a robotic brain such as, e.g. but not limited to, one or more computer processor(s), a memory, and/or a communications bus, and/or interface to other components (not shown). FIG. 14 depicts exemplary proximity measurements between a ball and target, a ball and robot, a user and target, a user and robot, etc., according to various exemplary embodiments, by which such captured sensor data can be used, e.g., to analyze, e.g., but not limited to, accuracy at certain distances, distances when shots are taken, safe distances and/or perimeters about a robot and/or a goal, etc.

Figure 15:
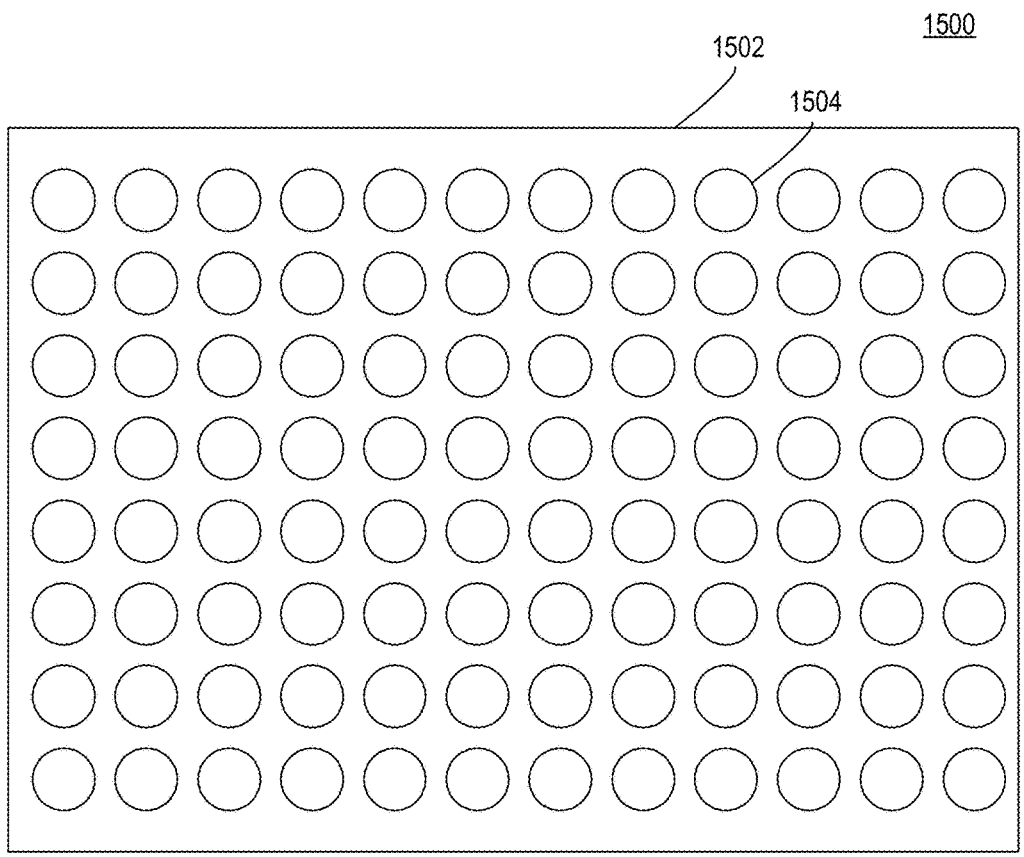
FIG. 15 depicts an exemplary embodiment, of an exemplary sensing interface with an exemplary array of a plurality of exemplary sensors, according to an exemplary embodiment.

FIG. 15 depicts an exemplary embodiment, of an exemplary sensing interface 1500 with an exemplary array of a plurality of exemplary sensors 1504, which may be coupled to a substrate or other sensor housing 1502, according to an exemplary embodiment. According to one exemplary embodiment an array of sensing regions may detect a ball coming into proximity to a particular portion of the sensor housing 1502, or sensors 1504. For example, an exemplary sensor 1504 may include a touch sensor, which similar to a key on a keyboard, or portion of a touchscreen, may detect contact with the sensor. As another exemplary sensor 1504, a light sensor may sense something coming into proximity of the light or color sensor, and the object (such as a ball), may cause generated light to be reflected from a light source, into the light sensor. Alternatively, an expected light source, which is then interfered with by an object, may be detected by a receiving sensor, which recognizes that an expected light signal is no longer being sensed (similar to a garage door light sensor, used to interrupt closing of a garage door on an infant, etc.). Other types of sensors such as, e.g., but not limited to, an ultrasonic sensor may be used to send off an ultrasonic sound wave, which may bounce off of a person or object (ball), and may via an ultrasonic transceiver/transducer, may identify the distance from the sensor of the person or object from which the ultrasonic sound wave may be bouncing off.

Figures 16A, 16B:
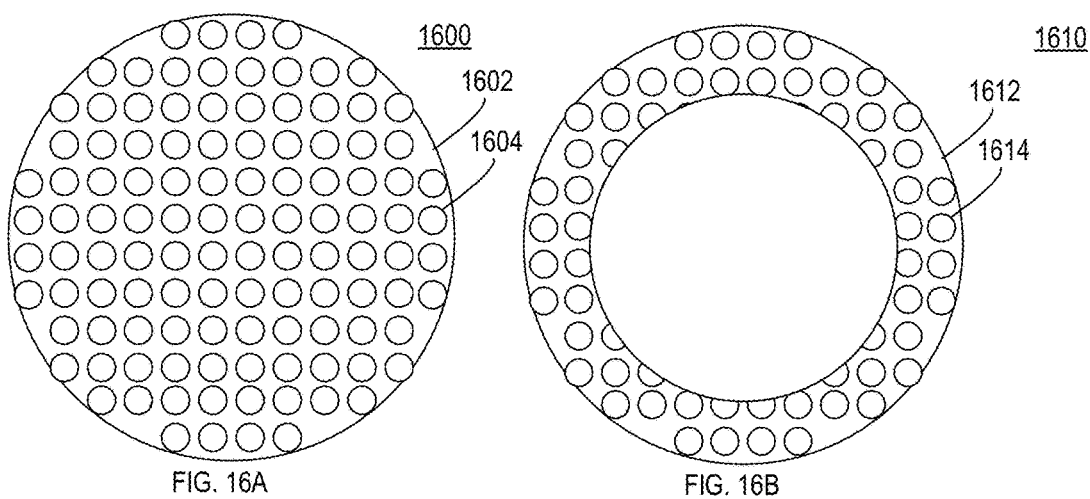
FIG. 16A depicts another exemplary embodiment of another exemplary sensing interface, with another exemplary array of an exemplary plurality of exemplary sensors and/or indicators, according to an exemplary embodiment.
FIG. 16B depicts an exemplary diagram of an exemplary goal and/or hoop with associated sensors, and/or indicators, according to an exemplary embodiment.

FIG. 16A depicts an exemplary diagram 1600 illustrating another exemplary embodiment of another exemplary sensing interface 1602, with another exemplary array of an exemplary plurality of exemplary sensors and/or indicators 1604, according to an exemplary embodiment.

FIG. 16A depicts, in detail, another exemplary embodiment of another exemplary sensing interface, with another exemplary array of an exemplary plurality of exemplary sensors 1604 and/or indicators (which may, e.g., but not limited to, indicate an area where a ball or other projectile may have impacted the sensing surface), arranged according to an exemplary embodiment across an exemplary surface area, in an exemplary two-dimensional array fashion, according to an exemplary embodiment. According to another exemplary embodiment, the sensors 1604 may be arranged in mutually exclusive annular rings about an exemplary bullseye (and/or similar to an archery and/or dart board target and/or shooting and/or biathlon, etc.), as shown in FIG. 14, according to another exemplary embodiment. According to one exemplary embodiment, sensing device 1602 may be placed atop, below, in front of, behind, and/or within, or without a goal such as, e.g., but not limited to, as shown in 1404, 1406, and/or 1408, of FIG. 14.

FIG. 16B depicts an exemplary diagram 1610 of an exemplary goal and/or hoop 1612, with associated sensors, and/or indicators 1614, according to an exemplary embodiment. An exemplary annular ring embodiment with one or more sensors arranged about the exemplary annular ring is only an example. Other example embodiments may be rectangular, polygonal, triangular, etc., as can be apparent to those skilled in the relevant art. According to exemplary embodiments, sensors 1614 may be arranged not only on a flat surface, such as the top of an exemplary basketball hoop, but may be on other surfaces, such as, e.g., but not limited to, an interior and/or exterior surface, such as an inside or outside of an exemplary truncated conical basket of an exemplary basketball hoop embodiment, or the edges, inside or outside of a hockey net, etc. Some sensors in an exemplary embodiment may also serve as indicators, and some indicator devices may also have a sensing aspect, but in some exemplary embodiments, an indicator and/or sensor may only serve a singular purpose. Exemplary indicators may include light emitting diode (LED)-based lighting elements such as, e.g., but not limited to, solid state semiconductor LED.

Figure 17:
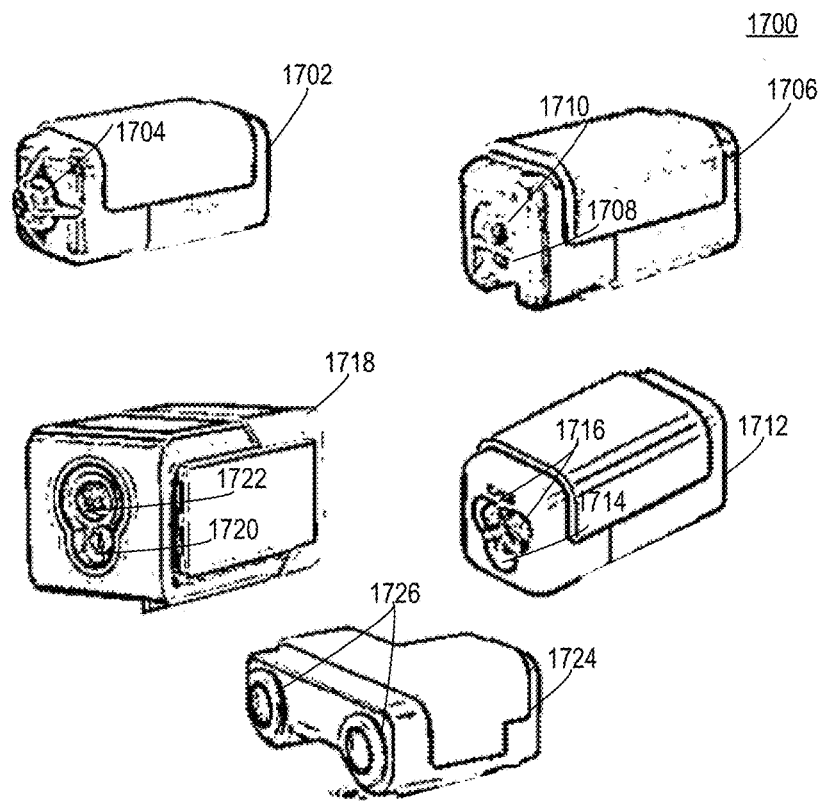
FIG. 17 depicts various exemplary sensors as may be used in various exemplary embodiments of the present invention, including exemplary but nonlimiting touch sensors, light sensors, color sensors, and ultrasonic sensors, according to various exemplary embodiments.

FIG. 17 depicts illustrations 1700 of various well known, exemplary sensors 1702, 1706, 1712, 1718, and/or 1724, as may be used in various exemplary embodiments of the present invention, including exemplary sensing devices as illustrated in FIGS. 14-16, above. Exemplary sensors illustrated may include, e.g., but may not be limited to exemplary touch sensors 1702, exemplary light sensors 1706, exemplary color sensors 1712, 1718, and/or exemplary ultrasonic sensors 1726, etc., according to various exemplary embodiments. The depicted sensors are well known sensors available from LEGO Mindstorms and/or EV3 Robotics kits, and serve merely as examples of well known sensor technologies as may be integrated into an exemplary sensing device 1404, 1406, 1408, according to an exemplary embodiment.

Exemplary touch sensor 1702 may include a touch actuator 1704, which when depressed and/or compressed, may cause the sensor 1702 to notify a coupled device that a touch has been sensed, according to an exemplary embodiment.

Exemplary light sensor 1706 may include a passive device (not shown) which may detect light crossing a photoelectric cell such as, e.g., but not limited to, a Cadmium sensor, and/or may include an active device 1706 as shown, including a light source 1708, which may generate light, which may then reflect off of an exemplary surface, and may be reflected back into an exemplary light sensor 1710, which may detect the reflection of the light created by light source 1708.

Exemplary color sensor 1712 may include an exemplary passive sensing device (not shown) which may detect colored light crossing a photoelectric cell such as a Cadmium sensor, or an electronic camera sensor, etc., and/or may include an active device 1712, 1718 as shown, including an exemplary light source 1714, 1720, respectively, which may generate light, which may then reflect off of an exemplary surface such as, e.g., but not limited to, an exterior of a ball, puck, projectile, etc., and may be reflected back into an exemplary color and/or light sensor 1716, 1722, respectively, which may detect the reflection of the light created by light source 1714, 1720.

Exemplary ultrasonic sensor 1724 may include an exemplary passive sensing device (not shown) which may detect via an exemplary transceiver (receiver and/or transmitter) and/or transducer, etc., and/or may include an active device 1724 as shown, including an exemplary transceiver and/or transducer 1726 which may generate ultrasonic waves, which may then reflect off of an exemplary surface such as, e.g., but not limited to, a ball, etc., and/or may be reflected back into the receiver portion of the transceiver/transducer, which may detect the reflection of the ultrasonic wave in the sensor 1726.

Various other well-known exemplary sensors may be used without parting from the scope of the claimed inventions.

Figure 18:
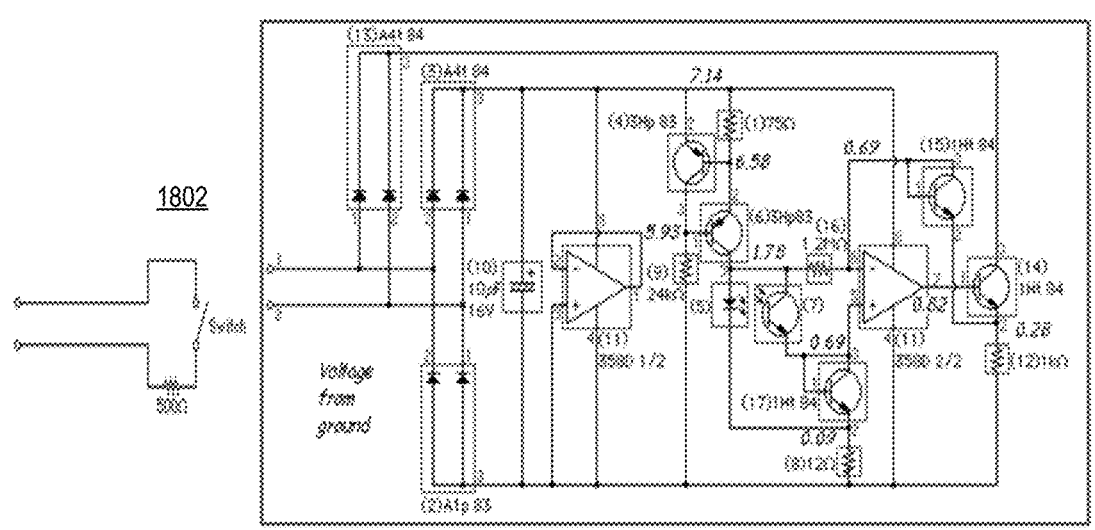
FIG. 18 depicts exemplary sensor circuitry for an exemplary touch sensor, and exemplary light sensor, according to various exemplary embodiments.

FIG. 18 depicts exemplary sensor circuitry for an exemplary touch sensor circuit 1802, and/or an exemplary light sensor 1804 (potions of which may be used with an exemplary color sensor, and/or ultrasonic sensor, etc.), according to various exemplary embodiments.

An example circuit 1802 as may be included within an exemplary touch sensor 1702 is illustrated in an exemplary schematic diagram of exemplary circuit 1802, which may include a contact switch, which according to an exemplary embodiment, may be held open with a spring and/or other biasing member, and may be, e.g., but not limited to, be coupled, and/or wired in series with an exemplary load resistor, e.g., 500 ohm resistor, etc., as shown, and may upon being touched, may close the circuit shown in 1802. The circuit 1802 may be closed by, e.g., but not limited to, upon the spring switch being compressed, according to an exemplary embodiment. An example touch sensor 1702 may detect whether the actuator 1704 of the sensor is being pressed, has been bumped, and/or has been released, according to an exemplary embodiment. The so-called brain and/or computer processor of the robotic device may upon actuation of the actuator 1704, may sense the closed switch 1802, and may upon such sensing may register that the actuation was sensed by logging, e.g., but not limited to, a time, and form of actuation sensed, etc.

FIG. 18 also depicts an exemplary circuit 1804 illustrating an example circuitry 1804 for an example light sensor 1706. The example light sensor 1706 is a powered sensor, meaning the light sensor 1706 may require power to run its circuitry 1804. These example Lego sensors only have two wires connecting them, thus the two wires must be used both to send power to, and receive signals from, the sensor. Polarity can also be an issue given that connectors may allow sensors (input devices) (and motors (or other output devices)) to be attached in any one of four different orientations. These complications are handled by a combination of a special circuit comprised of a diode bridge (2, 3, 13) on the left side of circuit 1804, and a storage capacitor (10) and special software that rapidly switches between driving the circuitry and reading off the sensed values. The capacitor stores enough power so that the circuit may continue to function when the sensor 1706 is being read. The light sensor 1706 is said to be an active sensor in that it not only senses light using sensor 1710, but it also provides a source of light 1708, i.e., it does not rely passively on a source of light.

Another example sensor may include, as discussed above with reference to FIG. 17, a color sensor 1712, which may in addition to sensing light similar to light sensor 1706, may also sense a range of reflected color, using color sensors 1716, and may also include a light source 1714, making it an active sensing device.

Yet another example sensor, as discussed above with reference to FIG. 17, may include color sensor 1718, which may include light source 1720, and light/color sensor 1722.

Another type of sensor, as discussed above with reference to FIG. 17, is an exemplary ultrasonic sensor 1724, (a transceiver and/or transducer, etc.) may use an ultrasonic sensor 1726 to generate an ultrasonic signal, which the sensor may also detect, which may be used to detect a given distance. can measure the distance from the sensor to something that it is facing, and detect movement. An example ultrasonic sensor can determine a distance such as, e.g., in centimeters, or inches. The maximum distance of an example Lego ultrasonic sensor can measure 233 cm with a precision of 3 centimeters. The ultrasonic sensor works by sending out ultrasonic sound waves that bounce off an object ahead of it and then back. The sensor senses the time it took for the ultrasonic wave to reflect. This example sensor is accurate at detecting flat surfaces. Various other sensors may also be used including, e.g., but not limited to, a location based sensor, a global positioning system (GPS), and/or a gyro sensor, accelerometer, rangefinder, location sensor, altimeter, etc.

Various Exemplary Embodiments of an Exemplary Athletic Training System

According to one exemplary embodiment, an exemplary backboard 1502 (see FIG. 15) with sensors 1504 can, in one exemplary embodiment include a hoop 1404 (e.g., as shown in FIG. 14), 1612 with sensors 1614 (see FIG. 16B). According to an exemplary embodiment, the exemplary sensors be coupled to exemplary indicators to visually indicate when the sensor senses contact or the close proximity of the ball.

According to an exemplary embodiment, an exemplary sensor may include an exemplary integrated indicator(s) that may display, e.g., by light, etc., any sensors which were contacted, and may register and store any such exemplary contact, so as to record or store for late access or comparison, and/or for a longer time, up to permanently and may display, e.g., but not limited to, temporarily, an exemplary sensed area that may have been contacted along with any other exemplary relative information such as, e.g., but not limited to, impact pressure, velocity and/or angle of impact and/or number of impacts and/or score as an exemplary displayed alphanumeric character(s) or phrase, and/or other indicator such as, e.g., a chart and/or graph such as, e.g., but not limited to, a graph, a bar chart, a line chart, a pie chart, etc. According to an exemplary embodiment, the information may be displayed on a display associated with the device, and/or or may be pushed to be displayed on an exemplary other device, such as, e.g., but not limited to, an exemplary wearable device, such as, e.g., but not limited to, a wrist wearable device, a smartphone, a fitness band, a fitness bracelet, digital watch, smart watch, mobile device, Google Glass, head up display, smart glasses, holographic lens, hololens, augmented reality, virtual reality, etc. Exemplary information about an exemplary trajectory could also be captured, as well as, e.g., but not limited to, the motion of the player as they propel the object and/or projectile, and/or ball towards the target and/or goal.

In one exemplary embodiment, an exemplary light, etc. may illuminate indicating a particular region, and may change when a change is sensed. For example, an exemplary strikezone of an exemplary baseball homeplate may be equipped with one or more illumination devices (e.g., light or laser beams), which according to an exemplary embodiment may illuminate an exemplary strike zone, e.g., but not limited to, in an exemplary particular light such as, e.g., red, using, e.g., but not limited to, color lasers, and may, e.g., but not limited to, when sensing a ball in any particular area of the strikezone, may so indicate using, e.g. but not limited to, a different color light, such as, e.g., a blue light, etc. According to an exemplary embodiment, a strikezone can be displayed via an additional display and/or an exemplary augmented reality for users with a smartphone in an example stadium.

In one exemplary embodiment, the ball may be equipped with one or more sensors, which may register whether any portion of the ball entered the exemplary illuminated strikezone, and may definitively confirm or overrule a called strike by an umpire in an exemplary baseball embodiment.

According to another exemplary embodiment, exemplary lights, LEDs, and/or other indicators on, e.g., but not limited to, the backboard and/or goal can be used to indicate the exemplary intended objective in relation to the whole goal, according to an exemplary embodiment. So, the exemplary indicated intended objective may, e.g., but not limited to, alternate between, e.g., corners, or the center or follow a progression of variable other exemplary locations to, e.g., test, not just the ability to hit the goal, but to also, more accurately hit a specific intended targeted area of the goal, that can be adjusted, and/or adjusted automatically, and/or via an exemplary selection, etc. According to an exemplary embodiment, a strike zone and/or personified sporting goal can be displayed via an additional display and/or an exemplary augmented reality for users with a smartphone in an example stadium.

According to another exemplary embodiment, an exemplary medical assessment may be provided, e.g., to provide an exemplary baseline for skills and to provide an exemplary means of assessment to determine effects of an athlete's injury and/or to, e.g., gauge the status of recovery from an injury, etc. According to an exemplary embodiment, aspects may also be used to assess other abilities, disabilities, and/or impairments, etc., that may be due to aging, drug use, other outside influence, etc.

According to an exemplary embodiment, an exemplary robot can be mounted on a system of exemplary rails, and/or other motors, wheel(s), gear(s), belt(s), and/or chain(s), etc., —driven mobility enabler(s), and/or means of movement, so that the robot can dynamically move within an exemplary range of motion, and/or not always have to remain stationary in a specific location.

According to an exemplary embodiment, an exemplary backboard could have flags that can, e.g., hang down, etc., that may wave as the goal moves to provide an indication of velocity and changes in velocity.

According to an exemplary embodiment, various exemplary sizes of targets and goals may be provided.

According to an exemplary embodiment, an addition feature enabling measuring of an exemplary impact and/or pressure forces a blocker can place on the exemplary robot such as, e.g., when they block in football. The exemplary device can have an exemplary padded portion coupled to the robot, with exemplary pressure sensors, among other possible sensors, and/or may provide an exemplary surface in place of the goal. According to an exemplary embodiment, the exemplary sensors may be used to measure an exemplary force exerted on the exemplary pad and/or on the different joints of the robot to determine how much force and the angles and duration of the force that can be applied by a given player. According to an exemplary embodiment, conventionally, the only way to measure player strength is by lifting various amounts of weight, but in this invention the robot can be able to provide custom measurements for each player and the measurements can be conducted, according to an exemplary embodiment, at different heights and angles, and can provide a complete body measure, instead of just parts as is done in weight lifting for an example leg press, and/or a bench press, etc.

According to an exemplary embodiment, the exemplary robot can propel an exemplary ball, such as, e.g., but not limited to, an exemplary American football (e.g., oblong spheroid) with an exemplary spin by mounting a device on the robot, that can throw the football, i.e., creating a spin and/or spiral on the ball before it is released just as the combination of a human quarterback's arm, wrist, hand and fingers place a spin/spiral on a ball as it is thrown, enabling simulation of various throwing, allowing receivers to practice unaided by a human quarterback. Similarly, the robot may fill other roles allowing a human to practice against the robot, for a longer time period than a human player might be able to play, or even when an opposing human opponent is unavailable. The amount and angle of spin could be varied, programmable, made random, etc., to simulate human throwing and/or catching. Similarly, other sports' opponents may also be so simulated, including, e.g., but not limited to, a basketball shooting machine, etc., allowing a defender to try to intercept a pass, or shot, etc.

According to an exemplary embodiment, the robot can also be used with, e.g., but not limited to, a hockey stick to hit and/or block, etc., a hockey puck, field hockey ball, tennis ball, etc. with programming an addition of couplers to electromechanically grasp the stick, racquet, etc.

According to an exemplary embodiment, in various baseball embodiments, various capabilities may be provided for the exemplary robot and/or the robot's exemplary strike board (i.e., the board 1500, 1600, 1610, with exemplary sensors and/or indicators, as outlined above, for an exemplary, but nonlimiting basketball backboard embodiment of the strikeboard, and can in the baseball embodiment display, and/or simulate an exemplary catcher's mitt) and may detect and/or sense and/or indicate, and/or evaluate a pitcher's ability to throw an exemplary type of pitch such as, e.g., but not limited to, an exemplary pitch such as, e.g., a curve, a slider, a fastball to an exemplary specific target and/or to measure and/or store, and/or analyze, and/or display, the performance. According to an exemplary embodiment, the exemplary trajectory and/or speed of the exemplary baseball can be mapped and/or captured in three dimensions for further analysis using exemplary 2D and/or 3D, etc. scanners (such as those used in an exemplary Microsoft Kinect, and/or as described elsewhere, herein) and/or by using exemplary scanners that can detect an exemplary device and/or sensor, and/or component, that can be placed in the exemplary ball, according to an exemplary embodiment. According to an exemplary embodiment, similar to radar, but while providing a continuous image, the scanner sensing devices and/or output display indicators, may be provided. According to an exemplary embodiment, an exemplary similar analysis may be performed of the exemplary ball's movements, such as, e.g., but not limited to, speed and/or trajectory, etc., could also be used to e.g., test an exemplary batter's ability at hitting different pitches, according to an exemplary embodiment.

Figure 19:
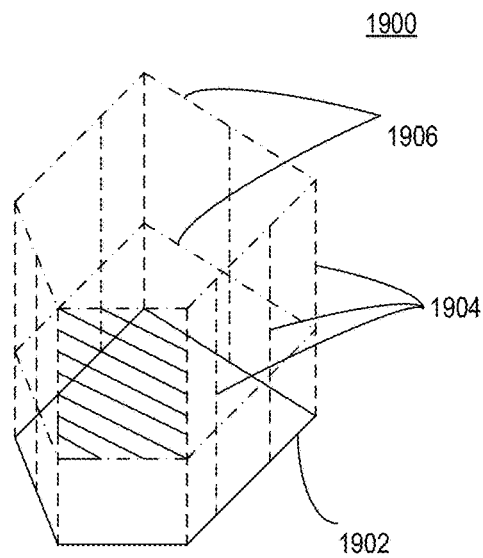
FIG. 19 depicts an exemplary illustration of an exemplary improved homeplate having exemplary illumination features.
Figure 20:
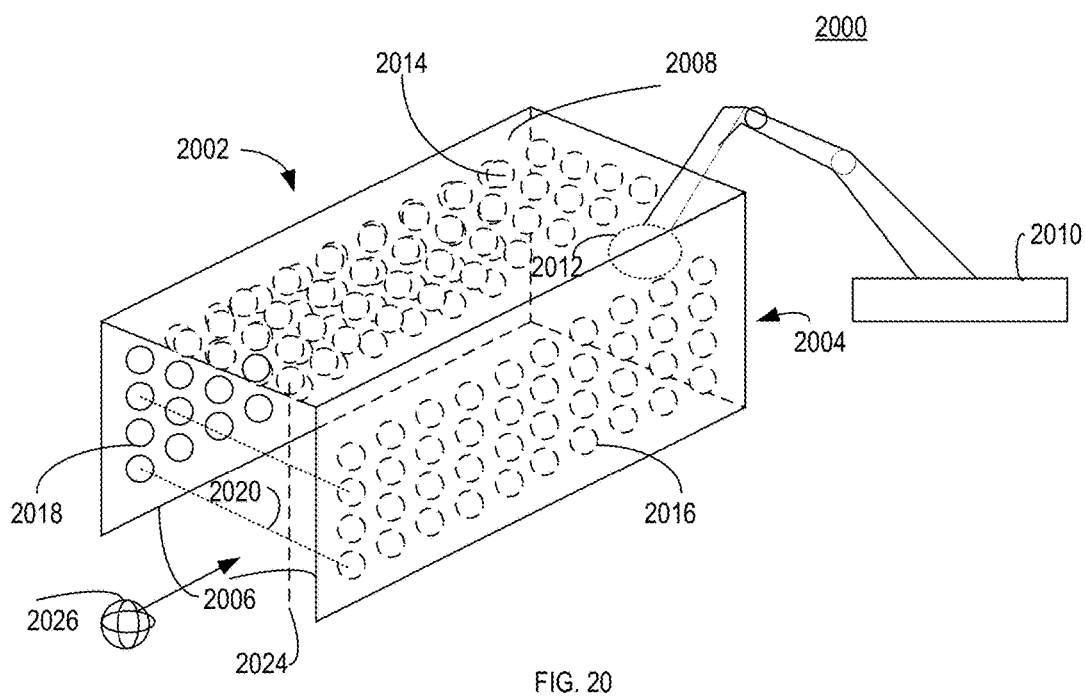
FIG. 20 depicts an exemplary illustration of an exemplary tunnel three-dimensional (3D) scanner pitching trainer system, according to an exemplary embodiment.

FIG. 19 depicts an exemplary illustration of an exemplary improved homeplate having exemplary illumination features. Specifically, in an exemplary embodiment, FIG. 19 depicts an exemplary illustration 1900 of an exemplary improved homeplate 1902, having exemplary illumination features, which may include vertical lines 1904, and/or horizontal lines 1906, according to an exemplary embodiment. According to an exemplary embodiment, an exemplary strike zone illuminator 1900 may be used to illustrate to an audience of an exemplary baseball game, where a strike zone may be. The array of lasers may project vertically to show the plate 1902 location of the batter's box (represented by the volume of the exemplary crosshatched pentagonal cylinder). The exemplary horizontal laser lines 1906 may be drawn with an exemplary horizontal laser batter's box. According to an exemplary embodiment, a strike zone and/or personified sporting goal can be displayed via an additional display and/or an exemplary augmented reality for users with a smartphone in an example stadium. FIG. 20 depicts an exemplary illustration of an exemplary tunnel three-dimensional (3D) scanner pitching trainer system, according to an exemplary embodiment. Specifically, in an exemplary embodiment, FIG. 20 depicts an exemplary illustration 2000 of an exemplary tunnel 2002, which may be in an exemplary embodiment, a three-dimensional (3D) scanner pitching trainer system, according to an exemplary embodiment. According to an exemplary embodiment, tunnel 2002 may include an optional partial back wall 2004, at least two (2) side walls 2006, a roof, or top ceiling 2008, each wall with respective groups of exemplary arrays of sensors 2014, 2016, 2018 as shown, at least the wall's interiors. According to an exemplary embodiment, the exemplary sensors 2014-2018 may be used to sense when an object moves through the tunnel 2002, such as, e.g., but not limited to, when an exemplary baseball 2026, which may be thrown through horizontal sensing areas 2020, and/or vertical sensing areas 2024, which may include visual sensors identifying the ball 2026 moving through the tunnel 2002, or may be radio frequency or other electronic sensor, which may sense movement of the ball 2026 through the tunnel 2002, using some sensing such as a color of the ball, or an embedded transmitter. According to an exemplary embodiment, the ball 2026 may be through the tunnel 2002 to an exemplary catcher's glove 2012 coupled to an exemplary robot 2010, according to an exemplary embodiment. According to an exemplary embodiment, the exemplary tunnel scanner may capture and analyze the motion of the exemplary ball (e.g., baseball, etc.) as it moves through the tunnel 2002, when thrown or otherwise propelled. An exemplary embodiment may capture, store, analyze and process such as, e.g., but not limited to, mapping a trajectory in three dimensions of the movement of the ball, and may measure speed/velocity, path, curving, vertical and/or horizontal displacement, etc. According to an exemplary embodiment, the tunnel may be used with a catcher, or may be used with an exemplary robotic catcher stand-in. According to an exemplary embodiment, the tunnel 2002 may be staffed by at least one person, who may evaluate a pitcher by analyzing the sensor output, when reviewing an exemplary baseball player. According to an exemplary embodiment, the coordinates of the movement of the ball 2026 may be mapped and may be displayed (or a printout may be generated) of the exemplary motion analysis of the ball trajectory and velocity. According to an exemplary embodiment, displayed data can be displayed via an additional display and/or an exemplary augmented reality, or holographic lens, for users with a smartphone, and/or augmented vision device, in an example stadium.

According to an exemplary embodiment, various exemplary aspects may use the exemplary trainer system's exemplary scanning capability to measure the athletes' movements including, e.g., but not limited to, exemplary athlete velocity and/or athlete acceleration such that the information can be applied to the robot's movements. According to an exemplary embodiment, in other words, if the exemplary athlete typically jumps at a certain acceleration then an exemplary basket can be programmed to replicate the inverse of that movement for purposes of practice or as the athlete moves on the floor, at an exemplary certain velocity, then the basket can move at that velocity as well, according to an exemplary embodiment.

According to an exemplary embodiment, being able to measure an exemplary player's range of exemplary acceleration and/or speed/velocity can allow the robot to more accurately replicate the movements for practice and can provide useful information for the athlete and the coach.

According to an exemplary embodiment, example useful information could include: "how high does the athlete typically jump and how fast can he or she stop?"

Another aspect, according to an exemplary embodiment, can be the different reference points for the measurement(s). According to an exemplary embodiment, a different reference point could be, e.g., but not limited to, a head, a ball, a hand(s), etc.

According to an exemplary embodiment, an exemplary training system can collect this exemplary movement data as the target person/user can move in three dimensions.

According to an exemplary embodiment, the scanner can measure how fast the player can move the ball, puck, etc. when pitching, throwing, hitting, striking, etc. According to an exemplary embodiment, the scanner can determine, "How fast can the player dribble the ball, and how much force did he exert/transfer into the ball?" "How high does the ball bounce as the player dribbles?" Gathering this data may be interesting to the player, and this data may be used to determine the different skills or qualities of different players. According to an exemplary embodiment, the information may be collected, analyzed and repackaged. The analyzed information, according to an exemplary embodiment, may be productized and delivered to the player and may serve to provide a new dimension to athletic analysis of coordination, etc.

According to an exemplary embodiment, the robot can also be used in a defensive way where the player has to dribble around the robot, as if the robot is moving as a defensive player in a repeating motion.

According to an exemplary embodiment, further features may be provided relating to basketball. According to an exemplary embodiment, one feature can provide the ability to vary the size of the target, goal or hoop for purposes of practicing, to help the athlete feel more of a sense of accomplishment, and to increase the difficulty of a task. For example, an adjustable radius hoop, or an adjustable width, or length goal, can be provided.

According to an exemplary embodiment, one can capture the essence of what motivates a kid to keep wanting to put a ball in the basket? Who cares? The exemplary embodiment of the invention can be later than planned, but can conclude that the player(s) is/are motivated by the feeling of satisfaction that a player gets when the ball goes through the hoop. According to an exemplary embodiment, if a player can make more baskets the player can want to practice more, and if the hoop is larger, can be easier to hit, and then the player can feel more accomplished in their abilities and the player can have more of a desire to practice. According to an exemplary embodiment, the exemplary feature of "And to the same degree the hoop, target or goal can be made smaller to further test and refine one's abilities.

According to an exemplary embodiment, an option to change the target size when an athlete may begin with the user using the robotic trainer being able to increase the size of the basket or target as the player(s) get familiar with this new type of moving target. According to an exemplary embodiment, hockey players can practice for a hockey goal, soccer, lacrosse, etc., can be adjusted to be made smaller for practicing too.

FIG. 1 depicts an exemplary diagram 100 illustrating an exemplary computer/communications device hardware architecture as may be used in various components of exemplary embodiments of the present invention. FIG. 1 depicts an exemplary diagram 100 illustrating an exemplary computer/communications device hardware architecture as may be used in various components to programmatically control and/or program and/or use the robot 102-driven athletic trainer system 100 of exemplary embodiments of the present invention. FIG. 1 depicts an exemplary view 100 of an exemplary computer system 124, 126, 128, or 130 as may be used in implementing an exemplary embodiment of the present invention. FIG. 1 depicts an exemplary embodiment of a computer system that may be used in computing devices such as, e.g., but not limited to, user devices 124-130, etc. and/or web server 109 and/or application server 111, social network computing device(s) of a social network, which may in an exemplary embodiment reside in a cloud- and/or network-based device 132, user devices 124-130, network components 134, 136, etc. according to an exemplary embodiment of the present invention. FIG. 1 depicts an exemplary embodiment of a computer system that may be used as client device 124-130, or a server device (not shown), etc. The present invention (or any part(s) or function(s) thereof) may be implemented using hardware, software, firmware, or a combination thereof and may be implemented in one or more computer systems or other processing systems. In fact, in one exemplary embodiment, the invention may be directed toward one or more computer systems capable of carrying out the functionality described herein. An example of a computer system 100 is shown in FIG. 1, depicting an exemplary embodiment of a block diagram of an exemplary computer system useful for implementing the present invention. Specifically, FIG. 1 illustrates an example computer 124-130, which in an exemplary embodiment may be, e.g., (but not limited to) a personal computer (PC) system running an operating system such as, e.g., (but not limited to) WINDOWS MOBILE™ for POCKET PC, or MICROSOFT® WINDOWS® NT/98/2000/XP/CE/7/8, etc. available from MICROSOFT® Corporation of Redmond, Wash., U.S.A., SOLARIS® from SUN® Microsystems of Santa Clara, Calif., U.S.A, OS/2 from IBM® Corporation of Armonk, N.Y, U.S.A, Mac/OS, OS/X, iOS from APPLE® Corporation of Cupertino, Calif., U.S.A, etc, or any of various versions of UNIX® (a trademark of the Open Group of San Francisco, Calif., USA) including, e.g., LINUX®, HPUX®, IBM AIX®, and SCO/UNIX®, etc. However, the invention may not be limited to these platforms. Instead, the invention may be implemented on any appropriate computer system running any appropriate operating system. In one exemplary embodiment, the present invention may be implemented on a computer system operating as discussed herein. An exemplary computer system, computer 100 is shown in FIG. 1. Other components of the invention, such as, e.g., (but not limited to) a computing device, a communications device, a telephone, a personal digital assistant (PDA), a personal computer (PC), a handheld PC, client workstations, thin clients, thick clients, proxy servers, network communication servers, remote access devices, client computers, server computers, routers, web servers, data, media, audio, video, telephony or streaming technology servers, a tablet, a phone, a mobile phone, a cellular phone, a communications device, an iPod, an iPhone, a smartphone, an iPad, a tablet based device, a smart phone, an ANDROID OS device, an iOS device, a Symbian based device, a Windows 8, 10, n, device, etc., may also be implemented using a computer such as that shown in FIG. 1.

The computer system 124-130 may include one or more processors, such as, e.g., but not limited to, microprocessor(s) (not shown, but internal to 123, 126, 128, and 130). The processor(s) (and/or controller, field programmable gate array (FPGA), application specific integrated circuit (ASIC), microcontroller, system on a chip (SOC), etc.) may be connected and/or coupled to a communication infrastructure (e.g., but not limited to, a communications bus, cross-over bar, or network, etc.), not shown, but part of 124-130. Various exemplary software embodiments may be described in terms of this exemplary computer system. After reading this description, it will become apparent to a person skilled in the relevant art(s) how to implement the invention using other computer systems and/or architectures.

Computer system 124-130 may include a display interface 502 that may forward, e.g., but not limited to, graphics, text, and other data, etc., from the communication infrastructure (or from a frame buffer, etc., not shown) for display on the display unit 138.

The computer system 124-130 may also include, e.g., but may not be limited to, a main memory (not shown, but within 124-130, in an exemplary embodiment), random access memory (RAM), and a secondary memory (not shown, but may also be couplable to 124-130, etc. The secondary memory may include, for example, (but not limited to) a hard disk drive (HDD), and/or a removable storage drive (not shown, but representing, e.g., but not limited to, a floppy diskette drive, a magnetic tape drive, an optical disk drive, a compact disk drive CD-ROM, etc.) The removable storage drive may, e.g., but not limited to, read from and/or write to a removable storage unit (not shown, but capable of being placed in, or coupled to 124-130, in a well-known manner. Removable storage unit, also called a program storage device or a computer program product, may represent, e.g., but not limited to, a floppy disk, magnetic tape, optical disk, compact disk (CD), digital versatile disc (DVD), high definition optical media, e.g., BLU-RAY, etc. which may be read from and written to by removable storage drive. As can be appreciated, the removable storage unit may include a computer usable storage medium having stored therein computer software and/or data.

In alternative exemplary embodiments, secondary memory may include other similar devices for allowing computer programs or other instructions to be loaded into computer system 124-130. Such devices may include, for example, a removable storage unit 522 and an interface 520. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, universal serial bus device (USB), flash memory, solid state memory device (SSD), and other removable storage units and/or interfaces, which may allow software and data to be transferred from the removable storage unit to computer system 124-130.

Computer 124-130 may also include an input device (e.g., touch based screen of display 138 and/or stylus or pen of 128 such as, e.g., (but not limited to) a mouse or other pointing device such as a digitizer, and a keyboard or other data entry device (none of which are labeled).

Computer 124-130 may also include output devices, such as, e.g., (but not limited to) display 138, and display interface (not labeled). Computer 124-130 may include input/output (I/O) devices such as, e.g., (but not limited to) communications interface, cable and/or communications path (not labeled), etc. These devices may include, e.g., but not limited to, a network interface card, and/or modems and/or other interface coupling devices (not labeled). The communications interface may allow software and data to be transferred between computer system 124-130 and external devices. Examples of communications interface 124-130 may include, e.g., but may not be limited to, a modem, a network interface (such as, e.g., an Ethernet card), a communications port, a Personal Computer Memory Card International Association (PCMCIA) slot, PC Card, SDRAM, universal serial bus (USB), solid state device (SSD), and card, etc. Software and data transferred via communications interface may be in the form of signals which may be electronic, electromagnetic, optical or other signals capable of being received by communications interface, when not transient, or when not transitory. These signals may be provided to communications interface via, e.g., but not limited to, a communications path such as, e.g., but not limited to, a channel and/or communications link 140. This channel may carry signals, which may include, e.g., but not limited to, propagated signals, and may be implemented using, e.g., but not limited to, wire or cable, fiber optics, a telephone line, a cellular link, a radio frequency (RF) link 140 and other communications channels, etc. External input/output devices can be coupled including, e.g., but not limited to, a touchscreen, a pen based and/or stylus based input system, a flat panel display, a high definition (HD), a 4K, 8K, 16K, nK, etc. display, a holographic display, an augmented reality (AR) display (integrating a 3D image into a camera or other sensed environment, a hololens augmented environment, a mixed reality, augmented reality, Magic Leap, a virtual reality (VR) and/or other enhanced reality environment display such as, e.g., but not limited to, a heads up display (HUD), etc.

In this document, the terms "computer program medium" and "computer readable medium" may be used to generally refer to media such as, e.g., but not limited to removable storage drive, a hard disk installed in hard disk drive, a removable and/or nonremovable medium, and/or nontransitory signals, etc. These computer program products may provide software to computer system 124-130. The invention may be directed to such computer program products.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct or indirect physical or electrical contact with each other. "Coupled" may mean that two or more elements are in direct physical or electrical contact. However, "coupled" may also mean that two or more elements are not in direct contact with each other, but yet still co-operate or interact with each other.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments of the present invention may include apparatuses for performing the operations herein. An apparatus may be specially constructed for the desired purposes, or it may comprise a general-purpose device selectively activated or reconfigured by a program stored in the device.

Embodiments of the invention may be implemented in one or a combination of hardware, firmware, and software. Embodiments of the invention may also be implemented as instructions stored on a machine-readable medium, which may be read and executed by a computing platform to perform the operations described herein. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other form of propagated signals (e.g., carrier waves, infrared signals, digital signals, etc.), and others.

Computer programs (also called computer control logic), may include object oriented computer programs, and may be stored in main memory and/or the secondary memory and/or removable storage units, also called computer program products. Such computer programs, when executed, may enable the computer system to perform the features of the present invention as discussed herein. In particular, the computer programs, when executed, may enable the processor to provide a method to resolve conflicts during data synchronization according to an exemplary embodiment of the present invention. Accordingly, such computer programs may represent controllers of the computer system 124-130.

In another exemplary embodiment, the invention may be directed to a computer program product comprising a computer readable medium having control logic (computer software) stored therein. The control logic, when executed by the processor, may cause the processor to perform the functions of the invention as described herein. In another exemplary embodiment where the invention may be implemented using software, the software may be stored in a computer program product and loaded into computer system using, e.g., but not limited to, removable storage drive, hard drive or communications interface, etc. The control logic (software), when executed by the processor 504, may cause the processor to perform the functions of the invention as described herein. The computer software may run as a standalone software application program running atop an operating system, or may be integrated into the operating system.

In yet another embodiment, the invention may be implemented primarily in hardware using, for example, but not limited to, hardware components such as application specific integrated circuits (ASICs), or one or more state machines, etc. Implementation of the hardware state machine so as to perform the functions described herein can be apparent to persons skilled in the relevant art(s).

In another exemplary embodiment, the invention may be implemented primarily in firmware.

In yet another exemplary embodiment, the invention may be implemented using a combination of any of, e.g., but not limited to, hardware, firmware, and software, etc.

Exemplary embodiments of the invention may also be implemented as instructions stored on a machine-readable medium, which may be read and executed by a computing platform to perform the operations described herein. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other form of propagated signals (e.g., carrier waves, infrared signals, digital signals, etc.), and others.

The exemplary embodiment of the present invention makes reference to wired, or wireless networks. Wired networks include any of a wide variety of well-known means for coupling voice and data communications devices together. A brief discussion of various exemplary wireless network technologies that may be used to implement the embodiments of the present invention now are discussed. The examples are non-limited. Exemplary wireless network types may include, e.g., but not limited to, code division multiple access (CDMA), spread spectrum wireless, orthogonal frequency division multiplexing (OFDM), 1G, 2G, 3G wireless, Bluetooth, Infrared Data Association (IrDA), shared wireless access protocol (SWAP), "wireless fidelity" (Wi-Fi), WIMAX, and other IEEE standard 802.11 compliant wireless local area network (LAN), 802.16-compliant wide area network (WAN), and ultrawideband (UWB), etc.

Bluetooth is an emerging wireless technology promising to unify several wireless technologies for use in low power radio frequency (RF) networks.

IrDA is a standard method for devices to communicate using infrared light pulses, as promulgated by the Infrared Data Association from which the standard gets its name. Since IrDA devices use infrared light, they may depend on being in line of sight with each other.

The exemplary embodiments of the present invention may make reference to WLANs. Examples of a WLAN may include a shared wireless access protocol (SWAP) developed by Home radio frequency (HomeRF), and wireless fidelity (Wi-Fi), a derivative of IEEE 802.11, advocated by the wireless ethernet compatibility alliance (WECA). The IEEE 802.11 wireless LAN standard refers to various technologies that adhere to one or more of various wireless LAN standards. An IEEE 802.11 compliant wireless LAN may comply with any of one or more of the various IEEE 802.11 wireless LAN standards including, e.g., but not limited to, wireless LANs compliant with IEEE std. 802.11a, b, d or g, n, X, such as, e.g., but not limited to, IEEE std. 802.11 a, b, d and g, n (including, e.g., but not limited to IEEE 802.11g-2003, etc.), etc.

Exemplary Personified Sporting Goal Exemplary Embodiments

Figure 21A:
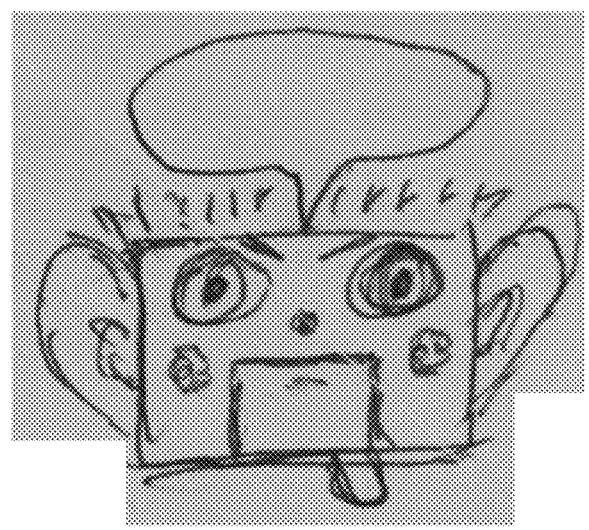
FIGS. 21A, 21B, 21C, and 21D depict various exemplary illustrations of an exemplary personified sporting goal, according to an exemplary embodiment.
Figure 21B:
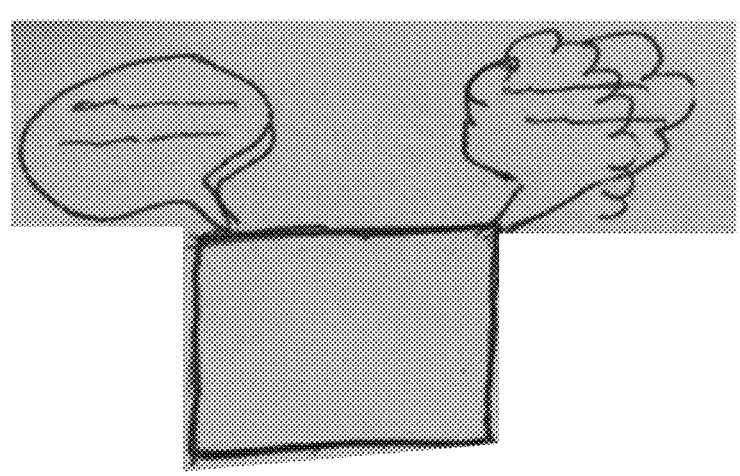
Figure 21C:
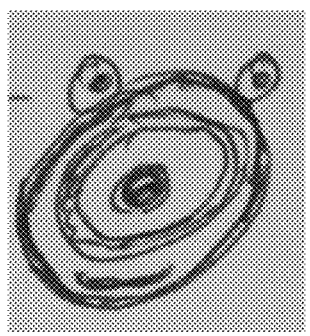
Figure 21D:
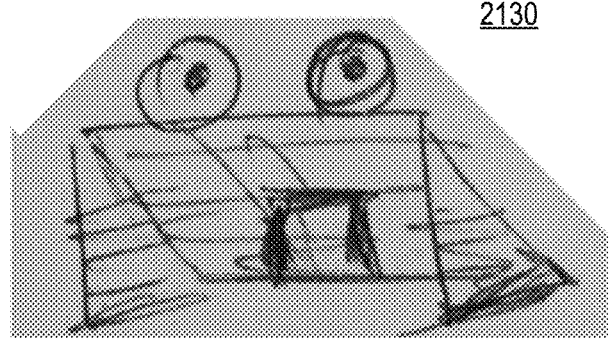

FIGS. 21A, 21B, 21C, and 21D, et seq., depict various exemplary illustrations of an exemplary personified sporting goal, according to an exemplary embodiment. FIG. 21A illustrates a drawing 2100 of an exemplary personified basketball backboard including illustrative personified attributes, including, e.g., but not limited to, exemplary eyes, cheeks, nose, eye brows, ears, hair, tongue, etc., according to one exemplary embodiment. In one exemplary embodiment a cartoon bubble can be used to display, e.g., but not limited to, example text, emoji, emoticons, text, video, and/or audio, etc.

Figure 22:
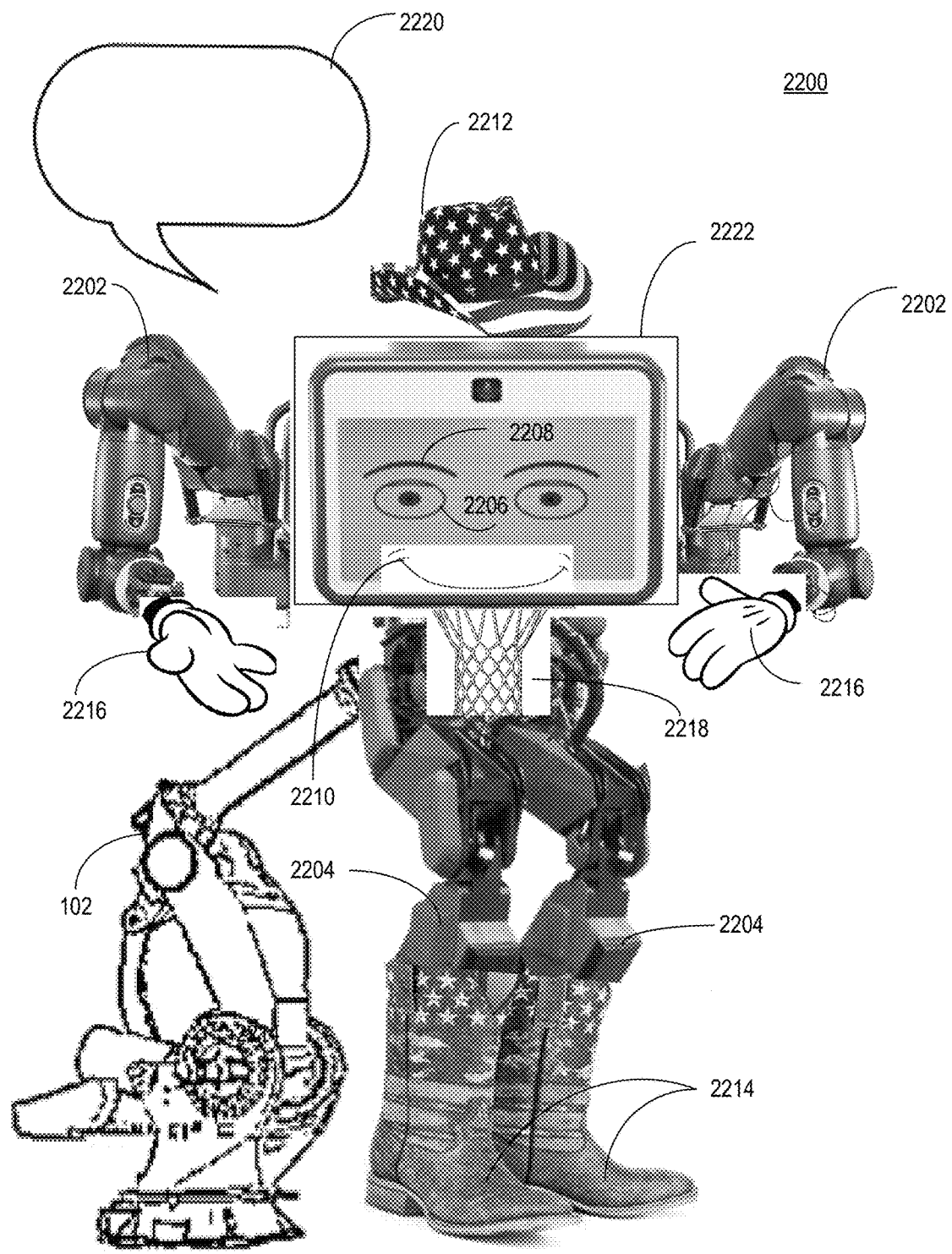
FIG. 22 depicts an illustration of an exemplary personified sporting goal, according to an exemplary embodiment.

FIG. 22 depicts an exemplary illustration 2200 depicting an exemplary personified sporting goal having various exemplary character attributes (including, e.g., but not limited to, exemplary arms 2202 and legs 2204 appendages, exemplary displayed facial features (e.g., eyes 2206, eyebrows 2208, mouth 2210), exemplary cowboy hat 2212, boots 2214, hands 2216, and a goal 2218 (basketball backboard, hoop and net), and speech bubble 2220), and transparent protective cover 2222, according to an exemplary embodiment. An exemplary embodiment of a sport goal, or modification or adjustment of the goal, net and/or scoreboard such as, e.g., but not limited to, a basketball backboard, or a soccer net, and frame, or a baseball scoreboard, etc. so that the sport goal can have and display human features and the sport goal can move, communicate, and/or exhibit human emotions that can be conveyed to the spectators, referee, and/or players, etc., according to an exemplary embodiment. The personified sport goal can exhibit human attributes such as, e.g., but not limited to, movement, expression and/or emotion, etc., through various actions and/or mediums in order to portray human emotion and/or communication, according to an exemplary embodiment. An example robotic arm, according to an exemplary embodiment, can comprise part of and/or be attached to, the personified sport goal to provide movement, according to an exemplary embodiment.

Various communication components can be included to implement an example sports goal device, including, e.g, but not limited to, wireless and/or wired communications, routers, bridges, gateways, switches, cabling, network interface cards, etc.

Various conventional automated toys exist, including communications subsystems as discussed and described at length in WO 01/69830, PCT/IL01/00248, the contents of which is incorporated herein by reference in its entirety. However, no personified sports goals have been disclosed previously. According to an exemplary embodiment, Applicant combines a useful, novel, and nonobvious combination of a sports goal with exemplary personified attributes, such as, e.g., but not limited to, appendages, facial features, emotional expressions, sounds, audio, video and/or textual insertions, etc. According to a preferred embodiment, the personified sporting goal can be coupled, in some embodiments, to an optional robot 102 (shown in FIG. 22). According to an exemplary embodiment, users, such as, e.g., but not limited to, an audience of a sports game, an athletic participant, and/or a referee, umpire, etc., can interact with the personified sports goal device. Via, e.g., speech bubble 2220, and/or via speakers, and/or on a scrolling text banner, via audio speakers, and/or video displays (such as, e.g., a flat panel liquid crystal display (LCD), and/or with an exemplary light emitting diode (LED) backlight, pixels, via sound system, etc. According to an exemplary embodiment, a user interface can be used by an example back office human user (similar to the Wizard of Oz), or an exemplary programmed user, and/or an artificial intelligence (AI) software agent user, which can include, in one exemplary embodiment, a neural network, a software decision support system, etc., any of which can control, and or manipulate the various components, such as, e.g., but not limited to, attributes shown in FIG. 22, etc., the exemplary emotions, gestures, interactions, etc. of the personified sports goal, as it interacts with other users.

According to one exemplary embodiment one or more flat panel or other displays can be used to provide, e.g., but not limited to, an exemplary facial feature, eyes, smile, tongue, mouth, ears, etc. According to one exemplary embodiment, robotic and/or animatronic appendages such as, e.g., but not limited to, ears, arms, legs, hands, feet, fingers, toes, tail, character features, animal features, object features, etc., can be provided, according to one exemplary embodiment.

An exemplar embodiment of the hardware and software, electrical and/or mechanical components of an example, wired or wirelessly coupled system of various components including a sporting goal, output display features, wireless communication facilities to a user interface for user computer device and/or programmed, and/or software based artificial intelligence (AI) engine and/or neural network system for controlling the personified sporting goal with its enhanced features for providing emotion, gestures, communication of various entertaining content, etc. via electronic, mechanical and electro-mechanical animatronic and/or robotic appendages and motor/actuator/gear/pneumatics and/or hydraulically controlled subsystems and assemblies of various exemplary embodiments, including controlling and moving appendages, facial features, emotions, attitude, expressions, feelings, etc. via humanlike personified movement and/or gestures by the mechanical and electronic components. Appendages coupled to motors and actuators can move like human or animal physical movements, can include various example sensors, may include any of various sensors such as, e.g., but not limited to, capacitive, touch sensing, sound capture, microphone, voice recognition, proximity, touch, ultrasonic, range finders, accelerometers, gyroscopic, location based, RFID, image sensing, cameras, etc., as well as output devices such as displays, appendages, motors, wheels, conveyors, ejectors, etc. Certain embodiments can simulate certain human activities, such as, e.g., but not limited to, spitting, throwing, ejecting, rejecting a ball, etc.

An example personified sport goal, according to an exemplary embodiment, can be controlled by a human and/or can be operated through programmed and/or artificial intelligence and/or can serve as the conscious embodiment for each team, such as, e.g., but not limited to, a mascot and/or a personality of a team, etc.

Figure 26:
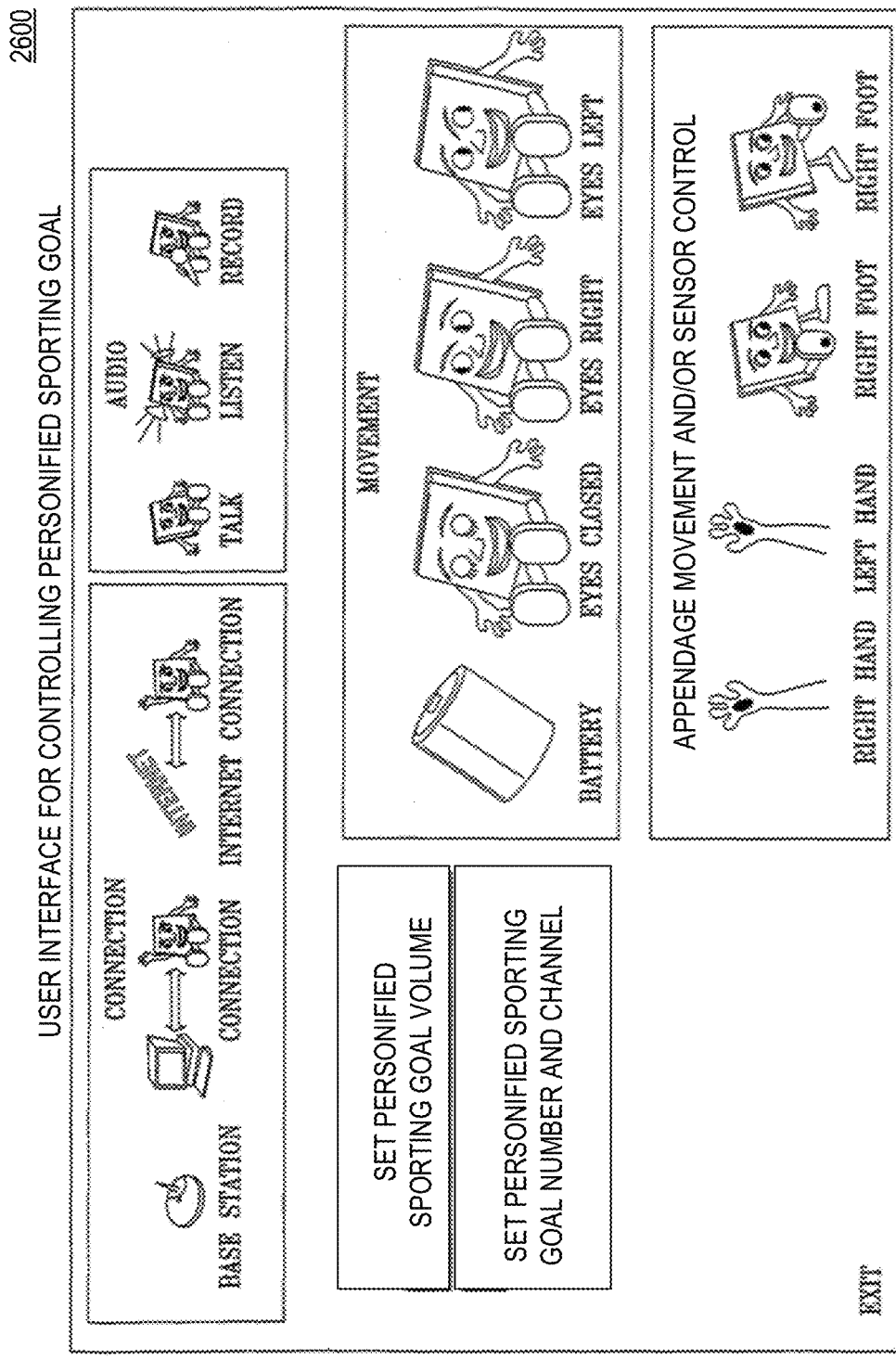
FIG. 26 depicts an example user interface for illustrating example UI controllable features of an example personified sporting goal, according to an example embodiment.

FIG. 26 depicts a diagram 2600 illustrating an example personified sports goal device user interface including various user interface selectable routines, and/or character movements, and/or interactions, etc. The illustrated examples are not intended to be exhaustive, but rather suggest example user friendly, simple, programmable, appendage animatronic and/or robotic appendage and sporting goal controller.

Another example personified sport goal, according to an exemplary embodiment, can have, e.g., but not limited to, physical human features such as, e.g., but not limited to, a face with a mouth, teeth, lips and/or tongue, eyes and/or pupils, ears, hair, nose, eyebrows, etc. The example personified sport goal, according to an exemplary embodiment can have a body and appendages such as, e.g., but not limited to, arms, hands, fingers, and/or legs, etc., that are, according to an exemplary embodiment, capable of controlled or uncontrolled movement.

Exemplary embodiment of an example personified sport goal, including exemplary animatronic and/or robotic, and/or moveable personified attributes of an example sports goal device, such as, an example basketball backboard/hoop and net with robotic and/or animatronic appendages, see FIG. 22, and/or a soccer goal coupled to a personified character or object (such as, e.g., a Mr. Potato head, face, portion of face, etc.), see FIG. 24, below.

In yet another example of a personified sport goal, according to an exemplary embodiment, the sport goal can express ideas and/or expression via audio and/or written words, and/or by conveying what the example personified sport goal is thinking via example thought balloons, as employed in comics, and/or in a banner type or other form of text and/or graphic display with e.g., but not limited to, static, scrolling, and/or moving words, etc., according to an exemplary embodiment.

Another example personified sport goal, according to an exemplary embodiment, can be portrayed by various means such as, according to an exemplary embodiment, a high definition (HD)/ultra-high definition (UHD)/4K/8K/16K/32K/nK, augmented reality (Argon, ArUco, JavaCV, GRATF, Goblin XNA, mixare, PTAM, DroidAR, GeoAR, BeyondAR, Mangan, Vrui, ARma, ARTooKit, Kudan AR, Layar SDK, Catchoom CraftAR SDK, Vuforia Augmented Reality SDK, Wikitude SDK, Gamar, Augment, Blippbuilder, buildAR, Catchoom CraftAR, Hoppala Augmentation, Layar Creator, TARTT, Webcam Social Shopper, WakingApp, AR Circuits, SkyView, Anatomy 4D, immersive computer generated environments, Aurasma, Blippar, iGreet, Layar, Nokia City Lens, Wikitude, XARMEX, Zappar), holographic lens, hololens, virtual reality (such as, e.g., but not limited to, Samsung Gear VR, HTC Vive, VivePort, Oculus Rift, etc.), etc. display screen, animation, and/or in combination with various mechanical devices such as, e.g., but not limited to, motors, actuators, pneumatic, gear and/or hydraulic lifts, limbs, appendages, etc.), according to an exemplary embodiment. Further, aspects can incorporate and/or be incorporated in gaming devices, such as the EyeToy, PlayStation Eye, Kinect, Nintendo 3DS, PlayStation Portable, PlayStation Vita and some mobile devices, use cameras to augment computer graphics onto live footage, according to an exemplary embodiment. Exemplary enhanced game environments that can be coupled with Applicant's claimed invention include e.g., but not limited to, Pokemon Go, AR Games, A.R. Warriors, Bravely Default, Cool Stacks, Cybergeneration, Dead Space, E.X. Troopers, Project DIVA F, Vocaloid, Hydrophobia, Ingress, LyteSHot, Raving Rabbids, Spectrek, Tuttuki Bako, Zombies Run, etc. The majority of AR software uses special cards which are read by the device to pinpoint where the graphics can form, according to an exemplary embodiment. Exemplary embodiments can incorporate any of various mixed reality environments including, e.g., hybrid reality, virtual worlds, mixed physical and/or virtual worlds, any of various strata of MR along a virtuality continuum, an/or mediality continuum, and/or reality-virtuality continuum from real environment (RE), to augmented reality (AR), to augmented virtuality (AV), to virtual environment (VE), etc. Thus, certain aspects, e.g., speech bubbles, etc., can be provided by any of various modalities across the reality-virtuality continuum, according to an exemplary embodiment. Exemplary environments can include, e.g., but not be limited to, cave automatic virtual environment (CAVE), head-up display (HUD), head-mounted display (HMD), Tablet PC, computer display and/or touchscreen, Personal Digital Assistant, Mobile phones and/or smartphones, etc., handheld and/or mobile, and/or wearable PC, immersive wearables, augmented reality, augmented virtuality, blended space, lifelike experience, mediated reality, mixed reality games, simulated reality, Supranet, Telexistence, Viractualism, Virtual reality, and/or Visuo-haptic mixed reality, etc.

Figure 27:
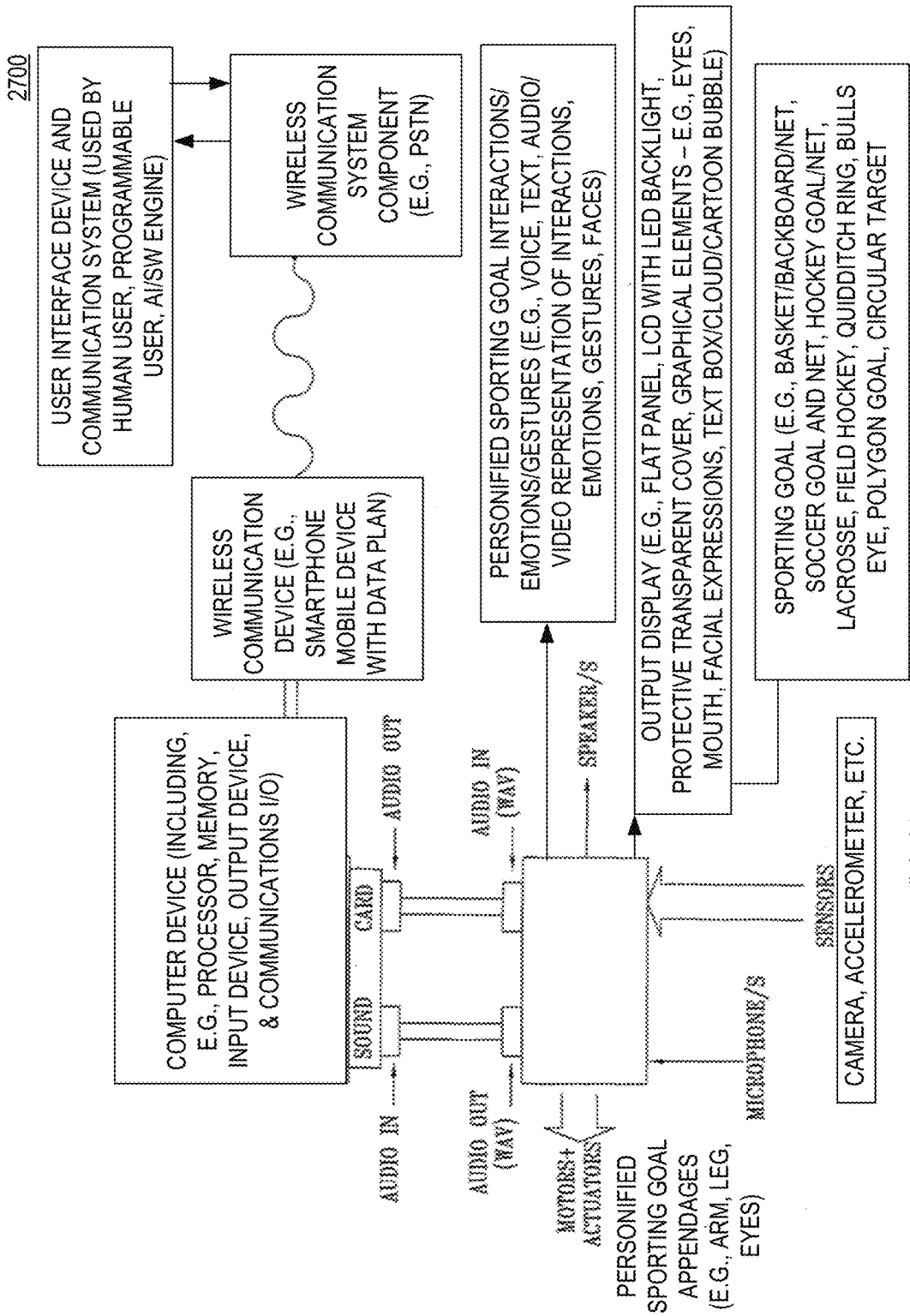
FIG. 27 depicts an example embodiment of an example group of electronic and mechanical components, as well as communications and networking components (including wireless links to allow user and/or programmable, and/or artificial intelligence based programmable controlled personified sporting goal manipulation, adjustment and example movement of appendages, as well as gestures, and emotional interactions, according to an example embodiment.

Various exemplary electronic, mechanical, telecommunications, and computer components are depicted in drawing 2700, are illustrated in FIG. 27.

Yet another example personified sport goal, according to an exemplary embodiment, can be visible from, e.g., one, both of two, or four or more, and/or all sides, so that all spectators, as well as players, officiating crews/referees/umpires, audience, and/or television viewing audience, can observe the character and/or the character's emotions, gestures, actions, interaction, communication, and/or read or observe its written, spoken (e.g., by voice, audio, and/or synthetic voice generation, etc.) and/or displayed communication via exemplary cartoon bubble, cloud, and/or other banner and/or scrolling text tape stream, etc. A personality of the character can be developed and familiar emotions/interactions can be created to the character(s)

Figure 23:
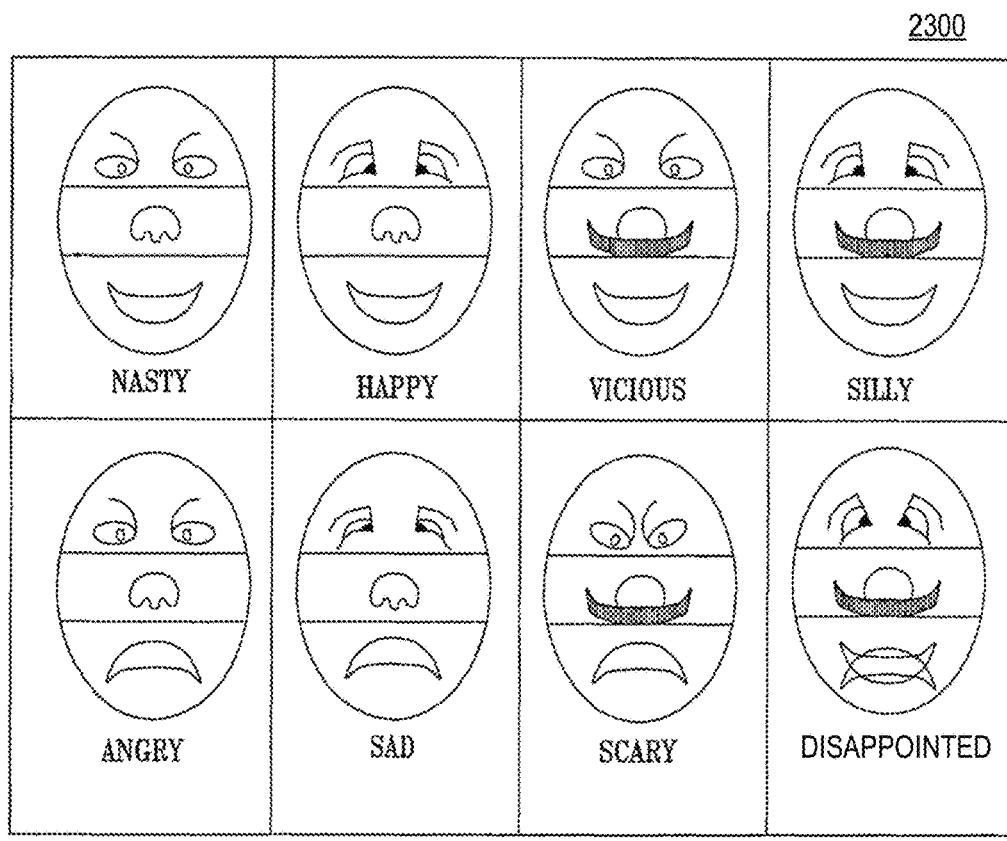
FIG. 23 depicts various exemplary emotions and/or emotional facial gestures, as may be combined in various exemplary embodiments with a sporting goal, as nonlimiting example embodiments.

FIG. 23 depicts in illustration 2300, various example emotional states and faces representative of various emotional states, and example facial gestures that could be used in an exemplary personified sporting goal to provide an example interaction, according to one exemplary, but nonlimiting embodiment.

Figure 24:
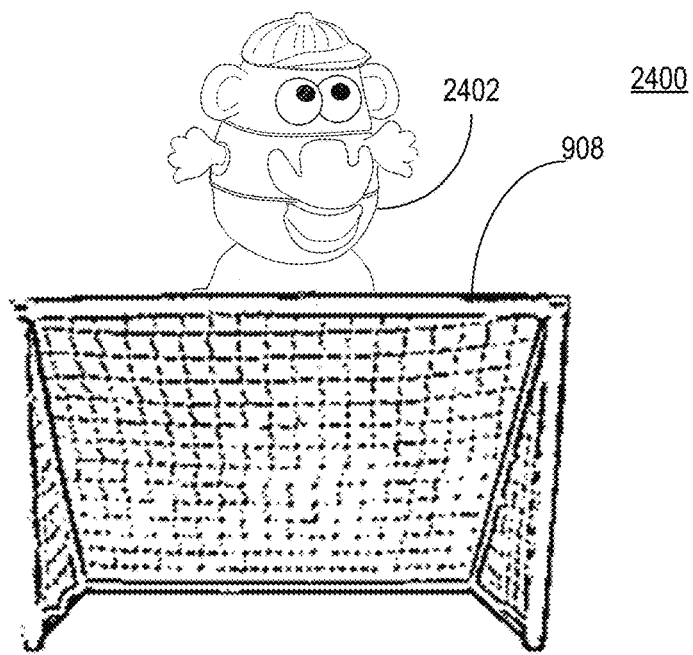
FIG. 24 depicts an example mascot and/or toy based example personified sporting goal, according to another exemplary embodiment.

FIG. 24 depicts another example personified sport goal, in this case an example large depiction of a body, or portion of a body such as, a face, eyes, a large potato head, etc. coupled to an exemplary soccer or hockey goal, according to an exemplary embodiment. According to one exemplary embodiment, the personified sporting goal can be applied to any and all current and/or future sports that can utilize a goal, scoreboard and/or net where a personified sport goal character(s) can appear, such as, e.g., but not limited to, in baseball, basketball, soccer, volleyball, golf, FRISBEE flying disc golf, rugby, football, golf, lacrosse, hockey, track and field, QUIDDITCH, field hockey, winter sport, summer sport, shooting sport, tennis, and/or archery, etc.

According to an exemplary embodiment, a character, or portion of a character, such as, e.g., but not limited to, a Mr. Potato Head, on an exemplary goal, such as, e.g., but not limited to, a soccer goal, can be associated with and/or coupled to the goal, but may not necessarily be a physical part of the goal since the exemplary character can be placed on it, adjacent to it, or in close proximity to it. In an exemplary embodiment, the example character can include a remotely controlled character, which can be on or adjacent to the sporting field, to express emotions and/or to entertain the crowd. Conventional mascots are just humans in costumes, with few ways to communicate, generally only by hand gestures, or with the help of cheerleaders, and the mascots are conventionally so small, that they are hard to see. An exemplary embodiment, on the other hand, can provide gigantic, exaggerated facial characters for displaying emotion on, e.g., a jumbotron and/or other large display and/or other output device.

According to an exemplary embodiment, an exemplary, illustrative apparatus can incorporate, e.g., a face, or other body portion, and/or body into an exemplary sporting goal, backboard, and/or goal, with for example, but not limited to, very large, and/or exaggerated, features, allowing example emotions to be visible enough for the audience to see and can enable an audience to understand a displayed emotion and/or interaction, from a distance, in an exemplary embodiment.

Figure 25:
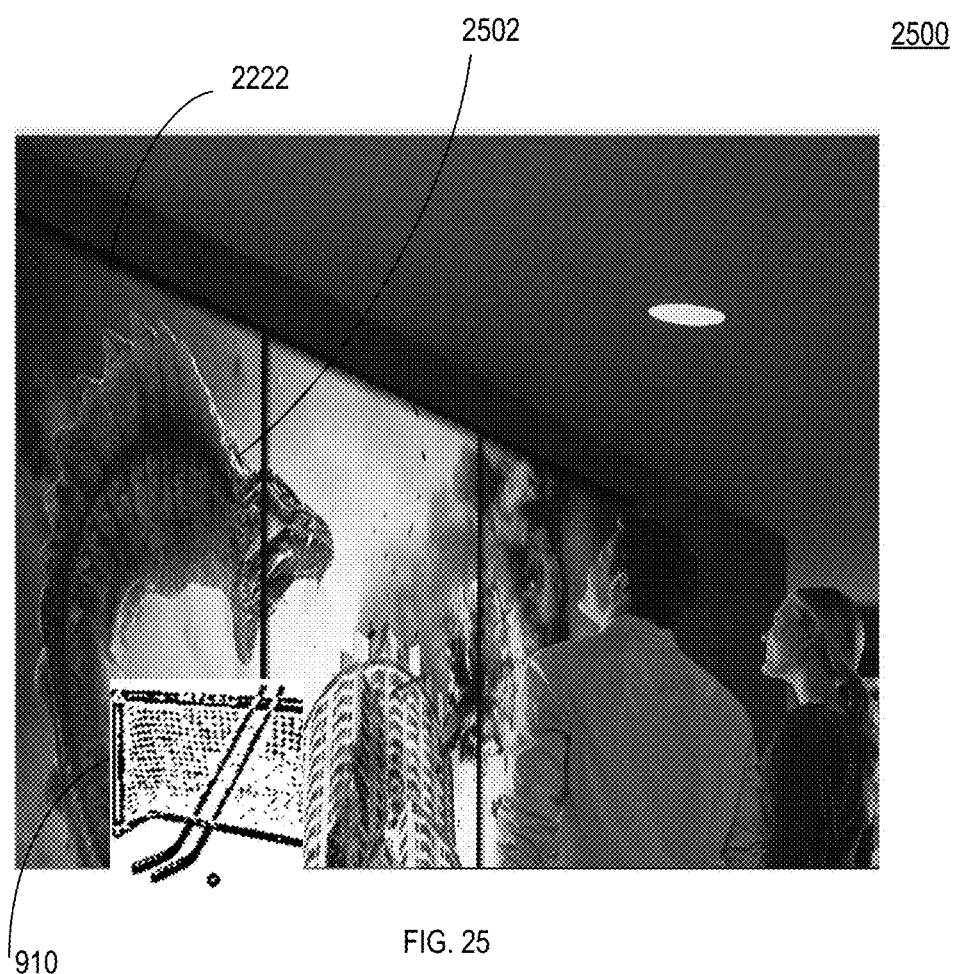
FIG. 25 depicts an example personified sporting goal, embodiment including a flat display screen (such as, e.g., but not limited to, an LCD screen with LED backlight, video content in combination with a sporting goal, example personified sporting goal, according to another exemplary embodiment.

FIG. 25 depicts in illustration 2500, an example flat screen 2222 can add, e.g., but not limited to, a basket, hockey goal 910, or other goal to flat display screen image 2502 of Samsung flat panel 2222 digital signage.

FIG. 26 depicts an exemplary user interface for controlling an exemplary personified sporting goal including various exemplary graphical user interface elements, according to an exemplary embodiment. Various exemplary user selectable movement icons and/or controller selectable functions as can be used along with an exemplary joy stick, mouse, 2D and/or 3D controller device, etc.

FIG. 27 depicts an exemplary personified sports goal apparatus device, audio/video output interfaces/devices, communications components (wired and/or wireless, etc.), an exemplary personified sporting goal, a computer controller device, including an exemplary user interface and/or an exemplary graphical user interface (GUI) elements, speakers and/or microphone interfaces, and/or motors, and/or actuator interfaces and/or devices, and/or sensors, and/or couplers, cables, and/or communication facilities/couplings/etc., according to an exemplary embodiment.

Figure 28:
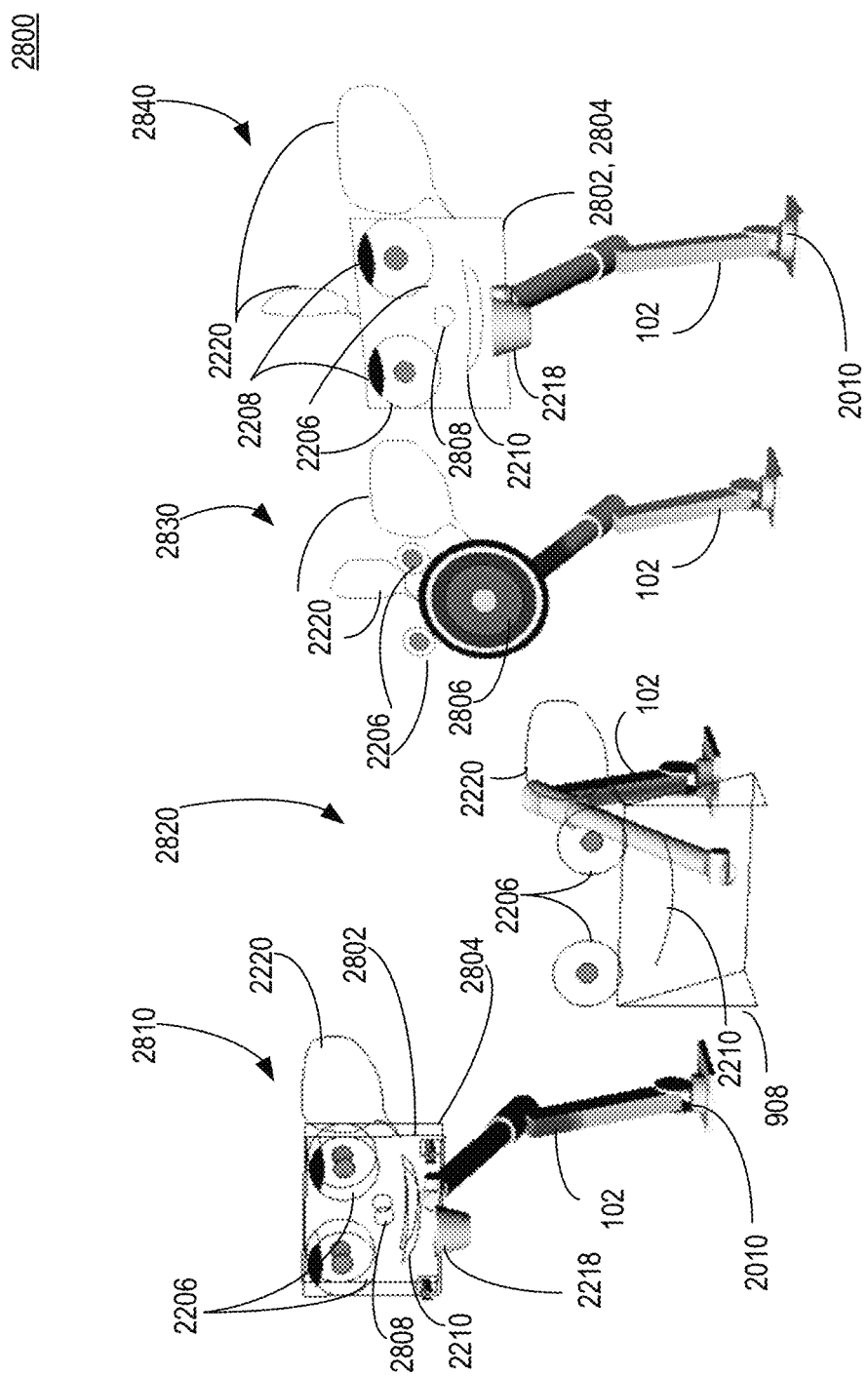
FIG. 28 depicts a diagram illustrating various exemplary embodiments of various exemplary personified sporting goals, according to an exemplary embodiment.

FIG. 28 depicts a diagram 2800 illustrating various exemplary embodiments of various exemplary personified sporting goals 2810, 2820, 2830, and 2840, according to an exemplary embodiment. Diagram 2800 depicts an exemplary two-sided personified sports goal 2810 for a basketball game and/or optional speech box(es), according to an exemplary embodiment. Diagram 2800 depicts an exemplary two-sided personified sports goal 2820 for a soccer game and/or optional speech box(es), according to an exemplary embodiment. Diagram 2800 also depicts an exemplary personified sports goal 2830 for an example target and/or archery and/or dartboard, etc. game and/or optional speech box(es), according to an exemplary embodiment. Diagram 2800 also depicts an exemplary personified sports goal 2840 for an example one- or two-sided basketball game illustrating an example set of facial features and/or optional speech box(es), according to an exemplary embodiment.

An example embodiment of the personified basketball backboard 2810 can include, according to an exemplary embodiment, an example double-sided output display to simulate, e.g., but not limited to, two display output screens such as, e.g., but not limited to, a liquid crystal display (LCD), a light emitting display (LED), and/or other flat panel, picture element (pixel), backlit, or nonbacklit, and/or other display screen (and/or a partially transparent, partially opaque screen allowing viewing from either the front and/or back side of the backboard), etc., with one side for viewing by the audience in front of the backboard and one side for viewing by the audience behind the backboard, and/or a holographic display and/or augmented reality display enabling projection of the character, and/or portions of a character on the backboard (e.g., nose 2808, mouth 2210, etc., in an exemplary embodiment. In an exemplary embodiment, the screen(s) 2802, 2804 can display exemplary personified attributes, such as, e.g., but not limited to, eye or eyes 2206, eyebrows (not labeled), nose 2808, and/or mouth 2210, and/or exemplary speech boxes 2220, which may face in any of multiple directions, and/or may rotate or move for ease of viewing, in an exemplary embodiment. The sporting goal can advantageously move in personified fashion using robotic appendages and/or supports 102, according to an exemplary embodiment.

An example embodiment of the personified basketball backboard 2820 can include, according to an exemplary embodiment, a soccer, lacrosse, hockey goal, and/or field hockey, etc., which can include, e.g., but not limited to, one or more output display(s) and/or display portions (such as, e.g., but not limited to, round display elements for simulating example eyes, and/or an example rectangular display to simulate, e.g., a mouth and/or lips, the example display(s) to simulate, e.g., but not limited to, one, two, three, or more, display output screens such as, e.g., but not limited to, a liquid crystal display (LCD), a light emitting display (LED), and/or other flat panel, picture element (pixel), backlit, or nonbacklit, and/or other display screen (and/or a partially transparent, partially opaque screen allowing viewing from either the front and/or back side of the backboard), etc., with an example one side for viewing by the audience in front of the backboard and an example one side for viewing by the audience behind the backboard, and/or a holographic display and/or augmented reality display enabling projection of at least a portion of or a whole character, and/or portions of a character or face on an example portion, in an exemplary embodiment. In an exemplary embodiment, the screen(s) 2802, 2804 can display exemplary personified attributes, such as, e.g., but not limited to, eye or eyes 2206, eyebrows (not shown or labeled), nose (not shown or labeled), and/or mouth 2210, etc., and/or exemplary speech boxes 2220, which may face in any of multiple directions, and/or may rotate or move for ease of viewing, in an exemplary embodiment. The sporting goal 908 can advantageously move in personified fashion using robotic appendages and/or supports 102, according to an exemplary embodiment.

An example embodiment of the personified basketball backboard 2830 can include, according to an exemplary embodiment, a target for archery, darts, shooting, and/or biathlon, etc., which can include, e.g., but not limited to, one or more output display(s) and/or display portions (such as, e.g., but not limited to, round display elements for simulating example eyes 2206, and/or an example rectangular or circular display to simulate, e.g., a mouth and/or lips, and/or targets and/or rings, and/or bulls eye, such as, shown in the example display(s) to simulate, e.g., but not limited to, one, two, three, or more, display output screens such as, e.g., but not limited to, a liquid crystal display (LCD), a light emitting display (LED), and/or other flat panel, picture element (pixel), backlit, or nonbacklit, and/or other display screen (and/or a partially transparent, partially opaque screen allowing viewing from either the front and/or back side of the backboard), etc., with an example one side for viewing by the audience in front of the backboard and an example one side for viewing by the audience behind the backboard, and/or a holographic display and/or augmented reality display enabling projection of at least a portion of or a whole character, and/or portions of a character or face on an example portion, in an exemplary embodiment. In an exemplary embodiment, the screen(s) 2802, 2804 (not labeled), and/or eye displays 2206, and/or target display 2806, and/or speech box display(s) 2220 can display exemplary personified attributes, such as, e.g., but not limited to, eye or eyes 2206, eyebrows (not shown or labeled), nose (not shown or labeled), and/or mouth 2210, and/or exemplary speech boxes 2220, which may face in any of multiple directions, and/or may rotate or move for ease of viewing, in an exemplary embodiment. The sporting goal 2806, target, can advantageously move in personified fashion using robotic appendages and/or supports 102, according to an exemplary embodiment.

An example embodiment of the personified basketball backboard 2840 can include, according to an exemplary embodiment, an example single basketball screen, basket and net, and/or backboard, etc., which can include, e.g., but not limited to, one or more output display(s) and/or display portions (such as, e.g., but not limited to, round display elements for simulating example eyes, and/or an example rectangular display to simulate, e.g., a mouth and/or lips, the example display(s) to simulate, e.g., but not limited to, one, two, three, four, five, and/or more, display output screens such as, e.g., but not limited to, a liquid crystal display (LCD), a light emitting display (LED), and/or other flat panel, picture element (pixel), backlit, or nonbacklit, and/or other display screen (and/or a partially transparent, partially opaque screen allowing viewing from either the front and/or back side of the backboard), etc., with an example one side for viewing by the audience in front of the backboard and an example one side for viewing by the audience behind the backboard, and/or a holographic display and/or augmented reality display enabling projection of at least a portion of or a whole character, and/or portions of a character or face on an example portion, in an exemplary embodiment. In an exemplary embodiment, the screen(s) 2802, 2804, 2206, 2808, 2210, 2220 can display exemplary personified attributes, such as, e.g., but not limited to, eye or eyes 2206, eyebrows, nose, and/or mouth, etc. (not labeled), and/or exemplary speech boxes 2220, which may face in any of multiple directions, and/or may rotate or move for ease of viewing, in an exemplary embodiment. The sporting goal 2218 and/or backboard, and/or rim and/or net, can advantageously move in personified fashion using robotic appendages and/or supports 102, and/or may be configured to rotate and/or telescope, and/or compress, upon a base 2010, and/or about any of various intermediate joints and/or motors, and/or actuators and/or in multiple degrees of freedom, according to an exemplary embodiment.

The exemplary drawings 2800 show various exemplary embodiments of various optional and/or example speech and/or thought bubbles, and/or indications of exemplary audio output, or indications of speech and/or music, and/or audio, and/or thoughts, on each exemplary goal set, as may, in an example embodiment include multiple, perpendicular to each other speech bubbles for example multiple angle, full audience viewing, according to an exemplary embodiment.

Figure 29:
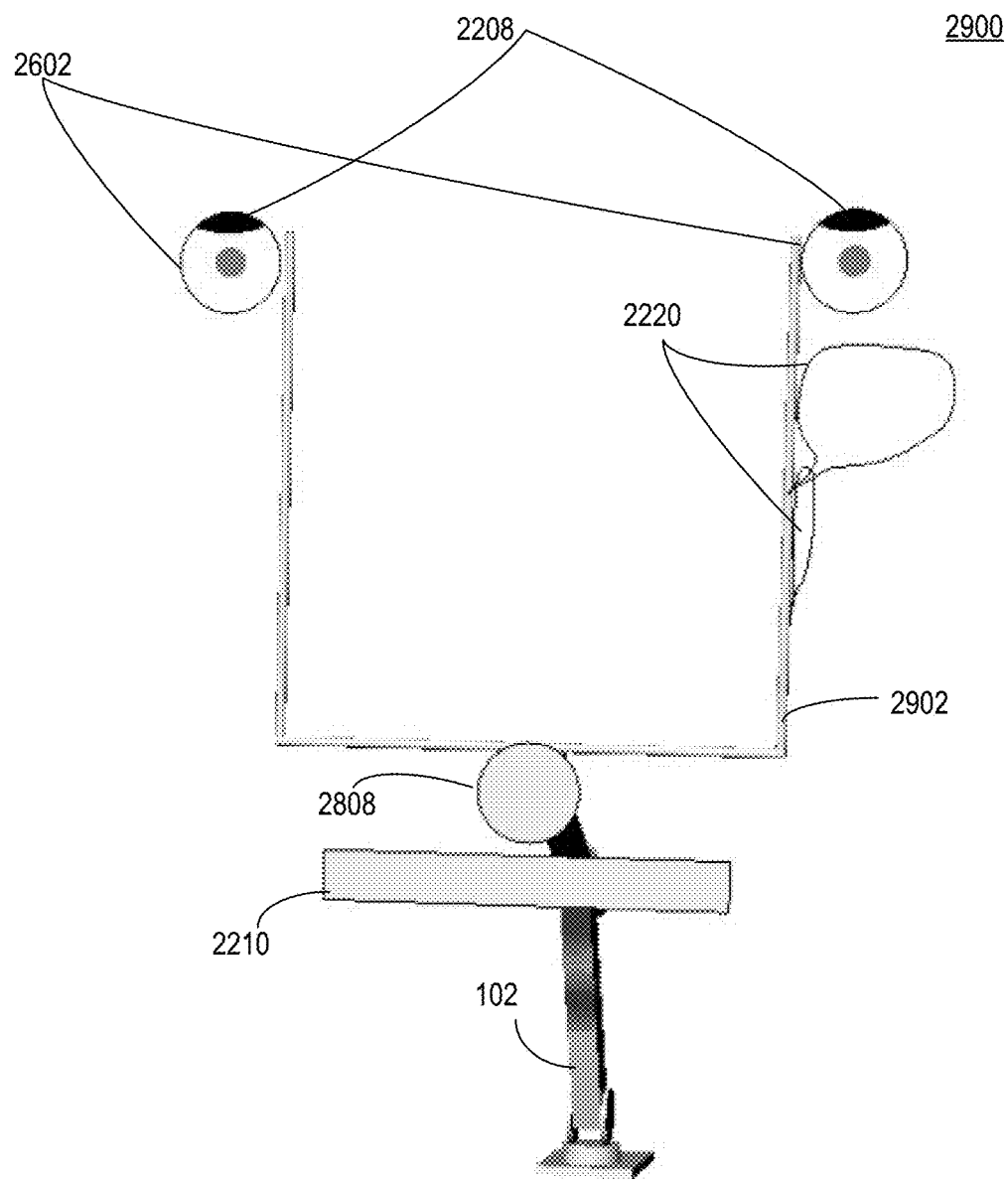
FIG. 29 depicts an exemplary diagram illustrating an exemplary embodiment of a personified sporting field goal, (with virtual and/or real personified enhancements) according to an exemplary embodiment.

FIG. 29 depicts an exemplary diagram 2900 illustrating an exemplary embodiment of a personified sporting field goal 2902, (with virtual and/or real personified enhancements) according to an exemplary embodiment. In an exemplary embodiment, personified attributes such as, e.g., but not limited to, eyes 2602, eyebrows 2208, nose 2808, mouth 2210, support and/or robotic base 102, as may allow exemplary movement and/or other personified attributes (e.g., nodding, shaking head), etc., such as, after a missed field goal, etc. Certain aspects can be provided via additional displays, such as, e.g., flat display screen(s), as discussed elsewhere herein, or as shown including exemplary speech bubbles 2220, and/or other features as may be optionally provided with displays, and/or via AR, MR, and/or VR through, e.g., but not limited to, head mounted displays, head up display, hololens, MAGIC LEAP, augmented reality, mixed reality, holographic lens, virtual reality glasses, enhanced reality glasses, GOOGLE Glass, a smartphone outfitted with camera for AR, etc., according to various exemplary but nonlimiting embodiments.

Figure 30:
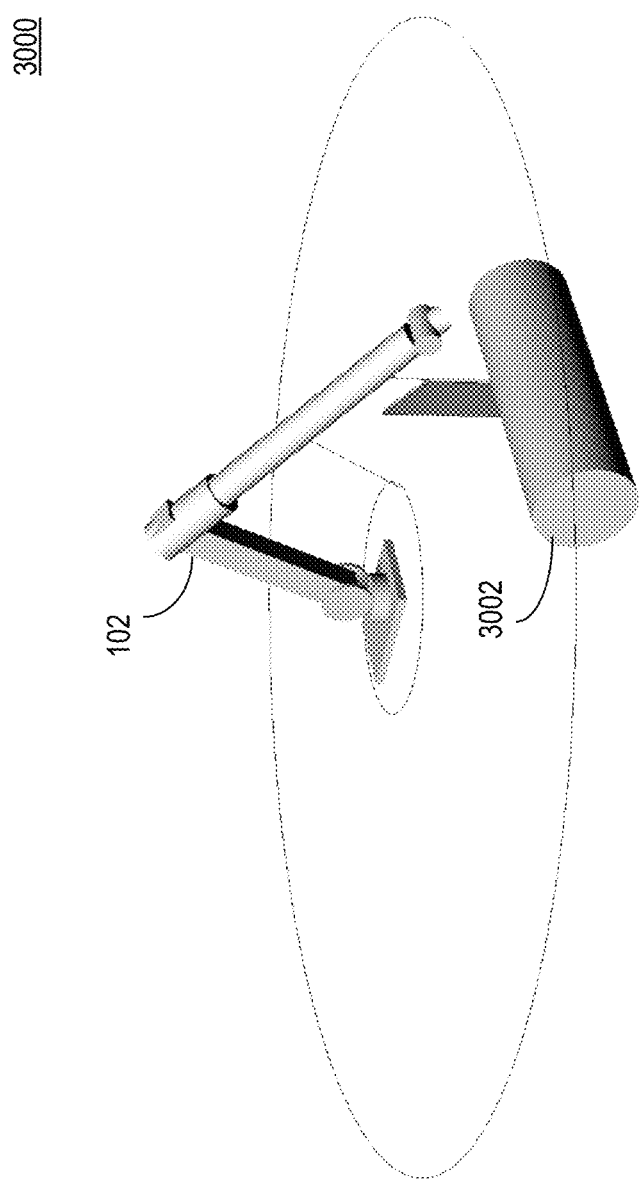
FIG. 30 depicts an exemplary swimming athletic training system including an exemplary robotic arm coupled to an exemplary tube and/or cylinder and/or compartment for analyzing a swimmer, and/or can be coupled via the robot to analyze drag, etc., according to an exemplary embodiment.

FIG. 30 depicts an exemplary swimming athletic training system including an exemplary robotic arm 102 coupled to an exemplary tube and/or cylinder and/or compartment for analyzing a swimmer, and/or can be coupled via the robot to analyze drag, etc., according to an exemplary embodiment.

Exemplary Embodiments of Additional Enhancements

Exemplary embodiments can include example modification of robotic arms so they can be used to pitch and/or hit baseballs and/or other balls including, e.g., but not limited to, tennis balls, etc., and other balls or projectiles used in sports, according to an exemplary embodiment.

Exemplary embodiments can include example purposes of employing the robotic arm to function in a similar manner as how the combination of a human arm, wrist, hand and/or fingers are used in a game to throw a baseball towards a catcher and/or a hitter, according to an exemplary embodiment. Thus a robotic pitcher can be used to pitch to a human catcher in one embodiment. In one embodiment a robotic pitcher can be used to pitch to a robotic robot.

General Statement

Exemplary embodiments can include example robotic arms which can be constructed in a manner that can be very similar to a human arm with a wrist that can rotate and the robots can have a device and/or component, like a hand and/or fingers that can grasp and/or manipulate an object, according to an exemplary embodiment.

Example #1—Robotic Pitcher

Exemplary embodiments can include example use of a robotic arm for the purposes of pitching a ball such as a baseball to a batter whereby the robotic arm can use the arm to propel or throw the ball as well as employing an additional device attached or part of the arm that can hold the ball in order to place a spin on the ball at different speeds of rotation and/or in different directions as the ball is released and/or thrown, according to an exemplary embodiment.

Exemplary embodiments can include example the robotic arm can be used to pitch a ball toward human batters and/or toward robotic batters, according to exemplary embodiments.

Differentiation of Robotic Pitcher

Exemplary embodiments can include an example robotic pitcher which can be different than present pitching machines which use two stationary spinning wheels to eject the ball toward a batter or an arm that catapults the ball toward the batter, according to an exemplary embodiment.

Exemplary embodiments can include example device which can be different because the movement of the robotic arm can mimic a human arm to give the ball velocity and the ancillary spinning wheels can be able to add different spins to the ball causing its path of travel to be deflected due to the changes in air pressure the spinning causes, according to an exemplary embodiment. Exemplary embodiments can include example spin which can be adjusted to cause the ball to drop, curve and/or change up and/or with minimal spin the ball can slowly travel through the air like a knuckle ball, according to an exemplary embodiment. The pitcher can implement randomness in variation of various aspects to create variation of pitches, and/or can provide consistency for other applications, according to embodiments. Sensors can be used, in exemplary embodiments.

Example #2—Robotic Batter or Hitter

Exemplary embodiments can include example use of a robotic arm connected or coupled to a bat and/or racket with sensor(s) to hit a ball as in the games of tennis, baseball, softball or cricket, etc., according to an exemplary embodiment.

Exemplary embodiments can include example a robotic arm which can swing a racket and/or bat to try and/or contact the ball so as to return the ball or to put the ball in play, according to an exemplary embodiment.

Exemplary embodiments can include example stationary robotic hitter(s), which could have two controllers, one for each team, according to an exemplary embodiment. Each team can activate their controller so that control of the stationary robot can be switched back and forth with the other team depending on which team is on the field and which is at bat, according to an exemplary embodiment.

Exemplary embodiments can include example where there can be some standard rules for both teams regarding exemplary hardware and/or sensor(s) that can be incorporated into and/or utilized in conjunction with the robot, in an example embodiment. Exemplary embodiments can include example sensor(s), as can be mounted on the robot and/or other sensor(s) can be stand alone, according to an exemplary embodiment.

Example #3—Modified Robotic Baseball Game

Exemplary embodiments can include an example robotic pitcher and/or robotic hitter could replace the current human pitcher and/or hitter, according to an exemplary embodiment.

Exemplary embodiments can include example human could still be required to control the pitching robot via an electronic computer controller and/or a human could be required to control the hitting robot via an electronic computer controller, according to an exemplary embodiment.

Exemplary embodiments can include example human players could still participate in the game and/or serve as a home plate catcher, fielder(s) and/or base runner(s), according to an exemplary embodiment.

Exemplary embodiments can include example robot(s), which can be programmed to avoid specific safe zones so that the robot and/or its bat can not enter a space that could be occupied by a catcher, runner and/or umpire and/or the umpire could control a master switch to keep any of the robot(s) from starting and/or moving unexpectedly, according to an exemplary embodiment.

Exemplary embodiments can include an example base runner could take their place next to the catcher and/or can start running to first base only once the ball has made contact with the bat, according to an exemplary embodiment. Exemplary embodiments can include an example false start could cause a strike against the batting robot, according to an exemplary embodiment.

Exemplary embodiments can include example strike zone could be depicted electronically and/or sensor(s) could be employed to determine if the ball actually entered the strike zone, according to an exemplary embodiment.

Exemplary embodiments can include example ball(s), which could have embedded sensor(s) to assist in the detection of their path of travel, according to an exemplary embodiment.

Exemplary embodiments can include example sensor(s), which could be employed such as, e.g., but not limited to, with a laser beam to ensure that the home plate base runner does not start running before contact between the bat and ball occur, according to an exemplary embodiment.

Exemplary embodiments can include where an example bat can have a sensor to detect when the bat and the ball make contact, according to an exemplary embodiment.

Exemplary embodiments can include example base runner(s) can still try to steal a base and/or the robotic pitcher can still try to throw them out, if they get too far off the base, according to an exemplary embodiment.

Exemplary embodiments can include an example robotic batter can still try to bunt the ball and the ball can be recovered by any of the players except the pitching robot, according to an exemplary embodiment.

Exemplary embodiments can include an example robotic pitcher, which can still start to fake a pitch and/or throw the ball to a base too, so the baseman can try and get a runner out, according to an exemplary embodiment.

Exemplary embodiments can include example robotic pitcher could have a number that can be displayed on the pitcher and their team insignia (which can be displayed in one embodiment) can change as their team takes and/or leaves the field, according to an exemplary embodiment. Exemplary embodiments can include where the example robot can even wear a team hat which can be placed on them when their team is on the field, according to an exemplary embodiment.

Exemplary embodiments can include example robotic pitcher and/or robotic batter can be personified and/or display gestures and/or emotions and/or can have other human features, according to an exemplary embodiment.

Exemplary embodiments can include example robotic batter can run, and/or take practice swings, etc., as human batters do when they step into the batters' box, according to an exemplary embodiment.

Exemplary embodiments can include an example robotic pitcher, which can turn and/or spin around, and/or make other motions to buy time as the pitcher prepares to throw the next pitch to the batter and/or to a baseman to get a runner tagged out, according to an exemplary embodiment.

Benefits

Exemplary embodiments can include example robotic baseball which can decrease or eliminate injuries to human pitchers' arms from repetitive throwing and/or to pitchers from being hit by hit line drive baseballs and/or loose bats, according to an exemplary embodiment.

Exemplary embodiments can include example ability of the robot to hit the ball can have enough variables depending on the sensor(s) utilized and/or other programming and/or mechanical variable(s) that an element of the unknown can, or should be inherent with each pitch, according to an exemplary embodiment.

Exemplary embodiments can include an example spin on the ball can create variables so that even though computers and/or robots can be used, the ball can never travel as perfectly as expected each time, so the game can still have plenty of variables that can make the game random, and entertaining, according to an exemplary embodiment.

Exemplary embodiments can include example use of robotic pitcher(s) and/or hitter(s) can dramatically speed up the tempo of the game and/or can decrease and/or eliminate continuous delays associated with, e.g., convention batter(s) stepping out of the box and/or adjusting their gloves, VELCRO brand straps, hook and loop fasteners, or the like, and/or grip and/or the delays of the pitchers contemplating their next pitch, according to an exemplary embodiment. It can cause the game to shift from one that is dominated with waiting for pitches and hits, to a game of hitting, fielding and base running which is in essence why spectators attend the games, according to an exemplary embodiment.

Exemplary embodiments can include an example home plate umpire which cannot have to make as many judgement calls and can be able to act in a more supervisory capacity, according to an exemplary embodiment.

Notes

Exemplary embodiments can include example current baseball league could introduce a rule that can provide a required time interval for the batter to be in the box and/or a required time interval for the pitcher to pitch the ball, but that does not lead to the agony of spectators such as conventionally experienced with game times having recently increased from 2 hours to 3 hours, according to an exemplary embodiment.

Exemplary embodiments can include example robotic baseball game could introduce significant technological advances into the game and/or can shift some of the technique and/or art of the game from the physical skills of human players on the field to a mental competition between programmers and/or hardware specialists who could also be on the field competing against the other team with their respective robot and/or controller, according to an exemplary embodiment.

Exemplary embodiments can include example public can be much more comfortable with technology and how it can be employed now versus twenty years ago so the public should not be as resistant to integrating robotic players with human players in sports, according to an exemplary embodiment.

According to another exemplary embodiment, exemplary robotic arms can be used in other sports, such as, e.g., but not limited in, in American football, soccer, etc., to e.g., but not limited to, celebrate a touchdown, a field goal, a soccer goal, etc. and/or to encourage crowd participation such as, e.g., but not limited to, similar to a cheer leader and/or public-address system, etc. According to another exemplary embodiment, the exemplary robotic arms can be used, e.g., but not limited to, to throw a ball, and/or other projectile, etc., according to an exemplary embodiment.

Additional Exemplary Embodiments

Exemplary embodiments can include example concept of using data from the robotic devices to establish player profile information which can be used in virtual games for new environments for competition, according to an exemplary embodiment. Exemplary embodiments can include an example dealing with a new concept of using the performance data for the creation of a virtual type of league of sporting games, according to an exemplary embodiment. Exemplary embodiments can include example equipment to collect, store, accumulate, and analyze the data, according to an exemplary embodiment.

Exemplary embodiments can include example use of the robot to provide an intermediate reference goal, see FIG. 13, for example, for a trajectory such as, e.g., but not limited to, in golf, and/or basketball, etc., so a player can aim for an intermediate target and/or can see the results relative to where the ball went and the relationship of the ball as it passes by or through the intermediate reference, according to an exemplary embodiment. Exemplary embodiments can include example size of the reference target and its position can be changed and/or the example target can contain, e.g., sensor(s) to indicate, capture, and/or record exactly where the trajectory was relative to the intermediate goal, according to an exemplary embodiment. Exemplary embodiments can include examples which can help athletes get a better fix on what works for them and the mix between arc and velocity, according to an exemplary embodiment.

Exemplary embodiments can include an example robot that, e.g., as illustrated in one exemplary embodiment in FIG. 30, can pull a swimmer in an example circle, or laterally along a rail (not shown) beside and/or in a pool with a measuring device that can be attached to the swimmer so they can see how much drag, and/or propulsion they are creating with each aspect of their stroke and/or the device can record the information and/or track the swimmer's progress, according to an exemplary embodiment.

Exemplary embodiments can include an example problem with trying to improve one's swimming can be that a swimmer can't measure how changes affect drag and/or increase propulsion, according to an exemplary embodiment. Conventionally, absent this disclosed invention, there is not a mechanical device that a swimmer can use to assist with this physical training, according to an exemplary embodiment. FIG. 30 depicts example apparatus 3000 including an example robot 102, coupled to an athletic training device 3002 enabling training and/or analysis of swimmer activity.

Exemplary embodiments can include example detection of how is one kick better than another and/or one hand scoop better, according to an exemplary embodiment. Exemplary embodiments can include example that can address the shortcomings of conventional solutions wherein no one can quantify and/or display the effect in a short period of time and the swimmer can conventionally be left to apply what they have been told in a timed interval, according to an exemplary embodiment.

Exemplary embodiments can include an example solution using an example robot and/or a harness that can be coupled to a swimmer, and/or other coupler, that can pull and/or drag a swimmer with a measuring device that can displays the swimmer's drag in, e.g., a very large example circle, and/or other shape, which can allow the swimmer to make changes and/or can instantly see the results and/or can do observe and/or make changes continuously without stopping, according to an exemplary embodiment. Exemplary embodiments can include an example where a swimmer can just glide and/or observe the resistance the swimmer may have with the water, according to an exemplary embodiment.

Exemplary embodiments can include example swimmer can be connected to, and/or coupled to, the robot via an example harness that can cover the swimmer's torso and/or can be coupled to a cable to a point on the back of the swimmer near the center of gravity, according to an exemplary embodiment.

Exemplary embodiments can include example deflector can be used to channel extra water to the inner side of swimmer in order to compensate and/or correct for the deflection caused by the rotational forces, according to an exemplary embodiment.

Exemplary embodiments can include example system, which can employ an exemplary breakaway safety and/or other device to release the cable in the event of some unusual circumstance, according to an exemplary embodiment.

Exemplary embodiments can include, an example robotic arm 102 that can pitch a baseball, according to an exemplary embodiment, as discussed above.

Exemplary embodiments can include an example robotic arm that can hit a baseball, according to an exemplary embodiment, as also discussed above.

Exemplary embodiments can include an example combination of an example robotic pitcher throwing a ball to an example robotic hitter to provide infield and outfield practice and fielding performance data, according to an exemplary embodiment.

Example Basketball Dribbling Practice Robot

FIG. 31 depicts an exemplary embodiment of a basketball dribbling practice robot according to an exemplary embodiment. According to an example embodiment, from having played and coached basketball, one of the most important things that Applicant tells players is that when one dribbles the ball, one must always protect the ball from one's opponent to avoid a steal. It is common to lift one's guard arm when protecting the ball or to use one's body to help protect the ball in this situation. This skill can be practiced alone but it can be hard to create a game realistic situation of someone reaching to steal the ball from the opposing player if one is practicing by oneself. One could attempt to find a person to help one practice this skill, but often it can be difficult to find someone available to assist one. According to an example embodiment, an example robotic arm can be programmed to try and reach for the basketball that one is dribbling, can help create the same situation that could be done with another person, however in an automated fashion using an electronic computer based robot. The example robotic arm can have one or more sensors, attached to the robot or robotic arm, which can be used by the robotic arm to locate where the ball is, and how far away from the robot and/or the player, that the ball is. In an example embodiment, the robot arm can then reach out and try to steal the ball from the person. In an example embodiment, the person can try to protect the ball, such as, e.g., but not limited to, knocking the hand away or rotating their body. The robotic hand can reach out and try to steal the ball every couple seconds and/or can have a workout timer for how long a user can practice ball handling with the machine, according to an example embodiment. According to an example embodiment, the use of the robotic training system can help an athletic user learn to protect the ball when dribbling, and can help the athletic user being trained on improving ball handling and/or ball control. In another example embodiment, the robot can be modified to include one or more sensors to help allow the robot to, e.g., dribble the ball relative to at least a part of the robot, such as, e.g., but not limited to, an example robotic hand, which can be coupled to an example robotic arm.

Example Basketball Dribbling Practice Robot

Example use of the terms "robotic arm" and/or "robot", etc., can be considered generally interchangeably and the terms are intended to mean the same thing in this disclosure. Use of the term "projectile" and "ball" are interchangeable as well, but can be thought to refer, collectively, to refer to the same example thing being acted upon by the robot, according to an example embodiment.

A. Combination catching and throwing robotic arm—according to an example embodiment, an example device can be capable of catching and/or then throwing a ball and/or a projectile, i.e., an example robotic pitching machine can be adapted to sense an incoming ball, can move to catch the ball, and can act to pitch and/or otherwise act to electronically manipulate the ball. According to an example embodiment, an example robot can be configured to include an example arm, and/or other components, which in one embodiment can include an example at least two components, including, e.g., but not limited to, an example first component that can catch, an example second component that can throw, and an example third mechanism by which the ball or projectile can be made to physically transition from the catching portion to the throwing portion, in one example embodiment.

Launching or throwing portion—According to an example embodiment, an example Robot can be capable of launching or throwing a projectile such as a ball or spear by placing a spin on the projectile as part of, or before, the projectile is released so that the projectile's path is not just an arc as can occur with a catapult. This invention applies to projectiles such as, e.g., but not limited to, baseballs, footballs, and the like, where a spin is often placed on the ball as it is released so that the rotation can cause the ball to travel in a specific manner towards a specific target. The direction and speed of the spin can also be changed, e.g., by, e.g., one or more mechanisms such as, e.g., but not limited to, wheels, and/or other mechanisms to cause the ball to spin in a particular way, so as to cause pressure differentials on the ball or projectile, as it moves through the air similar to how a baseball pitcher has a repertoire of options in how the pitcher throws a ball to the catcher at home plate and, can use the plurality of options to try to confuse the batter as to where, and how the ball is traveling.

The throwing component that contains, or grasps the ball before it is released can have an example cradle that can hold the ball and/or a spindle, and/or wheel and/or other propulsion mechanism, and/or other device capable of spinning and transmitting its rotational energy into the projectile before, or at the same time as, the projectile is released, and/or the wrist action can alone, or in combination, with that of the robotic arm can be sufficient to initiate the desired spin on the ball or projectile similar to what occurs when a hand rotates as it releases and/or throws a baseball or football. The mechanisms can be repeatably controllable to allow programming the device to perform the throwing process.

2. Catching portion—According to an example embodiment, an example robotic arm that can be configured to be capable of catching a projectile or ball in an example mitt or other capture mechanism, such as, e.g., but not limited to, an example baseball catcher's mitt and/or other device such that the ball is not damaged and/or dropped and whereby the ball can be made to stay in play, and/or in possession of the example robot arm and then can be displaced to the throwing side and/or portion of the robotic arm for return to the human pitcher or pitching robotic arm.

3. Transition portion—According to an example embodiment, an example robotic arm can be configured with a capability for catching and throwing that can have an example transition mechanism and/or section where the ball can move from the catching device to the throwing cradle and/or the catching mitt can be integrated with the throwing cradle whereby the spindle can be able to put a spin on and/or eject and/or pitch the ball from approximately the same location or vicinity where the ball was caught by and in the mitt.

B. Hitting or returning robotic arm—According to an example embodiment, an example robot capable of using a racket and/or bat to hit and/or return a projectile or ball back in the general direction from where it came or for hitting a projectile such as, e.g., but not limited to, a ball that has been independently launched and/or dropped in the close vicinity of the robot so that the robot can hit the ball such as, e.g., but not limited to, how a tennis ball is thrown up in service in the air at the beginning of play by the person who is putting the ball into play toward a specific target, and/or how a ball can be dropped from above and then hit on its way down.

According to an example embodiment, an example hitting robot can utilize sensors to detect the velocity and direction of the approaching and/or dropping ball and can be able to calculate where and how the ball can be hit with the bat or racket so as to cause the ball to return to a specific location at a specific velocity.

According to an example embodiment, an example hitting robot can be used for tennis practice and/or in fielding practice in baseball with human players on the field. According to an example embodiment, in an example game of tennis, a robot could be used for repetitive serves to a specific location on the court at various velocities, in the game of baseball the robot can be able to hit a ball in a specific way such as, e.g., but not limited to, at a specific angle or specific velocity so that the ball goes to a specific location on the field and/or in the game of football the robot can be able to throw the ball to the same location repeatedly for practice in running plays and/or evaluating players, etc. According to an example embodiment, an example robot can be able to hit a ball such as, e.g., but not limited to, a tennis ball and/or a baseball that can be independently launched in its close vicinity such as, e.g., but not limited to, how a tennis ball is thrown up in a serve and/or how a baseball is thrown up with one hand by a coach as he hits balls toward his players on the field in scouting, training and/or warm ups.

C. Combination of two robots competing with each other in a game—According to an example embodiment, an example robot can be configured to be throwing and the other robot can be configured for hitting, and/or both can be configured for hitting.

According to an example embodiment, an example combination of two different robotic arms, a) one throwing (or on defense), and b) another capable of hitting (or offense) could create an environment where the robots can be employed as part of a competition between two teams, as if the robots were players that were integrated as part of a baseball team with other human players or in a game between two machines without other human players such as, e.g., but not limited to, on a tennis court and/or at a ping-pong table which is also known as table tennis. The robots can be configured that their controllers be teleoperatively attended and operated by humans.

According to an example embodiment, an example of each robot can be connected to, and/or, can be operated by, at least one electronic controller or as in the game of baseball control of the hitting and throwing robots, which can be permanently mounted in place with one on the pitching mound and the other in the batters' box, could switch to the other team when the teams with their human players switch sides between hitting and fielding and the display of the team insignia for each robot could coincide with the change of control.

D. Personified Player Robots—According to an example embodiment, example robots on the field can be personified with ancillary human features such as, e.g., but not limited to, eyes, lips and/or ears to give the robot(s) the ability to manipulate and/or move these features in a way that can, e.g., but not limited to, display, express or communicate a human personality and/or character.

According to one example embodiment, example embodiments can assist in making it possible that technical people can get into professional sports via working with example systems such as those discussed in this disclosure.

In one example embodiment, a robot can play the part of one or more athletes in an example professional sport. Comparison of an example cost, of example robot(s) playing a part of a position conventionally played by of certain athletes (e.g., a pitcher, or a catcher in baseball, etc.), can be substantially less costly as compared relative to exorbitant conventional salaries that are paid to professional sports players. For example, an example salary of one average conventional professional player could potentially pay for a whole field of robots.

FIG. 32A depicts an exemplary embodiment of multiple basket goals in an exemplary horizontal orientation, according to an exemplary embodiment. There can be a plurality of different goals. There can be two, three, four, or more goals. The goals can be programmed to move continually.

FIG. 32B depicts an exemplary embodiment of multiple basket goals in an exemplary vertical orientation, according to an exemplary embodiment.

FIG. 32C depicts an exemplary embodiment of multiple basket goals in an exemplary horizontal orientation, with an example single robot to control the continuously movable goal, according to an exemplary embodiment.

FIG. 32D depicts an exemplary embodiment of multiple basket goals in an exemplary vertical orientation, with an example single robot to control the continuously movable goal, according to an exemplary embodiment.

FIG. 32E depicts an exemplary embodiment of multiple basket goals in an exemplary horizontal orientation, with an example plurality of robots to control the continuously movable goals, according to an exemplary embodiment.

FIG. 32F depicts an exemplary embodiment of multiple basket goals in an exemplary horizontal or vertical orientation, with an example single robot with a plurality of end effectors to control the continuously movable goals, according to an exemplary embodiment.

In another embodiment, conveyors can be used to bring out automated concessions to seats G-U, according to an embodiment, not shown. In another embodiment, drones can deliver food or drinks within the stadium, not shown.

Launcher and/or Package Delivery Storage Canister

In another example embodiment, a vehicle can have a launcher to launch packages to a house, according to an exemplary embodiment.

In another example embodiment, each house can have its own receptacle with automatic sensor based door/cover for protecting packages delivered into such receptacle, according to an exemplary embodiment.

Artificially intelligent (AI) based, with e.g., an expert system, or machine learning capabilities, can provide autonomous delivery van or driverless delivery van, can move within a zone and can deliver to example 3 feet×3 feet box which can open like a trash can to receive boxes, and can close and lock and include a power supply to open/close, and can use a solar panel to generate electricity, according to an exemplary embodiment.

Continuously Moving Athletic Sports Goals for Practice, Play, Competitions and League Formation According to an exemplary embodiment many applications of the exemplary invention can improve society, according to an exemplary embodiment. First, embodiments can create semi-professional athletic opportunities for the thousands of athletes and coaches that can like to participate in semi-professional sports, second embodiments can provide for the establishment of many financially viable local community based professional sports leagues, third embodiments can provide a framework for both male and female athletes and coaches of all ages to develop and maintain the social, physical and psychological benefits that are derived from being able to participate in organized competitive team activities, fourth embodiments can create new opportunities for athletes that have been excluded from particular sports because of height or other physical limitations, according to an exemplary embodiment, fifth embodiments can make sports competitions more interesting and entertaining by requiring more player teamwork in sports competitions versus teams being dependent on the exceptional talents of a few players, sixth embodiments can allow the players, games and leagues to serve as an example of how cooperation is more important than individual glory, and seventh embodiments can embodiments can create a new class of competitive sports leagues for spectator entertainment and enjoyment.

There are thousands of athletes playing high school and college sports that have the skills and interest in continuing to participate in organized athletics but cannot find semi-professional leagues to participate in because of limited options and monopolistic control of professional sports leagues and venues by the major sports franchises, according to an exemplary embodiment.

Embodiments can include the formation of new competitive sports leagues that can utilize permanently mounted equipment, or moveable equipment which can be capable of moving sports goals in a continuous manner installed in private facilities for the creation of new types of sporting activities and games where the goal is continually moving during the game instead of remaining static in a fixed position as universally applied and accepted today in games like conventional basketball, according to an exemplary embodiment.

The facilities can also be equipped with an array of many automatically operated high definition video cameras (see FIG. 33, for example) for the purposes of producing and streaming high definition quality video programming of the various sports league events to audiences within and beyond the immediate community, according to an exemplary embodiment. The creation of this new type of spectator sports and embodiments can include a capability for the efficient production of video programming can provide new funding opportunities via pay-per-view, individual branding and/or sponsorship or combinations of the three and the athletes and coaches can be able to derive an income from the sports entertainment content of their competitive athletic activities, according to an exemplary embodiment.

The embodiments of the invention can include continuously moving sports goals and can allow more players with different attributes to participate in these new games, according to an exemplary embodiment. An example of the opportunities for new players to participate in games with continuously moving goals can be illustrated in an analysis of the game of basketball whereby this invention of a continuously moving goal can neutralize the height advantage of taller players relative to the quickness of the shorter players so more shorter players can use their quickness to help advance the ball, score goals and participate on teams, according to an exemplary embodiment.

Basketball can be currently played with a goal that is in a fixed position which can allow the taller defensive players to always know its position relative to the offensive player and therefore the tall defensive players can maintain the best possible defensive position between the offensive player and the goal and be more successful in blocking attempted goals especially by those attempted by shorter players, according to an exemplary embodiment. By comparison, a continuously moving basketball goal is not as easy for tall players to defend because its position is continually changing which provides opportunities for shorter players to use their quickness to faint and move around the defending taller players who are unsure of its exact position or direction of movement, according to an exemplary embodiment.

The taller defensive player can be at a disadvantage with a moving goal because as the defensive player positions their body between the offensive player with the goal to their back the defensive player cannot see the position of both the offensive player and the goal at the same time because the goal is oscillating back and forth and continuously changing its position and location, according to an exemplary embodiment. This continuously moving, oscillating and changing goal position of embodiments can give the shorter players, who can always see the goal as well as the defensive player in front of them the opportunity to confuse and faint or fake the defending players which can add a new dimension of quickness and coordination to player rosters versus the domination of taller players on team rosters today as the game is currently played, according to an exemplary embodiment.

Games and competitions, according to an exemplary embodiment, can be provided with continuously moving goals moving at equal or different velocities and/or equivalent and/or multiple and/or different configurations of single and/or multiple goals and/or different sized goals in embodiments can also be more entertaining than games with static goals because players can have to improve their teamwork, game strategy and coordination of effort to score points as they work the ball to a position that is as close as possible to the goal(s) because longer distance shots as currently relied on and accomplished with extensive development of muscle memory can be negated due to the increased difficulty associated with hitting a moving target from a further distance, according to an exemplary embodiment.

Games can be configured to be played with more variables for goals provide many new options for scoring and handicapping based on the unique attributes of the different configurations, according to an exemplary embodiment. Smaller, higher, and faster moving goals can provide more scoring points because of their difficulty relative to larger, lower and slower moving goals which can by comparison be easier to score points and therefore less points can be earned or other options relative to the players and game score handicapping, can be provided, according to an exemplary embodiment.

Audiences can enjoy attending as well as remotely watching live athletic events on various electronic devices such as televisions, cell phones and computer terminals as well as in person but the facilities for the continuously moving sport goals can have limited if any spectators physically present because of site, facility and economic limitations and restraints, according to an exemplary embodiment. To be financially viable, the facilities for these competitions can be limited to the court area without space for spectators to be present, according to an exemplary embodiment. Instead of physically attending the games, the spectators can watch the games remotely via internet streaming to their electronic devices and even though the spectators won't be present they can be able to utilize their capability to transmit audio through the microphone on their personal electronic device for purposes of broadcasting their comments to the inside of the warehouse and/or other physical facility via an audio broadcast system installed within the facility so that the athletes participating in the event can be able to hear the murmur and loud comments of the spectators as if the spectators were physically present in the facility via a high quality, well positioned and amplified sound system, according to an exemplary embodiment.

The permanently mounted robotic equipment that moves the goals can be configured for different types and sizes of sports goals so the indoor arenas can also be used for other individual and team sports such as lacrosse, soccer, tennis, frisbee, hockey, archery, etc., according to an exemplary embodiment.

Figure 33:
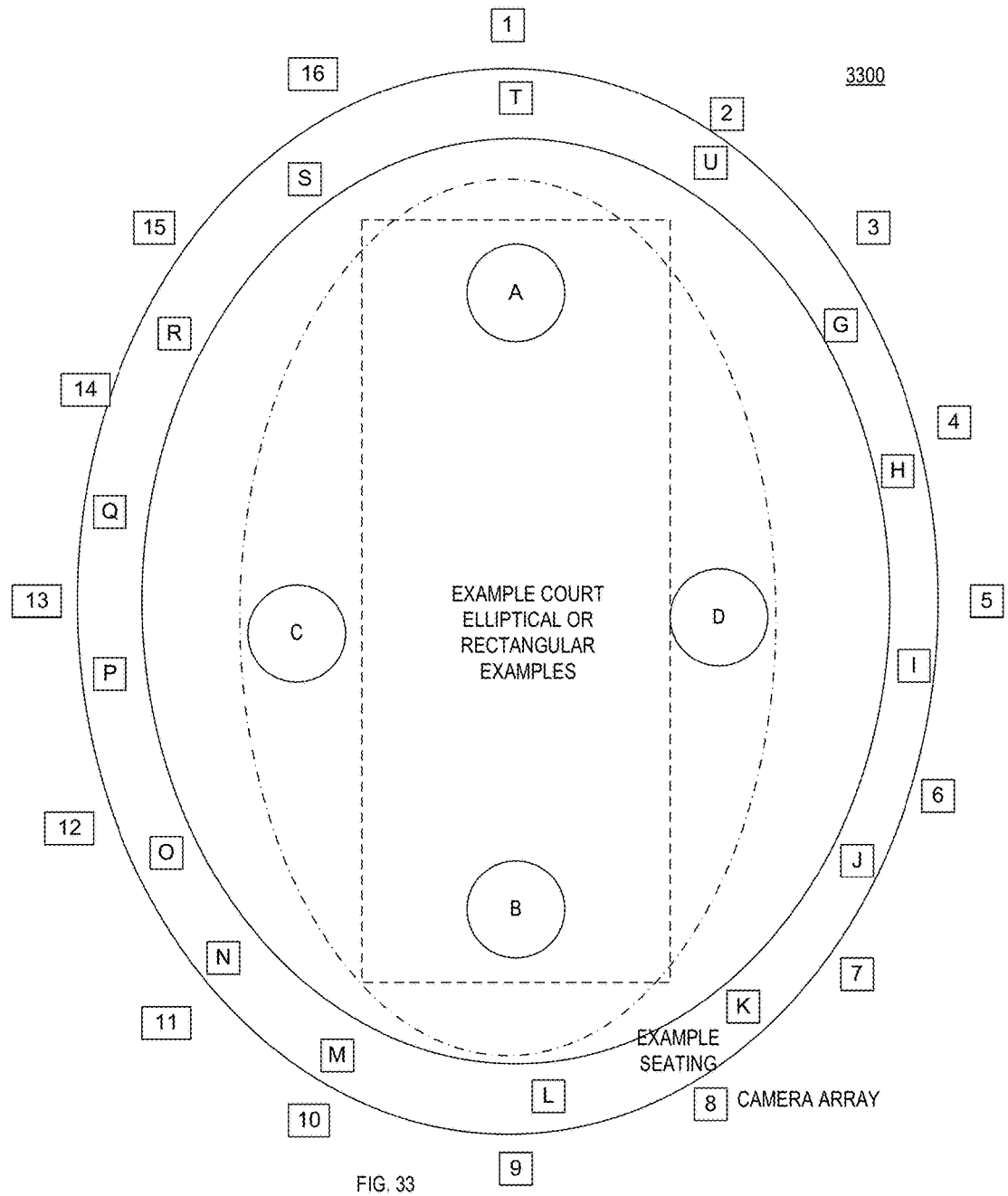
FIG. 33 depicts an example stadium with example multiple goals (circles A-D), example court polygon shapes, such as elliptical and rectangular, the stadium can be an amphitheatre arrangement with one or more seats (squares G-U), and an array of cameras (boxes 1-16) catching the competition, according to an example embodiment.

FIG. 33 depicts an example stadium with example multiple goals (circles A-D), example court polygon shapes, such as elliptical and rectangular, the stadium can be an amphitheater arrangement with one or more seats (squares G-U), and an array of cameras (boxes 1-16) catching the competition, according to an example embodiment.

Example embodiments can include:

One or more continuously moving sports goals mounted on very heavy industrial robotic arms that can be securely bolted in place to a sufficient foundation and can, in some embodiments, utilize electricity of a very high voltage to operate, can be provided, according to an example embodiment.

Competitive sports leagues and practice facilities that utilize continuously moving sports goals for athletic practice as well as for individual and team competitions, can be provided, according to an example embodiment.

Sports facility/arenas with computer manipulated cameras installed and configured to track and focus on the ball and specific players, can be provided, according to an example embodiment.

Balls or other sports device or players with electronic sensor/transmitter or specific coating or color so that a tracking device on a video camera can track or follow the sports device or player while it/they move around on a playing court or field for the purpose of maintaining the sports device or player in the field of view of the camera and such that the camera can zoom in or out and focus on the device/player being tracked, can be provided, according to an example embodiment.

An algorithm capable of adjusting zoom and camera view framing relative to the action occurring on the court or some other variable, can be provided, according to an example embodiment. (Cameras already have the technology for automatic focusing.)

Sports facility/arenas with remote user manipulated cameras installed, configured and positioned as if they, the remote user, was located in place of a specific seat at an arena so people can be seated with their family and or friends as if they were physically in attendance at the game and they can control the camera as if they were using binoculars at an event, can be provided, according to an example embodiment. The cameras can even be personified with the face of the user via a display screen, according to an example embodiment.

Spectators viewing the game via streaming can use headsets to listen to the game and their own remote microphones to participate in the live event as if they were in attendance, according to an example embodiment. Within the area, algorithms can be employed to control the volume and direction of the sound created by the remote spectators from the location where the spectator's controlled camera operates and in proximity to the other spectators and the court, according to an example embodiment.

An exemplary embodiment of the sporting apparatus can further include: at least one flat panel display coupled to said at least one sporting device; at least one transparent protective cover configured to: allow viewing of said at least one flat panel display; and protect said at least one flat panel display from impact of at least one of: at least one ball, or at least one projectile, being aimed at said at least one sporting device.

The sporting apparatus can further include: at least one animatronic appendage or facial feature.

The sporting apparatus can further include: where the user comprises at least one of: audience user; a player user; or a referee user.

The sporting apparatus can further include at least one of: a wireless communication facility wirelessly coupling said at least one sporting goal device and said at least one user interface, wherein said wireless communication facility is configured to communicate to said at least one sporting goal device; at least one audio or at least one video device coupled to said at least one sporting goal device configured to display, capture, or produce audio or video personified attributes; at least one speaker or at least one microphone coupled to said at least one sporting goal device configured to produce or capture personified sound; at least one sensor coupled to said at least one processor configured to sense a ball or projectile proximate to said at least one goal; at least one robot coupled to said at least one sporting goal device; or at least one flat panel display coupled to said sporting goal device, configured to display personified attributes comprising at least one of: at least one light emitting diode (LED) or LED back light coupled to said sporting goal device; at least one liquid crystal display (LCD) coupled to said sporting goal device; or at least one transparent, protective covering of said flat panel display.

In one example embodiment, a robot goal, or participant driver, and/or drone driver of the robot or drone can be positioned in a designated area, in one example embodiment, a controller bubble, and the driver, or in some cases, even the audience by entry of requests by electronic communication such as message or selection of a website user interface element can control the robot. Thus, in one embodiment, the driver of the goal, or a drone can be in the bubble. The driver of the Drone can try to take a ball and make a basket, while the driver of the goal, in one embodiment can evade the efforts to make a basket.

In one example embodiment, an array of cameras can be set up around a stadium. This array of cameras, in one embodiment, can focus on activity on the playingfield (which can be of any shape such as circular, ellipse, rectangle, square, triangular, hexagon, octagon or other polygon, etc.) and can automatically follow movement any person or object on the field, such as, a moving robot, a flying drone, a competing robot, or competitor. Others, with permissions granted, can electronically access these electronic digital video camera feeds and/or in real-time or otherwise, can electronically switch between the plurality of different electronic digital camera feeds. Then authorized users can access, compile, and/or aggregate into compilations, creation their own derivative content from the electronic data of the plurality of camera feeds' digital content.

An exemplary automated newspaper launcher system for an automobile or other vehicle or drone, or aerial vehicle can allow the user to send newspapers, or other objects such as, e.g., but not limited to, packages, etc. from the front of the car/vehicle, to a destination, such as, a person's home. One method can have a receptacle at the front of the house for example. The example receptacle at the front of the house can include a predictable location where a drone delivery apparatus can drop the package into the receptacle, and/or the launcher system can deliver packages into the receptacle. The example so-called last mile solution can be important because it can give access for dropping off things the receptacle. Services provided in some embodiments can include climate control, such as, e.g., air conditioning or cooling, heating, humidity control, etc., it in certain environments some kind of temperate temperature maintaining subsystem. The object can enter the climate controlled receptacle, which can have a door or automated cover device to protect the cavity for receiving the payload and the cover can prevent the payload from environmental impact of rain snow or other precipitation as well as to help maintain climate control the receptacle. The apparatus can further include electrical access HVAC digitally controlled temperature password control for access to open to place to remove the receptacle can include multiple sub receptacle portions for example one for FedEx one for the US Postal Service, DHL etc., each receptacle can have separate Access Control such that only an authorized delivery service can it gain access to the payload holding bay associated with such delivery company. The customer itself can of course access these things by entry of a password or all other authenticating means such as biometric systems including fingerprint control, Iris control, voice-activated control, voice identifying voice recognition system, and/or other biometric and/or validation.

While various embodiments of the present invention have been described above, it should be understood that they have been presented by way of example only, and not limitation. Thus, the breadth and scope of the present invention should not be limited by any of the above described exemplary embodiments, but should instead be defined only in accordance with the following claims and their equivalents.

What is claimed is:

1. A sporting robotic device apparatus comprising:
at least one or more of:
 a plurality of sporting devices coupled to at least one robot; or
 a plurality of said at least one robots, wherein said plurality of robots each comprise a sporting device coupled to said each of said plurality of robots; and
wherein said at least one robot comprises:
 a plurality of joint axes,
  wherein each joint axis of said plurality of joint axes comprises:
   at least one motor;
  at least one structural member coupled to at least one of said each of said plurality of joint axes motors,
  wherein each of said at least one motor is configured to move an associated coupled at least one of said at least one structural member; and
wherein the sporting robotic device apparatus further comprises:
at least one electronic user interface coupled to said at least one robot or said plurality of robots, configured to interact with a user to receive a selection of at least one sporting routine for moving said plurality of sporting devices or said sporting device;
at least one electronic computer processor, coupled to said at least one robot, or said plurality of robots;
at least one electronic input device coupled to said at least one electronic computer processor;
at least one electronic output device coupled to said at least one electronic computer processor;
at least one electronic memory device coupled to said at least one electronic computer processor; and
further comprising at least one or more of:
 wherein said electronic user interface comprises at least one of:
  an electronic display device,
  said at least one electronic input device,
  said at least one electronic output device,
  an electronic keyboard, or
  an electronic touchscreen;
 wherein said at least one electronic computer processor is configured to save or retrieve said at least one sporting routine from said at least one memory;
 wherein said at least one electronic computer processor is configured to randomize at least one challenge by said at least one sporting device; or
 wherein said electronic computer processor is configured to at least one or more of:
  combine a plurality of previously saved of said at least one sporting routine, or
  shuffle a plurality of previously saved of said at least one sporting routine.

2. The sporting robotic device apparatus according to claim 1, wherein said at least one sporting device comprises being configured to at least one or more of:
pitch or throw;
catch or hit;
automatically adjust;
automatically move;

move, adjust or modify position;
move in at least to directions;
move or adjust with respect to player position;
move with at least one of velocity, or acceleration;
automatically move in at least one of a horizontal, or a vertical, plane;
adjust or move at least one goal;
adjust or move at least one target;
adjust or move in up to five axes of freedom relative to a support;
adjust or move with at least one fixed dimension;
adjust or move within a precise vertical or horizontal dimensional range;
provide at least one sporting goal for a game;
provide a plurality of sporting goals for a game;
provide an adjustable or moving goal;
provide at least one goal automatically moveable based on a received input; or
provide at least one goal stationary for at least a predetermined interval.

3. The sporting robotic device apparatus according to claim 1, wherein said at least one sporting device comprises at least one or more of:
a target;
a goal;
a ring;
a closed loop;
a closed polygon with an opening therein;
a ring between the user and a final target;
a border with an aperture therethrough;
a ring between the user and a final goal
a pitching capability;
a throwing capability;
a catching capability;
a hitting capability;
an offensive capability;
  a defensive capability;
  a goal;
  a basketball goal;
  a soccer goal;
  a target;
  a hockey goal;
  a field hockey goal;
  a hockey goal;
  a winter sports goal;
  a summer sports goal;
  a shooting sports target;
  an archery goal;
  a field goal;
  a lacrosse goal;
  a tennis target;
  a golf target;
  a football target;
  an intermediate goal;
  a plurality of goals; or
  a FRISBEE flying disc golf goal.

4. The sporting robotic device apparatus of claim 1, wherein said sporting device is configured to provide at least one feature, attribute, or movement comprising at least one or more of:
  at least one sports attribute;
  at least one attribute associated with said sporting device;
  at least one body part; or
  at least one character associated with said sporting device.

5. The sporting robotic device apparatus of claim 1, further comprising at least one or more of:

wherein said plurality of sporting devices or said plurality of robots are configured to be associated with opposing teams of a game;
wherein said plurality of sporting devices or said plurality of robots are configured to compete against one another in a game;
wherein said plurality of sporting devices or said plurality of robots are configured to each be associated with a separate electronic controller;
wherein said plurality of sporting devices or said plurality of robots are configured to be continuously moving during at least one of a game, practice, play, competition, or league;
wherein said plurality of sporting devices or said plurality of robots are configured to be associated with at least one of a launcher, or a package delivery storage canister, or a launcher and package delivery storage canister;
wherein said plurality of sporting devices or said plurality of robots are configured to be associated with and situated about a stadium;
wherein said plurality of sporting devices or said plurality of robots are configured to be associated with a plurality of cameras situated about a stadium;
wherein said plurality of sporting devices or said plurality of robots are configured to be associated with a plurality of image or video capture devices in a stadium;
wherein said plurality of sporting devices or said plurality of robots are configured to be continuously at least one of: animated, or moving, in a stadium;
wherein said plurality of sporting devices or said plurality of robots are configured to be associated with automatically focusing or following cameras;
wherein said plurality of sporting devices or said plurality of robots are configured to be wirelessly coupled to a wireless device;
wherein said plurality of sporting devices or said plurality of robots are wirelessly coupled drone devices in a stadium;
wherein said plurality of sporting devices or said plurality of robots are flying drone devices in a stadium;
wherein said plurality of sporting devices or said plurality of robots are underwater drone devices in a pool;
wherein said plurality of sporting devices or said plurality of robots is a robotic catcher;
wherein said plurality of sporting devices or said plurality of robots is a robotic pitcher;
wherein said plurality of sporting devices or said plurality of robots is a robotic dribbler;
wherein said plurality of sporting devices or said plurality of robots is a robotic defender;
wherein said plurality of sporting devices or said plurality of robots is a robotic offensive device;
wherein said plurality of sporting devices or said plurality of robots is an animated, augmented reality, virtual reality, or display based display, backboard or goal;
wherein said plurality of sporting devices or said plurality of robots comprise three or more sporting devices;
wherein said plurality of sporting devices or said plurality of robots comprise four or more sporting devices; or
wherein said plurality of sporting devices or said plurality of robots comprise an elliptical, circular, rectangular, square, triangular, pentagonal, hexagonal, septuagonal, octagonal, or polygon-shaped court in a stadium.

6. The sporting robotic device apparatus of claim 4, wherein said at least one body part comprises at least one or more of:

a mouth;
at least one eye;
at least one leg;
at least one arm;
at least one hand;
at least one foot;
at least one eyebrow;
at least one tooth;
at least one tongue; or
at least one eyelash.

7. The sporting robotic device apparatus of claim 4, wherein said at least one character comprises at least one or more of:
at least one representation of a mascot;
at least one representation of a comedic character;
at least one representation of a cartoon character;
at least one representation of an animated character;
at least one representation of a personified pet;
at least one representation of a person; or
at least one representation of a personified object.

8. The sporting robotic device apparatus of claim 4, wherein said at least one character comprises at least one representation of a personified object, comprising at least one or more of:
at least one representation of a personified robot;
at least one representation of a personified automobile;
at least one representation of a personified snowperson;
at least one representation of a personified monster;
at least one representation of a personified animated character;
at least one representation of a fictional character;
at least one representation of a personified insect; or
at least one representation of a personified animal.

9. The sporting robotic device apparatus of claim 8, wherein said at least one character comprises at least one representation of an object, wherein said object comprises at least one representation of an animal comprising at least one or more of:
at least one representation of a reindeer;
at least one representation of a deer;
at least one representation of a elephant;
at least one representation of a mouse;
at least one representation of a duck;
at least one representation of a fish;
at least one representation of a personified pet;
at least one representation of a dragon;
at least one representation of a lion; or
at least one representation of an owl.

10. The sporting robotic device apparatus of claim 8, wherein said at least one character comprises at least one representation of a object, wherein said personified object comprises at least one representation of an insect comprising at least one or more of:
at least one representation of an ant;
at least one representation of a spider;
at least one representation of a grasshopper; or
at least one representation of a bug.

11. The sporting robotic device apparatus of claim 4, wherein said at least one feature, attribute, or movement, comprises at least one or more of:
at least one behavior; or
at least one emotion.

12. The sporting robotic device apparatus of claim 11, wherein said at least one feature, attribute, or movement comprises said at least one behavior or said at least one emotion, comprising at least one or more of:
a smile;
a laugh;
a frown;
a wink;
a gesture;
a face or gesture depicting anger;
at least one representation of happiness;
at least one representation of sadness;
at least one representation of anger;
a face or gesture depicting crying;
a face or gesture depicting vomiting; or
a face or gesture depicting eating.

13. The sporting robotic device apparatus of claim 11, wherein said at least one feature, attribute, or movement comprises said at least one behavior or said at least one emotion comprises at least one interaction, comprising at least one or more of:
at least one voice;
at least one representation of an emotion;
at least one representation of a relationship;
at least one representation of a familial relationship; or
at least one representation of a sporting relationship.

14. The sporting robotic device apparatus of claim 12, wherein said at least one feature, attribute, or movement, comprises said at least one behavior or said at least one emotion comprising at least one gesture, and wherein said at least one gesture comprises at least one or more of:
at least one facial gesture;
at least one body part gesture; or
at least one hand gesture.

15. The sporting robotic device apparatus of claim 5, wherein said at least one feature, attribute, or movement comprises at least one or more audio, video, or display of at least one communication.

16. The sporting robotic device apparatus of claim 15, wherein said at least one feature, attribute, or movement comprises said at least one audio, video, or display of said at least one communication, comprising at least one or more of:
at least one bubble of text;
at least one audio message;
at least one text message;
at least one video message;
at least one taunt;
at least one commentary;
at least one criticism;
at least one encouragement;
at least one cheer;
at least one text box;
at least one song.

17. The sporting robotic device apparatus of claim 11, wherein said at least one feature, attribute, or movement comprises said at least one behavior or said at least one emotion comprises at least one interaction, wherein said interaction comprises at least one or more of:
at least one interaction with an athlete;
at least one interaction with an audience; or
at least one interaction with a referee.

18. The sporting robotic device apparatus of claim 11, wherein said at least one feature, attribute, or movement comprises said at least one behavior or said at least one emotion, and further comprising at least one or more of:
wherein emotions are controlled by at least one user device;
wherein emotions are programmed;
wherein emotions are controlled by an artificial user device; or wherein emotions are controlled by an artificial intelligence software agent.

19. The sporting robotic device apparatus of claim 11, wherein said at least one feature, attribute, or movement comprises said at least one behavior or said at least one emotion comprises at least one interaction, further comprising at least one or more of:
   wherein said sporting comprises:
      an ejector, wherein said ejector simulates spitting the at least one ball, or the at least one projectile out, said ejector configured to:
         receive at least one of:
            at least one ball, or
            at least one projectile; and
         eject said at least one ball or said at least one projectile; or
   at least one sensor configured to sense a ball or projectile proximate to said at least one sporting device.

20. The sporting robotic device apparatus according to claim 1,
   wherein each said at least one sporting device comprises at least one or more of:
      said at least one electronic computer processor, coupled to said each said sporting device;
      said at least one electronic memory device, coupled to said each said sporting device, and coupled to said at least one electronic computer processor;
      said at least one of said at least one electronic input or said at least one electronic output device, coupled to said each said sporting device, and coupled to said at least one electronic computer processor; or
      said at least one electronic user interface, coupled to said each said sporting device, and coupled to said at least one electronic computer processor.

* * * * *